(12) United States Patent
Campbell et al.

(10) Patent No.: US 12,383,669 B1
(45) Date of Patent: Aug. 12, 2025

(54) GRAVITY-FED BURETTE SYSTEM

(71) Applicant: Stratos Medtech Holdings Pty Ltd, Queensland (AU)

(72) Inventors: Thomas G Campbell, Newbury Park, CA (US); Ross James Mangelsdorf, Sydney (AU); Michael Phillip Monsour, Sydney (AU)

(73) Assignee: STRATOS MEDTECH HOLDINGS PTY LTD, Maryborough (AU)

( * ) Notice: Subject to any disclaimer, the term of this patent is extended or adjusted under 35 U.S.C. 154(b) by 0 days.

(21) Appl. No.: 18/752,035

(22) Filed: Jun. 24, 2024

(51) Int. Cl.
*A61M 5/14* (2006.01)

(52) U.S. Cl.
CPC .................................. *A61M 5/1412* (2013.01)

(58) Field of Classification Search
CPC .............. A61M 16/0093; A61M 1/782; A61M 5/1412; A61M 25/002; A61M 5/002; A61M 39/22; A61M 2039/229; A61M 5/16877; A61M 5/16881; A61M 5/1408; A61M 5/1409

See application file for complete search history.

(56) References Cited

U.S. PATENT DOCUMENTS

| | | | | |
|---|---|---|---|---|
| 4,553,964 A | * | 11/1985 | Sasaki | G01F 11/28 D24/117 |
| 5,334,170 A | * | 8/1994 | Moroski | A61M 5/1412 604/80 |
| 5,885,532 A | * | 3/1999 | Maltabes | A61M 5/1412 422/106 |
| 5,947,890 A | * | 9/1999 | Spencer | A61M 25/10182 600/3 |
| 6,776,158 B1 | * | 8/2004 | Anderson | A61M 16/0093 119/419 |
| 2008/0116106 A1 | * | 5/2008 | Lampropoulos | A45C 11/24 53/425 |
| 2009/0088710 A1 | * | 4/2009 | Hoffman | A61M 1/78 604/323 |
| 2012/0177749 A1 | * | 7/2012 | Tapolsky | A61K 31/00 435/375 |
| 2023/0158242 A1 | * | 5/2023 | Vamja | A61M 5/3129 604/187 |

* cited by examiner

*Primary Examiner* — Lauren P Farrar
(74) *Attorney, Agent, or Firm* — Roy L Anderson

(57) ABSTRACT

A closed, gravity-fed burette for intravenous (IV) fluid delivery and flush system supporting multiple input combinations for simplicity and standardization. Able to handle both hazardous and non-hazardous drugs, this system may incorporate plastic and elastomeric materials that are resistant to the effects of antineoplastic materials in conjunction with a hazardous air filter module while still integration compatible with electronic peristaltic pumps for finer control of flow rate and when the IV infusion recipient's physical position is not compatible with a gravity-fed flow. The buoyant-activated shuttle valve enables the AutoStart function providing steady flush of the IV line to the patient for optimized vein patency from the Primary IV fluid feed. This Primary line works in conjunction with a Secondary IV fluid feed and a needleless connector Drug Port for multiple feed and flush conditions directed by way of a monoblock design supporting combinations of rotary, toggle, and check valves.

17 Claims, 44 Drawing Sheets

Set Up with a Single IV Bag

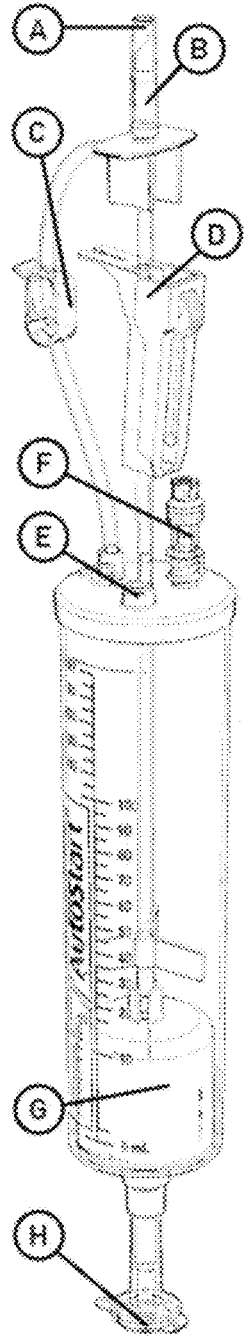

- Close Roller Clamp D & Bypass Clamp C / Open Filtered Vent E
- Remove Spike Cap A & puncture IV bag
- Open Roller Clamp D – fluid begins to fill the Chamber & will be stopped by Float G at approx. 7-10ml
- Open Spike Port H & connect an infusion set
- Prime the system according to protocol – Device ready for use in AutoStart mode

Medication Delivery

- Open Bypass Clamp C & fill Chamber to desired level & close Bypass Clamp C
- Add medication via injection to Needleless Connector Port F
- Open Bypass Clamp C, pull flush into injector & push into Chamber – closing ByPass Clamp C when compete
- Medication flow rate managed by flow control system below the Spike Port H
- Upon exhaustion of Secondary Bag contents in the Chamber, AutoStart mode will commence to flush the line supporting patency of the catheter site Prior Art

FIG. 5

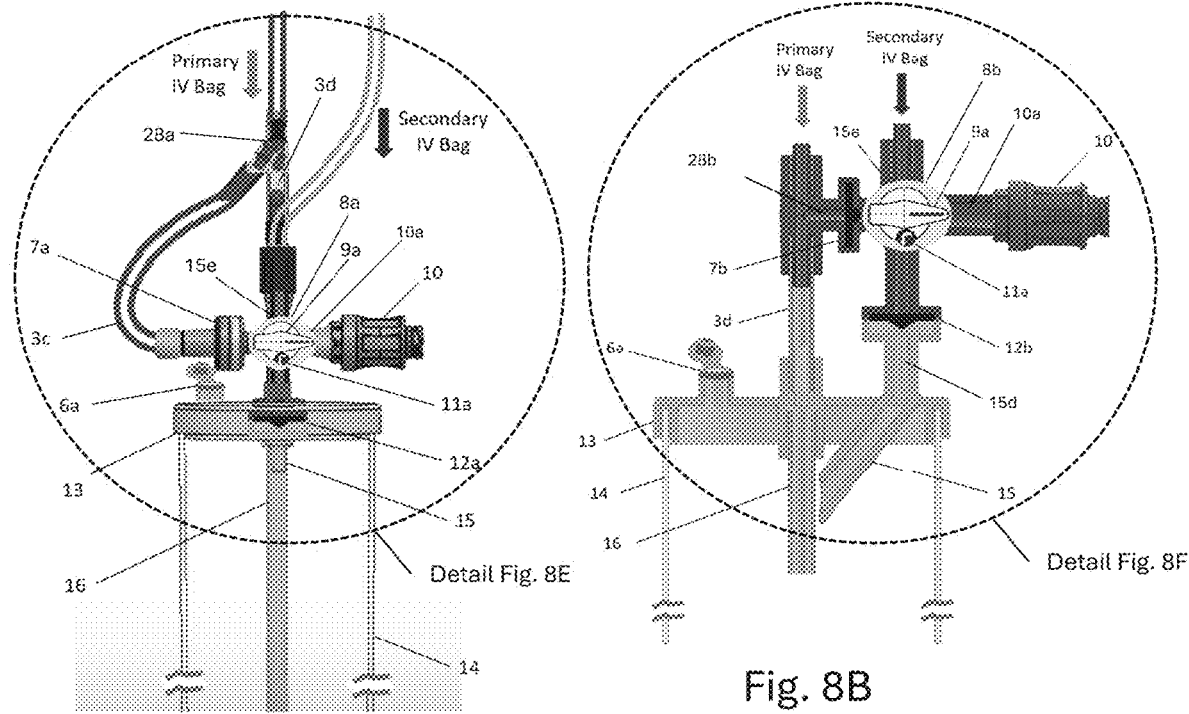
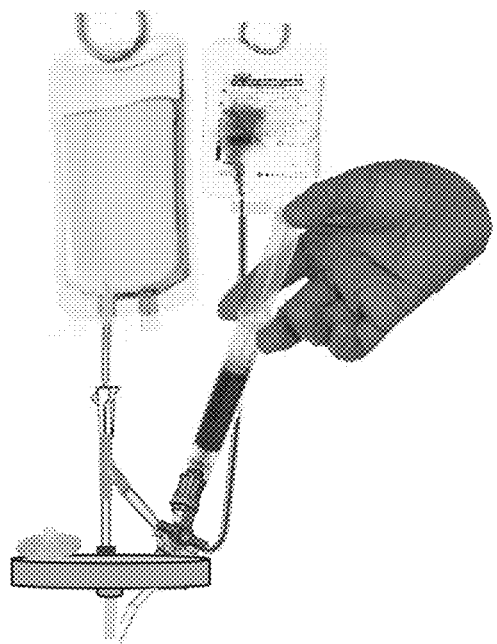
Fig. 8A
Fig. 8B
Fig. 8D
Fig. 8C

| Vesicants | Irritants | Nonvesicants | |
|---|---|---|---|
| Mitotic Inhibitors | Antimetabolites | Antimetabolites | |
| Non-DNA Binding | Not Vesicants | Topoisomerasi I Inhibitors | Gemcitabine |
| Vinorelbine | Taxanes | Irinotecan | Methotrexate |
| Alkaloids of Vinca: Vinblastine | Docetaxel | Topotecan | |
| Vincristine | Paclitaxel | | Azacitidine |
| Vindesine | | Anthracyclines | 5-fluorouracil |
| | Cabazitaxel | Topoisomerasi II Inhibitors | 6-mercaptopurine |
| | Nab-paclitaxel | Etoposide | Capecitabine |
| DNA Binding | | Teniposide | Cladribine | Other |
| Alkylating Agents | | | Clofarabine | Chemo |
| Anti-Tumor Antibiotics | | Liposomal doxorubicin | Cyclophosphamide | Drugs |
| Doxorubicin | | Mitoxantrone | Cytarabine | All-trans- |
| | | | Decitabine | retinoic acid |
| Anthracyclines | | Antimetabolites | Floxuridine | Asparaginase |
| Bendamustine | | Alkylating Agents | Fludarabine | Eribulin |
| Dactinomycin | | Altretamine | Hydroxyurea | Hydroxyurea |
| Daunorubicin | | Bendamustine | Nelarabine | Mitotane |
| Epirubicin | | Busulfan | Pemetrexed | Pegaspargase |
| Idarubicin | | Carboplatin | Pentostatin | Vorinostat |
| Mechlorethamine | | Carmustine | Pralatrexate | |
| Mitomycin C | | Chlorambucil | Raltitrexed | |
| Mitoxantrone | | Cisplatin | Temsirolimus | |
| Trabectedin | | Dacarbazine | Thioguanine | |
| Thiotepa | | Fluorouracil | Trifluridine/tipiracil | |
| | | Ifosfamide | | |
| | | | Anti-Tumor | |
| Nitrosoureas | | Lomustine | Antibiotics | |
| Carmustine (BCNU) | | Mechlorethamine | Actinomycin D | |
| Lomustine (CCNU) | | Melphalan | | |
| Streptozocin | | Oxaliplatin | Interferons | |
| | | Platin salts | Interleukin-2 | |
| | | | Monoclonal | |
| Other Chemo | | Streptozocin | Antibodies | |
| Drugs | | Temozolomide | | |
| Arsenic trioxide | | Thiotepa | Corticosteroids | |
| Ixabepilone | | | Prednisone | |
| Omacetaxine | | Anti-Tumor Antibiotics | Methyl prednisone | |
| Procarbazine | | Bleomycin | Dexamethasone | |
| Romidepsin | | | | |

▓▓▓ = Light-sensitive drugs that require IV fluid delivery systems to be amber-colored or opaque, employ light protective coverings, be administered in darkened environments, or perform overall timely preparation to minimize the duration of exposure to light.

FIG. 29

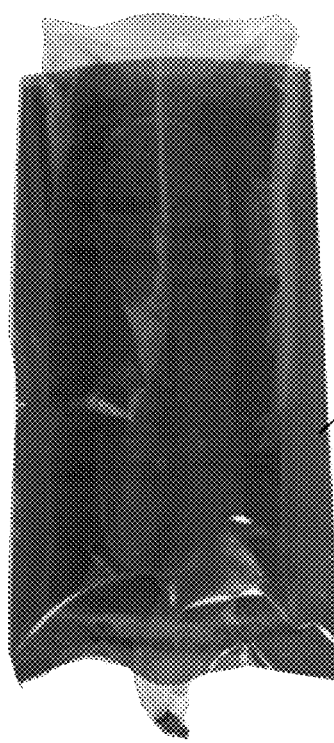
FIG. 30A
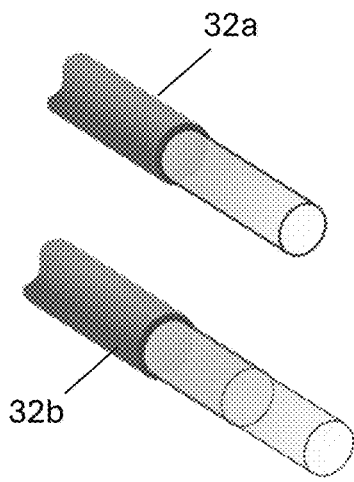
FIG. 30B
FIG. 30C
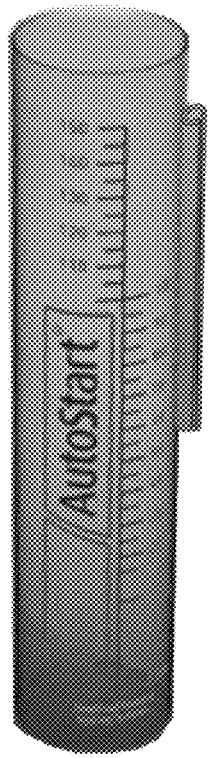
FIG. 30D
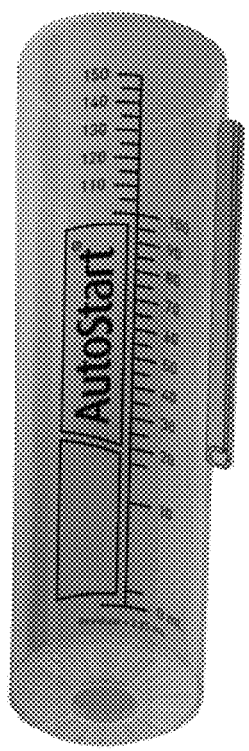
FIG. 30E
FIG. 30G
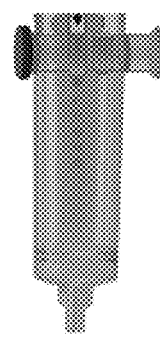
FIG. 30F

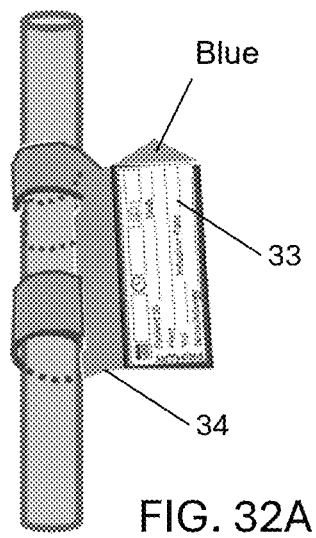
FIG. 32A
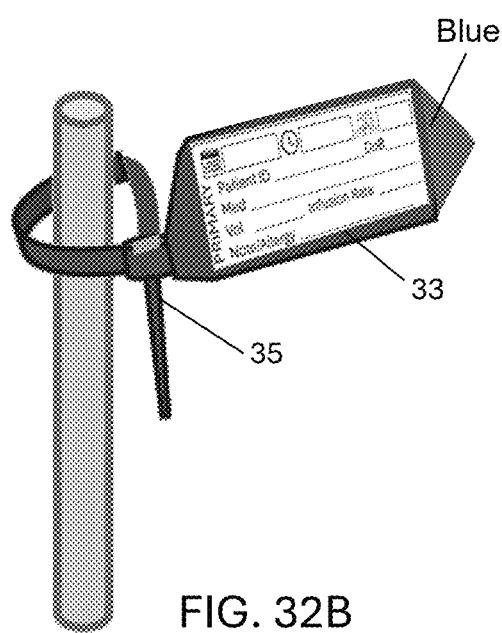
FIG. 32B
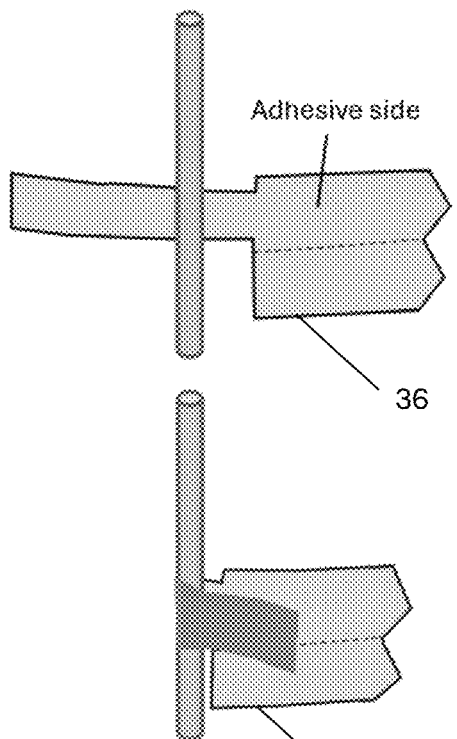
FIG. 32C
FIG. 32D
FIG. 32E
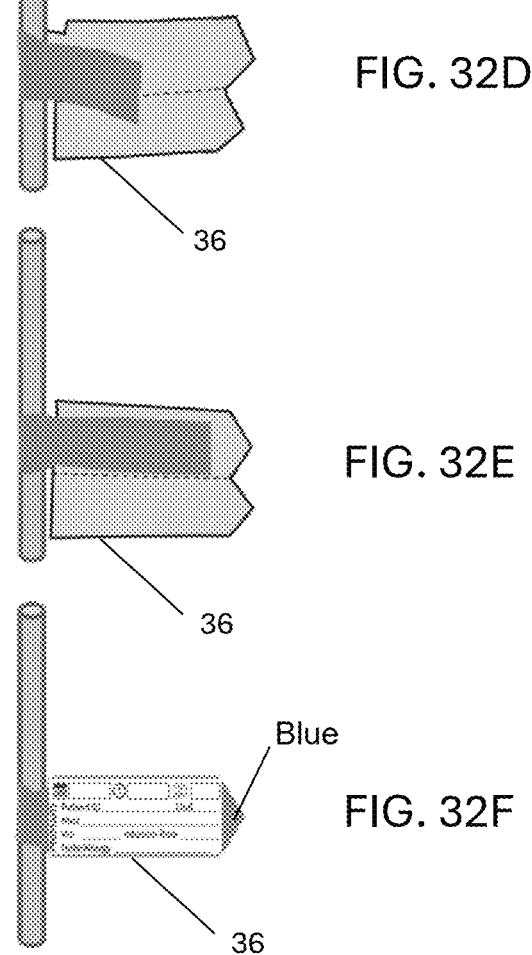
FIG. 32F

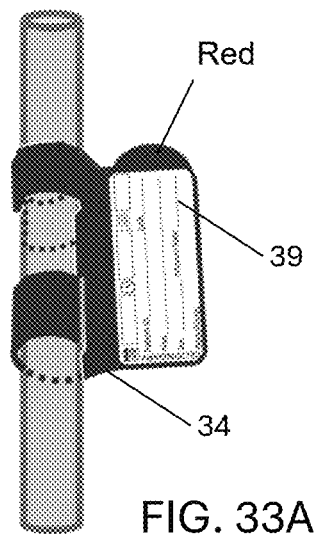
FIG. 33A
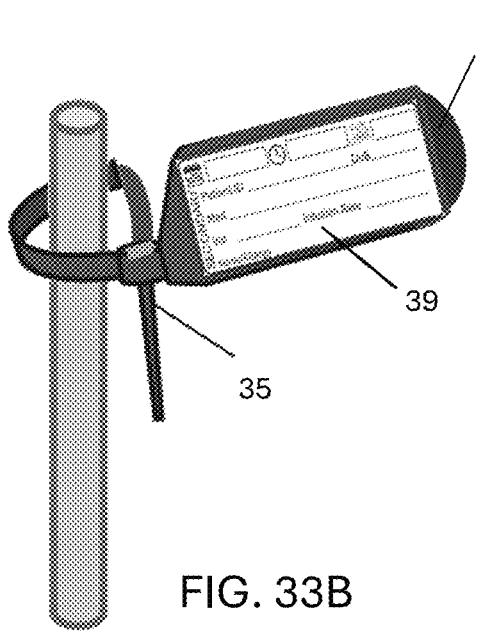
FIG. 33B
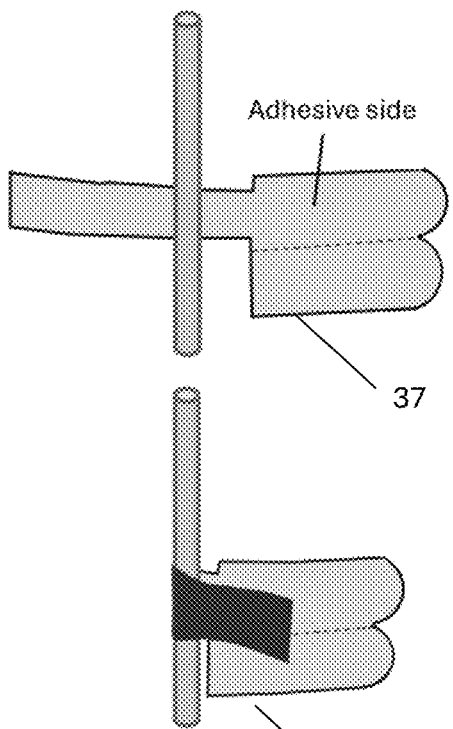
FIG. 33C
FIG. 33D
FIG. 33E
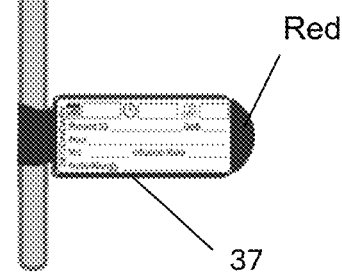
FIG. 33F

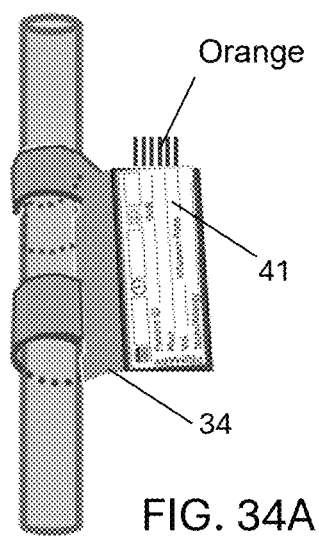
FIG. 34A
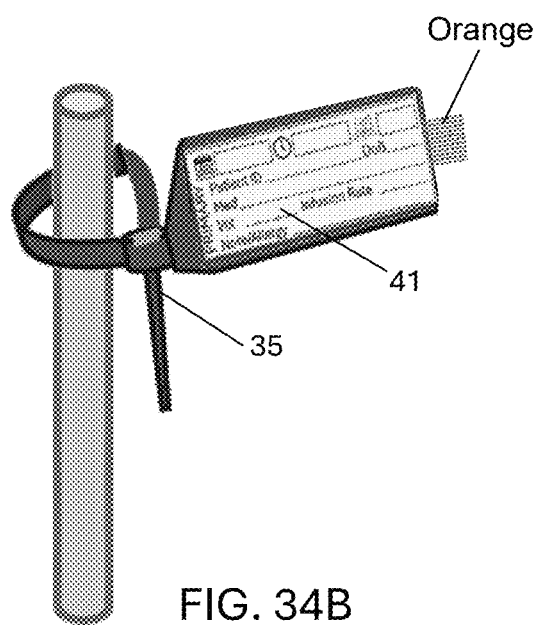
FIG. 34B
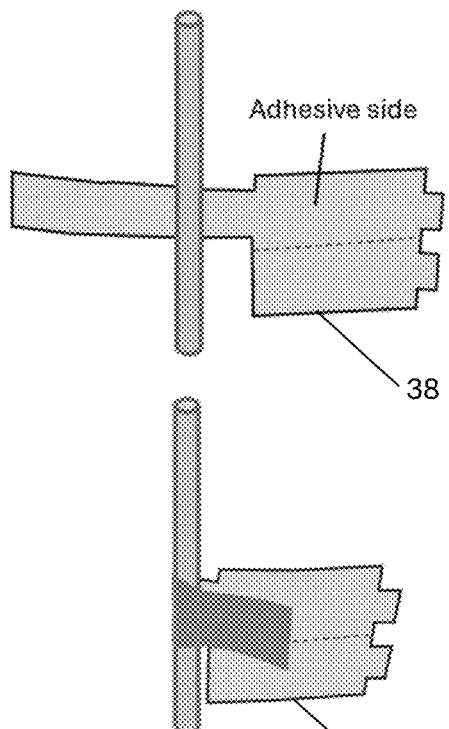
FIG. 34C
FIG. 34D
FIG. 34E
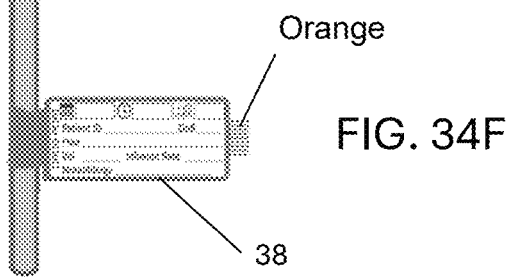
FIG. 34F

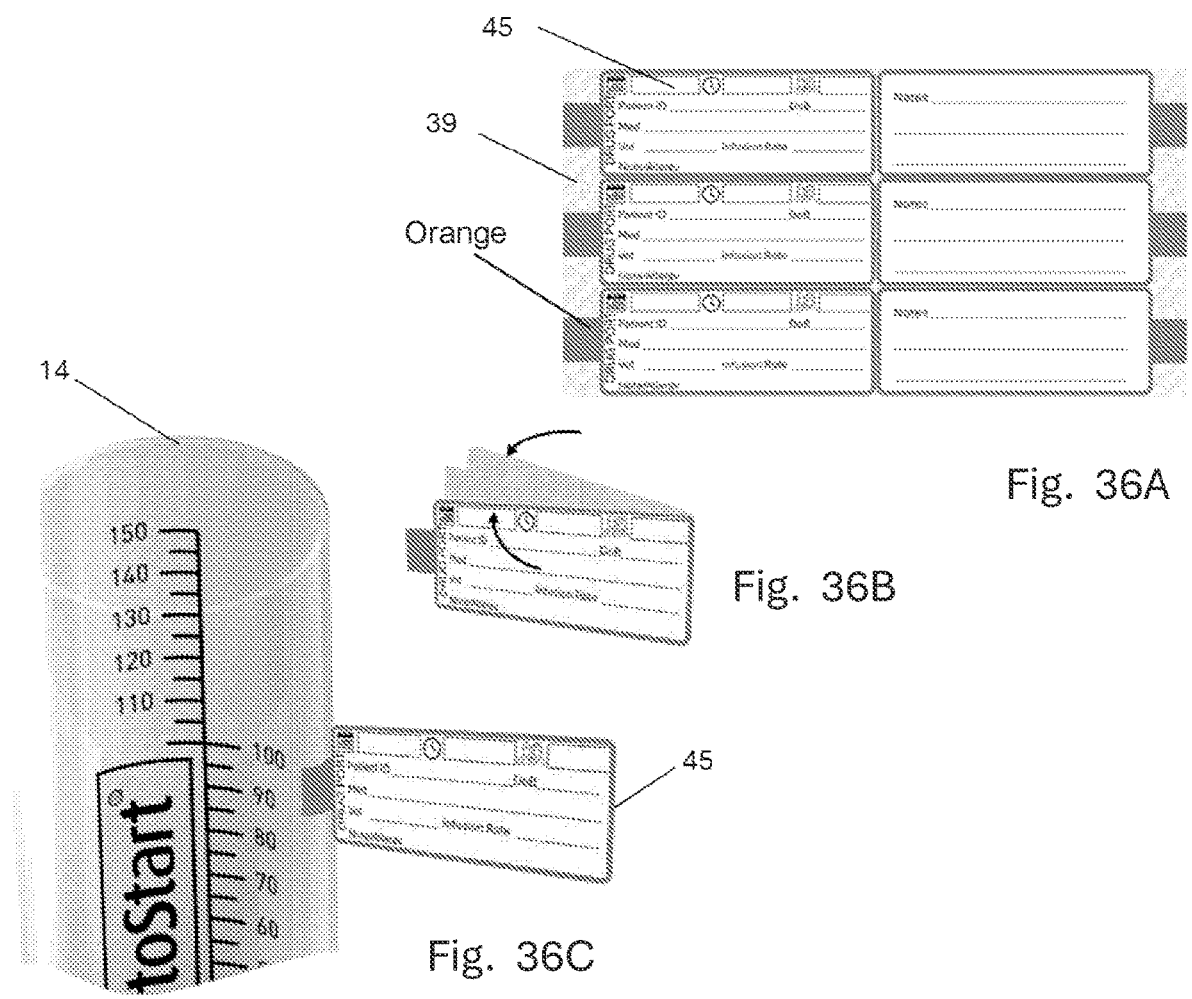
Fig. 36A
Fig. 36B
Fig. 36C
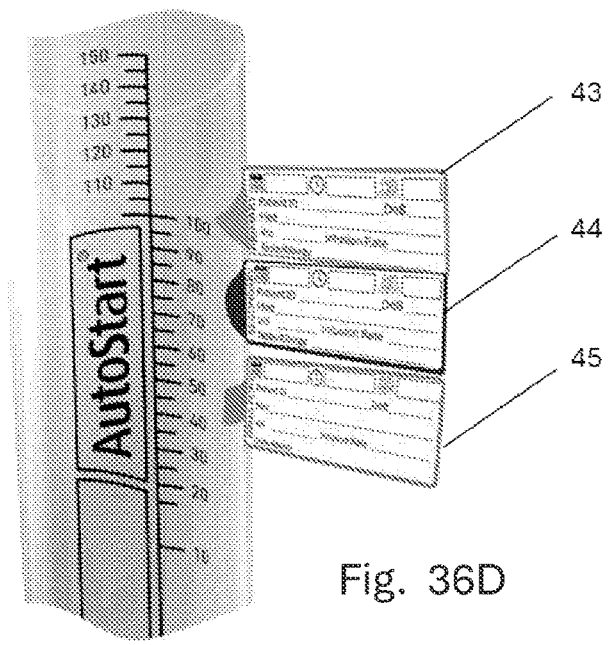
Fig. 36D

GRAVITY-FED BURETTE SYSTEM

FIELD OF THE INVENTION

The present invention relates to infusion systems relying upon gravity for reliable IV fluid delivery across the full range of liquid medical therapies for use in hospital critical care levels down to home care levels.

BACKGROUND OF THE INVENTION

The history of intravenous (IV) fluid burettes traces back to the evolution of intravenous therapy and the need for accurate fluid administration. Burettes have become integral to IV administration sets which include tubing, clamps, connectors, and other components for delivering IV fluids with efficiency in healthcare settings. In recent years, electronic burettes have emerged as an alternative to traditional gravity-based burettes. These pressure-driven systems create a host of problems: lack of standardization for mounting IV tubing into their compression mechanisms, informational displays differ, keypad entry formats vary, programming methods are non-standard, and being electrically powered, they require a backup battery. With necessary software updates, especially to stay ahead of cybersecurity concerns, as well as maintenance for said battery systems and mechanical wear components, the overhead costs stack in addition to the initial capital equipment expenditure. A condition overlooked by caregiver organizations is that electronic pump pulsing creates micro-pistoning of the vein-embedded catheter potentially leading to degradation of vein patency. A further consideration given the repeated compressions on IV tubing by peristaltic pumps is the unwanted generation of microparticles being shed to the IV fluid.

According to "This is The State of Nursing", https://media.nurse.org/docs/State+of+Nursing+-+2022.pdf, over 87% of nurses felt burnt out in 2022, and 80% of nurses say their units are inadequately staffed. Shouldn't medical device manufacturers strive to deliver systems that make caregivers' daily routines simpler, less stressful, and safer for their patients?

Quoting from a study at the University of Sydney titled Errors in the administration of intravenous medications in hospital and the role of correct procedures and nurse experience, https://qualitysafety.bmj.com/content/qhc/20/12/1027.full.pdf:

While infusion pumps have the potential to reduce errors, their effectiveness in everyday practice is often seriously compromised by a failure to use devices as intended, for example by-passing safety features and ignoring alerts. We found a low utilization of pumps especially among less experienced nurses, the group with the highest error rate. However, use of pumps was not associated with reduced errors. The extent to which this was due to incorrect use is unknown.

Few studies have examined the association between nurse experience and intravenous medication errors. We found that as nurses gained experience up to six years, their rates and severity of errors declined significantly. This is an important finding and clearly suggests that inexperienced nurses should be a target for training and supervision with a focus on correct intravenous rates. Han et al . . . found no relationship between experience and intravenous administration errors, but their sample was vastly more experienced (median 18 years) compared with our study (median 6 years)".

Given these risk conditions and costs with electronic burettes, the invention herein revitalizes the use of gravity as the sole physical motive force for a complete range of medical fluid delivery options endeavoring to reduce burdens on the IV infusion caregiver while improving IV fluid delivery for optimum vein patency maintenance.

SUMMARY OF THE INVENTION

The present invention creates a multi-functional platform for gravity-fed burettes to serve the needs for IV infusion with standardization of system setup for simplicity while enhancing safety, especially for handling hazardous liquids. The present invention builds upon the gravity-fed design of U.S. Pat. No. 9,352,080 that describes a medical burette with a buoyant valve control system for starting and stopping liquid flow from an IV bag with the capability for a second drug infusion through a port. This invention establishes an entirely closed IV infusion system for delivering a wide range of medical fluids with an improved flushing system, and caregiver event recording structure. Fully maintained is the vital benefit of the buoyant valve low-fluid level sealing to prevent air bubbles from entering subsequent tubing eliminating the potential for an air embolism.

The improved design of the present invention better manages the three main types of IV infusion. 1) Continuous or intermittent infusion is mainly used with patients suffering fluid/electrolyte imbalances. Here, the primary IV bag is spiked by the primary feed line for volumetric dosing to the burette or set up as a steady flow to the burette effectively stabilizing the static height of the liquid for maximizing the drip rate control. 2) Secondary IV infusion bag, sometimes called an IV piggyback, connects to the dedicated secondary IV bag spike. With the delivery of this feed to the burette, the often-overlooked task of hanging the secondary IV bag higher than the primary IV bag is eliminated. 3) IV push is when a syringe containing medication is connected to an access port sited in the primary tubing so that the medication can be delivered through the port. The syringe plunger should be pushed in slowly to avoid irritating the vein or administering the medication too quickly. Once the medication is in the fluid stream of the IV tubing, it is frequently followed with a second fluid injection, known as a 'flush', to ensure that the total medicinal dose reaches the bloodstream as expected. With this invention, the IV push can be delivered via the drug port as a full dose followed by a syringe flush, both emptying into the burette chamber. In this system of the present invention, the drip rate-controlled delivery system minimizes potential damage to the vein by eliminating high-pressure syringe liquid injection outflowing from the embedded catheter orifice. Ultimately, this invention should reduce the 30-40% failure rate of Peripheral Intravenous Catheters (PIVCs) for several reasons, including occlusion, phlebitis, infiltration, and infection.

Delivering this closed Safer Infusion System able to prevent unintended exposure to hazardous drugs such as antineoplastics is a secondary goal.

Burettes dedicated to IV infusion provide precise fluid measurement through calibration markings on the burette chamber. Once filled to a desired level, the burette chamber provides visual confirmation of fluid administration by observing the fluid level while providing means to adjust the infusion rate as needed for accurate dosing. Drip rate regulation with a single, integral drip chamber provides a numerical indicator of the drip rate, based on the patient's needs and prescribed infusion rate. The float element sealing valve action prevents the infusion of air bubbles into the patient's bloodstream while also acting as a dynamic flow valve for a steady Keep Vein Open (KVO) IV flush. This AutoStart function also prevents over-infusion when a large IV bag is hung. All of these features integrate within the proposed IV administration set safeguarding an accurate rate of fluid delivery to enhance drug effectiveness while ensuring patient safety. Specifically addressed is the genuine need for standardizing the static fluid height to ensure consistency in IV fluid flow rate management down to the vein level. The lack of device provider vision and caregiver comprehension of the importance of static height standardization for gravity feed led to the general perceived need for electronic infusion pumps to drive IV fluids no matter how the IV fluid bags are hung at the bedside.

With a primary, secondary, and tertiary liquid input option, the present invention increases versatility in IV bag setups while making hazardous IV fluid handling more manageable for hospital-to-the-home care with fully closed systems. These benefits are delivered by integrating a Rotary T-valve into the burette top cap as a monoblock system. Three configurations of burette top cap monoblock valves maximize functionality while minimizing size and complexity at a reasonable cost. Additional functionality is delivered with Safer Infusion Systems that accommodate aggressive chemotherapy drugs, some of which are ultraviolet and visible light sensitive requiring specially colored light-blocking materials.

Lastly, a sterile labeling system ensures timely medical documentation and identification of the responsible caregiver assuring high-quality care called for by the "ten rights" of medication administration. These rights have evolved to maximize patient safety while minimizing the risk of medication errors. The ten rights are 1) Right Patient 2) Right Medication 3) Right Dose 4) Right Route 5) Right Time and Frequency 6) Right Education 7) Right Reason 8) Right to Refuse 9) Right Response and 10) Right Documentation.

The present invention relies upon a gravity-fed burette system with a burette chamber accessible by a chamber outlet for delivering liquid from the chamber, a vent port from the chamber, a Primary IV bag inlet into the chamber, and a directed flow inlet into the chamber from a chamber valve. A primary IV bag inlet control valve restricts flow from a Primary IV bag through the Primary IV bag inlet into a central tube operatively associated with a float element sealing valve which includes a float which sits on top of a liquid well located at the bottom of the chamber with the chamber outlet. A chamber valve controls flow of liquid into the chamber via the directed flow inlet. The chamber valve can receive liquid flow from a Primary IV bag branch, a Secondary IV bag inlet from a Secondary IV bag and a drug port inlet. The control valve can be adjusted to allow liquid to flow through the drug port inlet into the chamber or allow liquid to flow from the drug port inlet through the chamber valve into the Secondary IV bag inlet. A single L-Port Rotary valve can be used as the Primary IV bag inlet control valve and a Primary IV bag branch control valve, but the Primary IV bag branch control valve can also be a separate valve, and both the Primary IV bag inlet control valve and the Secondary IV bag inlet control valve can be clamps acting on tubing from their respective IV bags.

Accordingly, it is a primary object of the present invention to provide an improved, and safer, gravity flow system for IV fluid flow.

This and further objects and advantages will be apparent to those skilled in the art in connection with the drawings and the detailed description of the invention set forth below.

BRIEF DESCRIPTION OF THE DRAWINGS

FIG. 5 presents prior art of U.S. Pat. No. 9,353,080 B2 incorporating a single IV bag and accompanying use flow diagram.

FIG. 6A employs an attached Check Valve fed from a Y-adapter, while FIG. 6B fully integrates the Check Valve into the valve body assembly.

FIGS. 8A-D present greater detail on the Burette Top Cap monoblock designs according to the present invention with a Check Valve integrated into a 3-Way Rotary T-valve with an illustration of a drug push from the Drug Port up to a Secondary IV bag.

FIG. 8E is a blow-up showing greater detail from FIG. 8A while

FIG. 29 is a comprehensive list of typically hazardous chemotherapy drugs delivered by IV infusion therapy with ten light-sensitive compounds highlighted.

FIGS. 30A-F show pigment-loaded materials capable of light-blocking to best shield UV and visible light-sensitive liquid medicines. FIG. 30G exemplifies sterile labels included with the hazardous materials kit that can attach to the IV bag and the SIS burette chamber for indication of proper disposal.

FIGS. 32A-F illustrate label set designs for labeling the Primary IV feed to the Safer Infusion System. Fold-over adhesive labels document patient ID, drug type, dose level, date, time, caregiver, notation for allergy issues, etc. provided for use in a sterile environment.

FIGS. 33A-F illustrate label set designs for labeling the Secondary IV feed to the Safer Infusion System.

FIGS. 34A-F illustrate label set designs for labeling the Drug Port feed to the Safer Infusion System.

FIGS. 36A-D illustrate the use of two unbonded tabs, formed like wings, bonding a label to the side of the Burette Chamber.

DETAILED DESCRIPTION OF THE INVENTION

The present invention is directed to a gravity flow system for IV fluid flow, rather than use of an electronic pump to control fluid flow. This avoids creating micro-pistoning of a vein-embedded catheter and protein particle formation associated with electronic pump systems.

Figure 1:
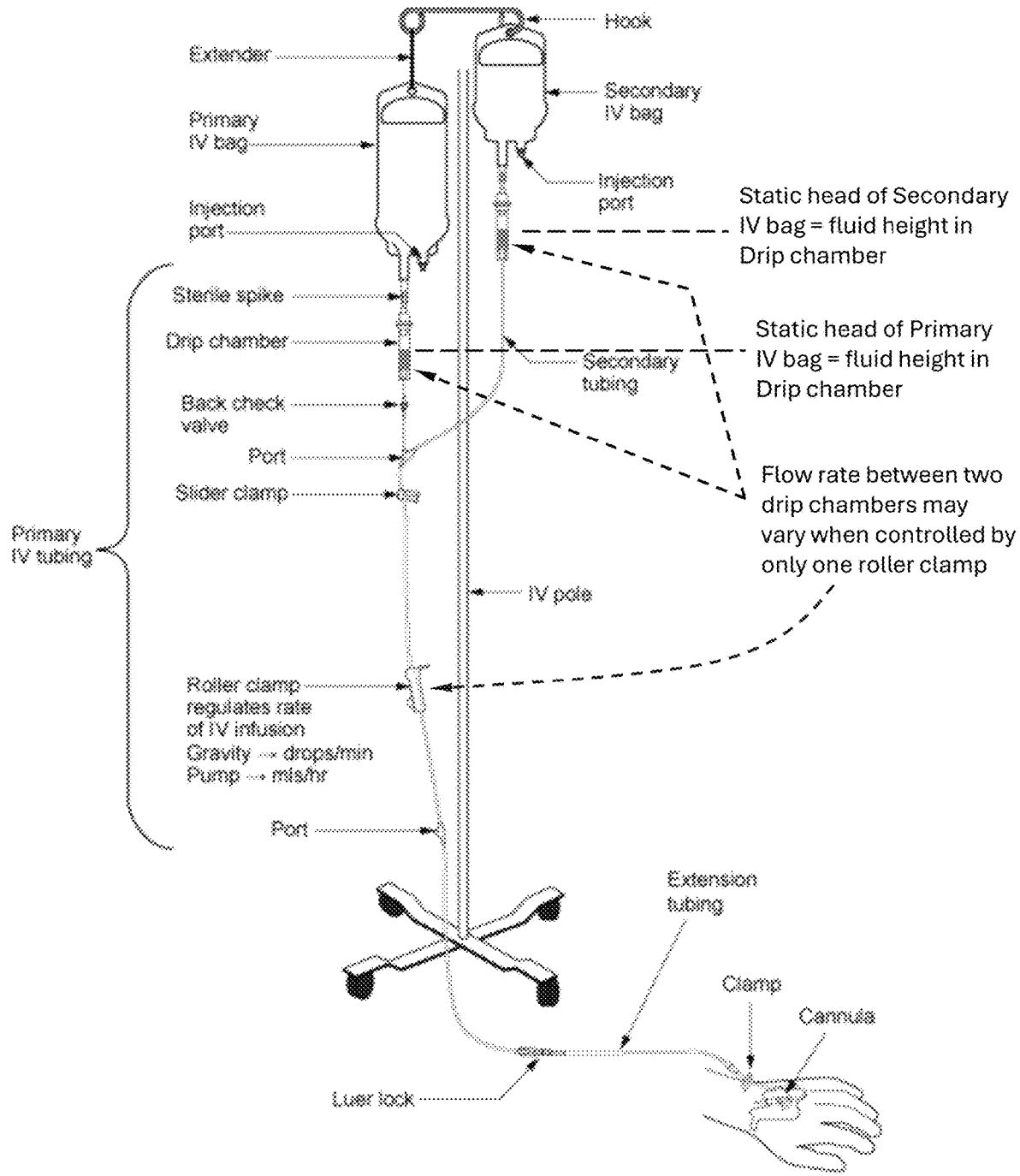
FIG. 1 is a prior art diagram from Doyle, G. R., McCutcheon, J. A. (2015). "Clinical procedures for safer patient care" which illustrates IV primary and secondary tubing setup.

A prior art gravity-fed infusion system is illustrated in FIG. 1 obtained from Clinical Procedures for Safer Patient Care (BC Campus 2015) by Doyle, G. R. and McCutcheon, J. A., published at https://opentextbc.ca/clinicalskills/chapter/8-2-types-of-iv-therapy/. This system arrangement appears to be valid, yet one might criticize this very common diagram layout and labeling as misleading. The larger primary bag is correctly placed on a hanger to lower it below the typically smaller secondary bag. If the secondary bag is not hung higher than the primary bag's liquid level, the secondary liquid flow will not be delivered properly. This diagram exaggerates the static fluid head between the drip chambers below each IV bag compared to the IV cannula resident in the patient's hand at essentially floor level. The static head should be maintained at 18 inches to 24 inches between the liquid level in the lower drip chamber and the infusion site on the patient. Only with consistency of setup will the caregiver develop their efficiency and accuracy in adjusting the roller clamp function as they progress from patient to patient.

The Institute for Safe Medication Practices in Plymouth Meeting, PA recommends that secondary medications be administered via systems that do not require a head-height differential. Despite emphasizing familiarity and simplicity, this suggestion is also included in the latest recommendations issued by the Infusion Nurses Society (Infusion Nurses Society. Infusion therapy standards of practice. 8th ed. Norwood, MA; 2021.)

The Safer Infusion System (SIS) of the present invention answers this issue such that the height of any IV bag does not matter as long as its height is sufficient to provide gravity flow to the SIS Burette Chamber.

U.S. Pat. No. 9,352,080 B2, the disclosure of which is specifically incorporated herein by reference in its entirety, represents a significant improvement to gravity-fed infusion systems. This patent discloses use of a single IV bag (referred to as a "Primary IV bag" in the industry), with an AutoStart fluid control methodology where the Primary IV bag constantly feeds liquid directly to the Central Line (15) of the burette system (see FIG. 2 which is a reproduction of FIG. 3 of U.S. Pat. No. 9,352,080 B2). The heart of the AutoStart as presented in U.S. Pat. No. 9,352,080 B2 automatically restarts flow from the Primary IV bag once a medicated bolus has been delivered to the patient. This AutoStart function saves clinicians time by not requiring their immediate return to the patient to manually restart the flow. When a bolus is delivered in a standard burette, the entire volume is allowed to flow out of the device, except for a tiny amount (~2 m/I) of residual fluid which may be left as part of the shutoff valve operation. Standard IV infusion protocol calls for a following flush with typically 50 mL of fluid to ensure that the full medicinal load is delivered and does not conflict with the next dose. The AutoStart burette has a system of a float (39) and seals (44, 47) which enable a restart of fluid flow from the Primary IV bag before the entire bolus has been delivered. The volume of fluid present in the burette when the AutoStart function reopens the flow from the primary IV bag is approximately 10.8 mL. This restart for flushing is automatic and not dependent on the timely return of the clinician.

This flushing, referred to as "Keep Vein Open" (KVO) protocol, maintains venous access without administering a large volume of fluids. Infusing at a minimal level is typically 30 milliliters per hour (ml/hr) for most adult patients. The rate may vary depending on the patient's condition, age, weight, and specific medical needs. For pediatric patients or patients with specific conditions, the KVO rate may be adjusted accordingly.

The formula to calculate the KVO drip rate for 30 mL/hr in drops per minute (gtt/min) is:

Drip rate(gtt/min) =

$$\left(\frac{\text{Volume to be infused (mL/hr)}}{60 \text{ (min/hr)}}\right) \times \text{Drop factor (gtt/mL)}$$

For a Micro Drip Chamber (60 gtt/mL):

$$\text{Drip rate} = \left(\frac{30 \text{ mL/hr}}{60 \text{ min/hr}}\right) \times 60 \text{ gtt/mL}$$

Drip rate = (0.5 mL/min) × 60 gtt/mL

Drip rate = 30 gtt/min

For a Macro Drip Chamber (10 gtt/mL)

$$\text{Drip rate} = \left(\frac{30 \text{ mL/hr}}{80 \text{ min/hr}}\right) \times 10 \text{ gtt/mL}$$

Drip rate = (0.5 mL/min) × 10 gtt/mL

Drip rate = 5 gtt/min

Therefore, the roller clamp setting on the Primary IV bag should always allow at least the above flow rates into the Burette Chamber to support the 30 ml/hr KVO protocol.

Spike and Tube Clamp Optimization of the Present Invention

Figure 3:
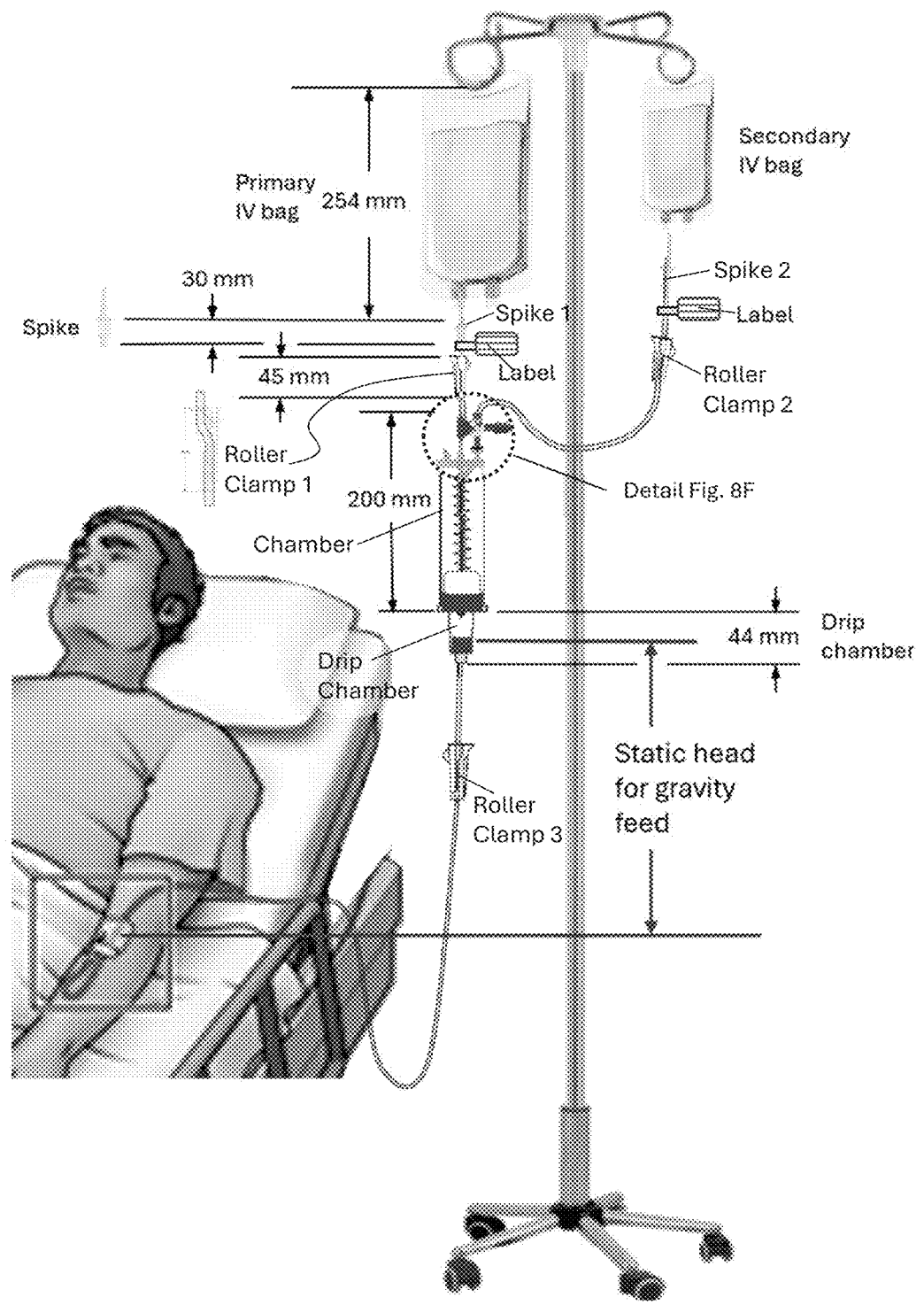
FIG. 3 provides the typical setup for the Safer Infusion System of the present invention with both Primary IV and Secondary IV bags hung at a patient's bedside emphasizing the drip chamber fluid height as a focal point for the static head height in relation to the patient's IV site.

The present invention incorporates several peripheral fluid handling elements into a standardized platform in conjunction with the AutoStart function, enhancing the flush capability of all peripheral components to assure full drug delivery with minimal lag time and dead volume of fluid. Without going into detail about the integrated Burette Top Cap Monoblock design of the present invention (which is discussed later), FIG. 3 illustrates the height considerations necessary to ensure that the safer IV infusion system of the present invention hung from a standard IV pole being of total minimized height ensures maintenance of the critical 18" (458 mm) to 24" (610 mm) static head above the patient's IV site for consistent gravity feed with the largest IV bag (1 liter):

IV bag + Spike + Roller clamp +

Tubing + SIS Burette + Static Height above Patient +

Patient IV site (Bed + Body) = Minimum Hang Height 254 mm + 30 mm + 45 mm + 50 mm + 244 mm + 458 mm + 762 mm =

1,843 mm = 73" = 6' IV poles range from 6 to 7.5 feet

The spike elements access either a fluid bag or bottle. The spikes incorporate helpful features like a finger grip and flat wing(s) providing a grip surface and a surface to press towards the fluid container for connecting to the bag or bottle port. An ideal height of the spike will add only 30 mm to the stack height.

Next in the flow stream is the preferred roller clamp or a pinch clip clamp. In our idealized system, the shortest-height roller clamp that provides adequate grip for one-handed operation is approximately 45 mm in height. With an SIS Burette at approximately 244 mm in total height, this supports system operation with a 6' IV pole. The Primary IV bag length might be shorter with a volume of less than 1 liter or the IV pole may be taller or extended, increasing the Static Height closer to the 24"(610 mm) upper range.

Figure 4:
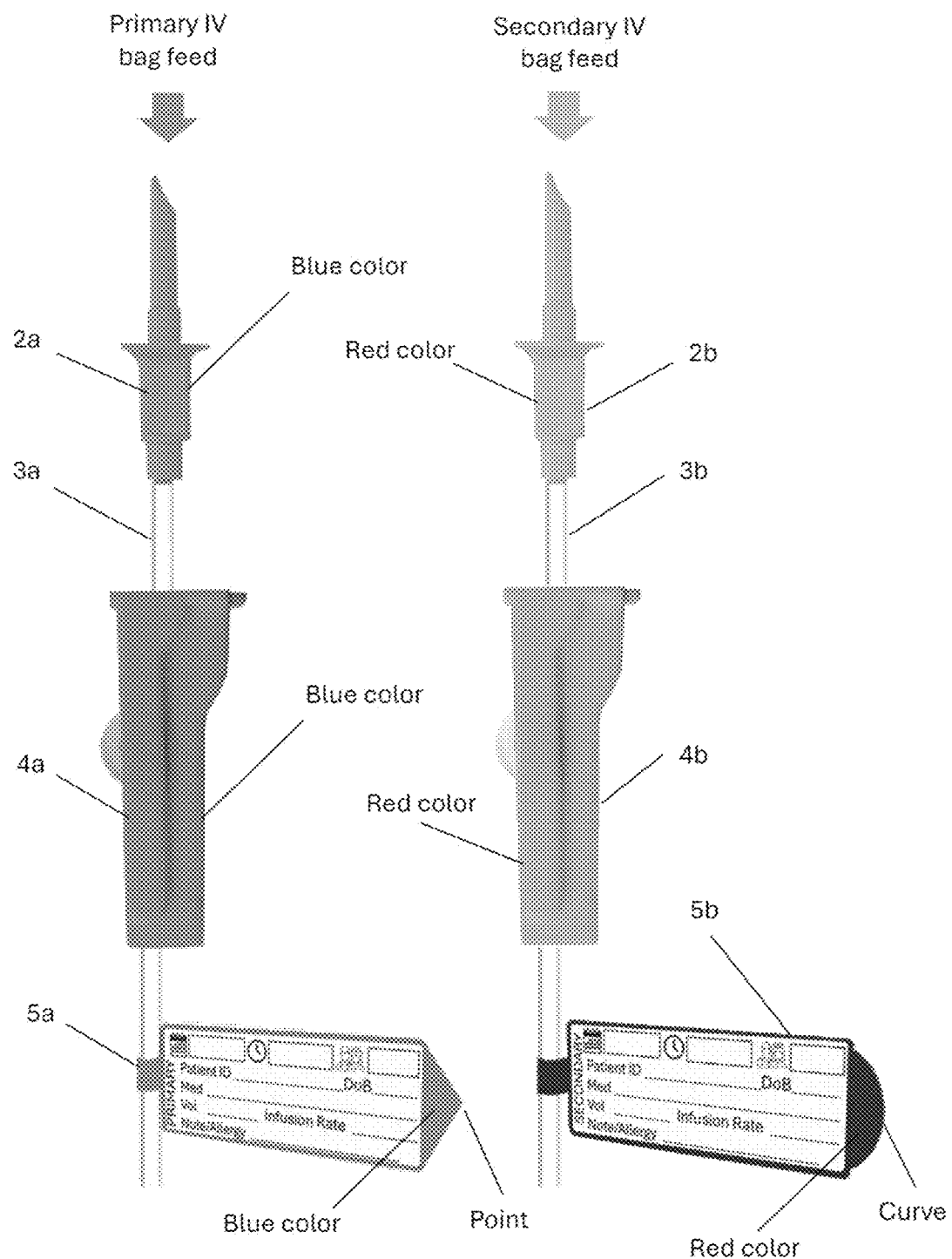
FIG. 4 illustrates the systematic approach to the Primary and Secondary IV bag connection with respect to hardware colors and label locations.

FIG. 4 highlights a coding system implemented with the SIS setup. The Primary IV bag Spike (2a), Roller clamp (4a), and later applied process label (Sa) are one color, chosen here as blue. The Secondary IV bag Spike (2b), Roller clamp (4b), and later applied process label (5b) are another color, chosen here as red. An additional coding shape for the process label has a point for the Primary IV label (Sa) and a curve for the Secondary IV label (5b).

When the roller clamp is open, the primary bag fluid stream drops into the Central line of the Safer Infusion System burette that performs a unique function described in U.S. Pat. No. 9,352,080 B2 where the burette body contains a float valve regulating liquid level within the chamber by engaging an inlet passage on an outlet tube. The primary flow stream travels inside of the Central Tube being dispensed onto the float. In this invention, in addition to the Drug Port provisioned with a needleless connector, another input is made standard on the Burette Top Cap Monoblock for a feed from a Secondary IV bag by way of an integrated valve body. Thus, a closed system is always available whether a Primary IV bag, a Secondary IV bag, or a syringe-introduced medicinal load is required for patient care. IV documentation labels are placed in highly visible positions below each IV bag.

To best compare the prior art of FIG. 5 to the set of inventions here, we see only provision for a single Primary IV bag. The AutoStart feature of FIG. 5 employs a second tap from the single spike "B", indicated by the tubing with Bypass clamp "C". This second feed facilitates bulk filling of the burette with a specific fluid volume. Comparing FIG.

Figure 6A:
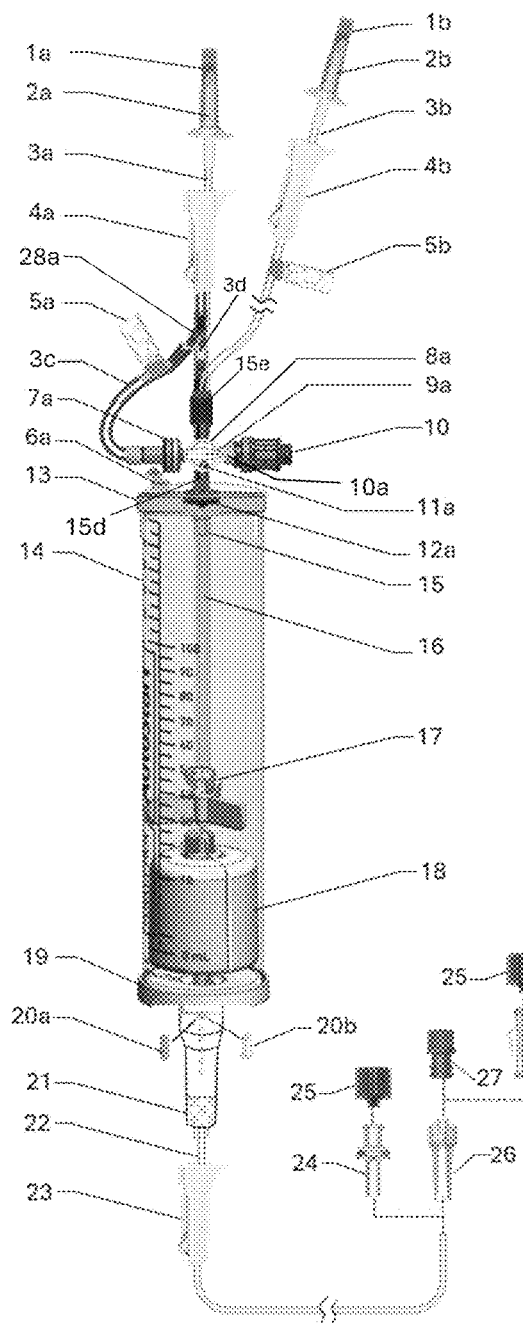
FIGS. 6A-B are two versions of the closed Safer Infusion System and their components. The Safer Infusion System is a closed system.
Figure 6B:
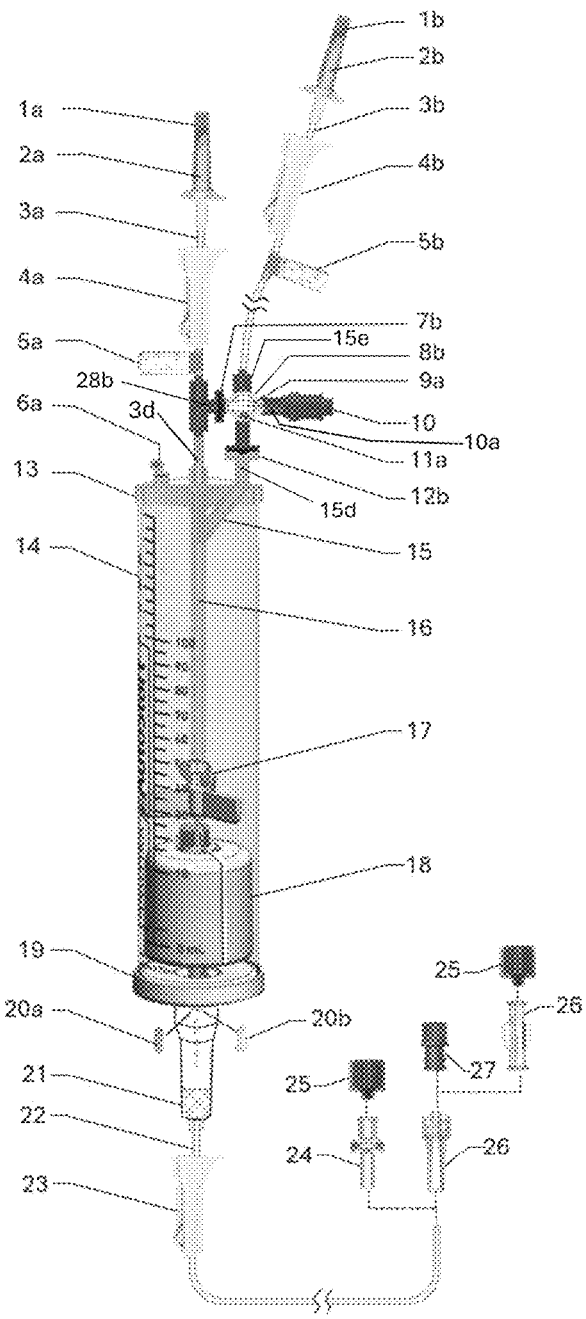

5 to FIGS. 6A-B, as standard, we see a provision for incorporating a Secondary IV bag plus the Drug Port needleless connector (10).

Whereas FIG. 5 presents a spike port option (H), FIGS. 6A-B present SIS outlet options of a Female Luer (24) with a Male Cap (25) or a Male Luer (26) to which a Female Cap (27) can be attached. A Female-to-Female Adapter (26) can be installed with a Male Cap (25). With this latter configuration, end-users connect with a Female Connector or a Male Connector, whichever is standard with their preferred needle/catheter infusion site assembly. This design eliminates a second spike component as called for in the prior art of FIG. 5 with its Spike Port "H" that is often combined with a drip chamber, in turn, requiring a flow controller roller clamp. Eliminating this doubling of components helps to ensure that with a standard IV pole, a Static Head of 18" to 24" above the patient's IV infusion site is maintained.

Flushing Advantages of the Safer Infusion System of the Present Invention

Flushing in IV infusions is important for many reasons and is why the SIS incorporates the capacity for flushing both the Secondary IV bag as well as the Drug Port.

Drug compatibility is a major concern. Some medications may interact adversely with residual traces of other drugs or fluids present in the IV tubing or bag. Flushing helps ensure the patient receives the intended medication without contamination or dilution from previous infusions. Precision dosing is another area where flushing helps ensure accurate delivery of the prescribed amount of medication to the patient. Residual drug left in the IV tubing or bag could lead to underdosing or overdosing, particularly for potent or narrow therapeutic index medications. Minimizing residual effects is achieved with flushing medications from previous infusions, especially if they have long half-lives or prolonged pharmacological effects. The capability for flushing of the Secondary IV bag can reduce drug waste by ensuring that the maximum amount of medication is delivered to the patient. Flushing helps prevent contamination of IV tubing and infusion sets, reducing the risk of infection or other complications associated with residual drug or fluid buildup. As mentioned above, all of these flushing requirements should be conducted with utmost consideration for maintaining the patency of the infusion site.

Figure 7:
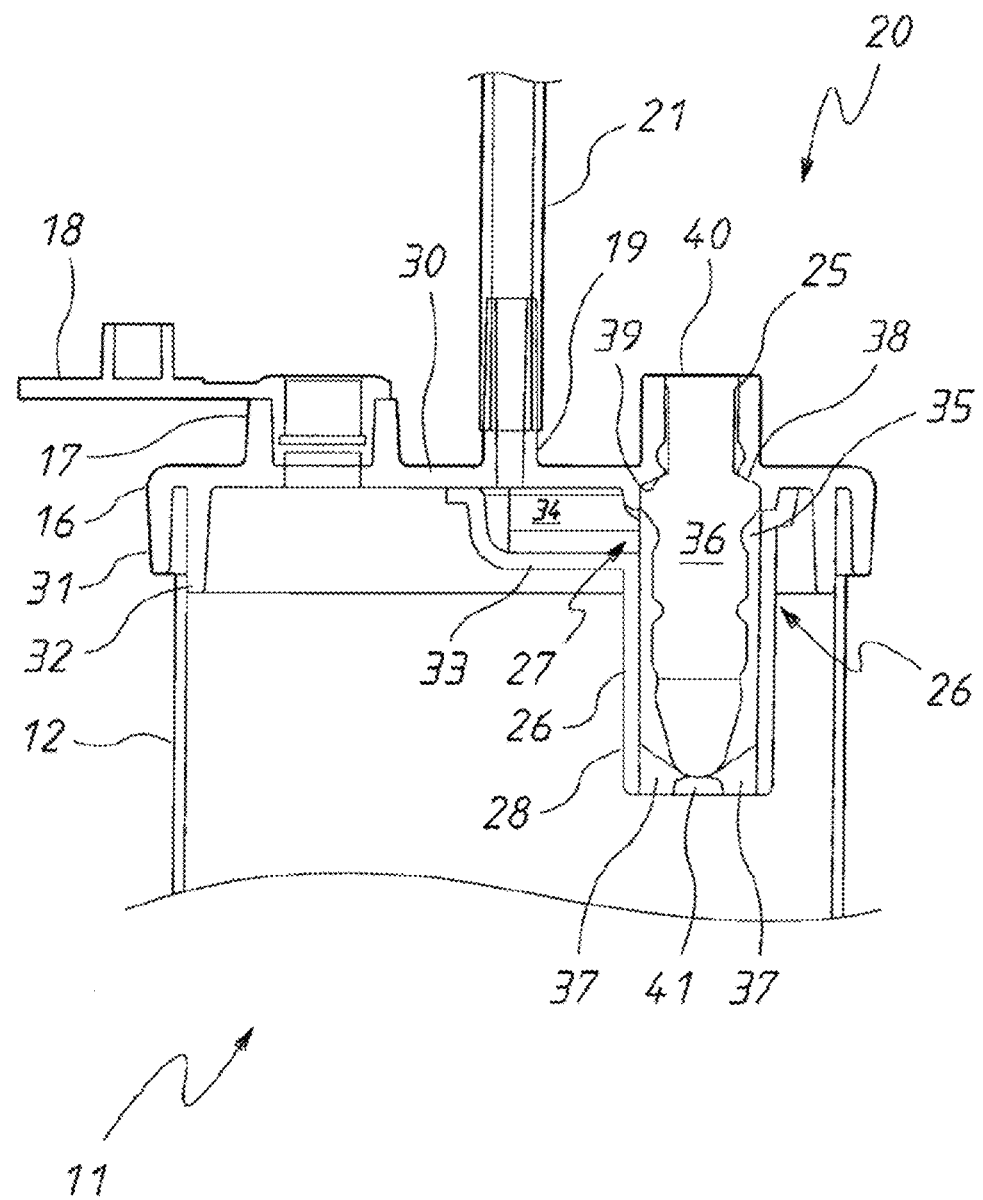
FIG. 7 is a reproduction of FIG. 7 from prior art U.S. Pat. No. 9,199,029B2 which illustrates a flushable injection port.

The SIS supports a wider range of flushing modes than first introduced in U.S. Pat. No. 9,199,029B2 where a provision of a duct from the first inlet (34), prior art FIG. 7, provides a passage to a second inlet (28) of the injection port (20) in the burette top cap allowing flush from the Primary IV bag to flow past the Needleless connector structure. With a syringe installed on port (20), the resilient structure (36) is deformed, allowing flush to be withdrawn up into the syringe and subsequently expelled into the burette chamber. With this prior art, the single moveable closure member is this resilient deformable structure (36). The invention herein enables a wider range of flush capabilities through several Rotary T-valve implementations.

Burette Top Cap Valve Monoblock Designs of the Present Invention

Shown in FIGS. 6A-B are two sets of Spikes (2a and 2b) with Protective Caps (1a and 1b) connected to Tubing (3a and 3b) followed by Roller Clamps (4a and 4b). FIG. 6A features a Y-fitting (28a) connecting Tubing (3c) to Check Valve (7a) which is part of the Monoblock Rotary T-Valve Assembly (8a). Tubing 3d connects to the top of the Monoblock Valve Assembly and on the right side is the Needleless Connector Drug Port (10). FIG. 6B fully incorporates the Check Valve (7b) into the Monoblock Rotary T-Valve assembly 8b. A Check Valve (12a or 12b) may or may not be incorporated into the Burette Top Cap assembly. Below the Rotary T-Valve feed into the Burette Chamber is Directed Flow Tube 15 that sends fluid down the outside of the Central Tube 16. Alignment Piece (17) is attached to the end of the Central Tube (16) and the precision nozzle of the Alignment Pieces interfaces with an Elastomer Seal in the top of the Float (18). Burette Bottom Cap (19) has a similar precision nozzle that interfaces with an Elastomer Seal on the bottom of the Float (18). Attached to the Burette Bottom Cap are Drip Nozzle options: Micro Drip (20a) and Macro Drip (20b). The Drip Chamber (21) attaches to the Burette Bottom Cap. On Tube (22) is the Roller Clamp (23) that controls the drip rate. Following the Roller Clamp (23) are tubing connection options: Female Luer (24) with Male Cap (25), Male Luer (26) with Female Cap (27) and Female to Female Adapter (26) to Male Cap (25).

In FIGS. 8A and 8B, details of the T-Valve Knob (9a) of the present invention are shown. Behind the T-Valve Knob (9a) is the Position Indicator (11a). Air Vent (6a) provides venting for the Burette Chamber (14). FIG. 8C shows an Air Vent having a larger filter (6b) for use with hazardous fluids. The Monoblock Rotary T-Valve Assembly may take different configurations such as having the Needleless Connector Drug Port 10 at an elevated angle for ease of syringe fluid administration. As presented in FIG. 8D, a syringe is pushing its drug load up to the Secondary IV bag. The control positions of the Monoblock Valve Assemblies of FIGS. 6A and 6B are illustrated in FIG. 9. The Rotary T-Valve Knob sits over a Window Plate that when rotated reveals a position indicator icon on the Marker Plate. A design element of the T-Valve body may incorporate a physical position indicator in addition to this visual position indicator. The physical indicator may be by way of a detent verifying that the valve body is correctly aligned for proper fluid flow, and upon reaching this detent, a physical confirmation of seating on the notch would translate to a small vibrational confirmation to the valve operator. With the T-Valve Knob pointing West, a Burette fill operation can be accomplished as well as a Drug Port flush involving a pull of flush from the Primary IV bag, followed by a turn to the South where the flush can be injected into the Burette Chamber. In the North positions, the T-Valve Knob enables a direct flow from the Secondary IV bag to the Burette Chamber with the Check Valve preventing flow to the Primary IV bag line. In the East position for the T-Valve Knob, a syringe connected to the Needleless Connector Drug Port can push its medicine up to the Secondary IV bag, followed by a Knob turn West to pull a flush, and then another Knob turn to the East to push the flush up to the Secondary IV Bag or a Knob turn to the South to push the flush into the Burette Chamber.

Figure 8E:
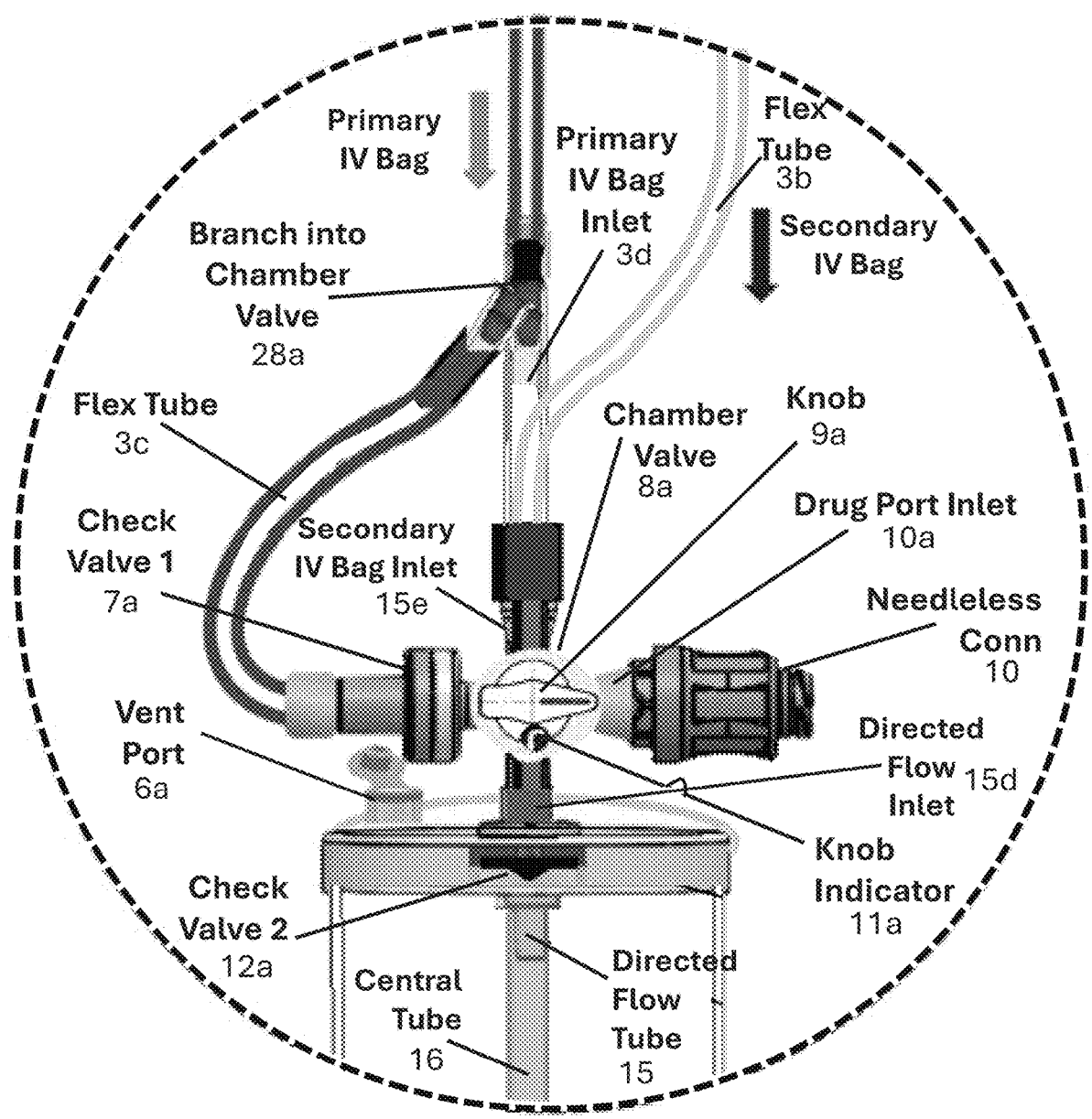
Figure 8F:
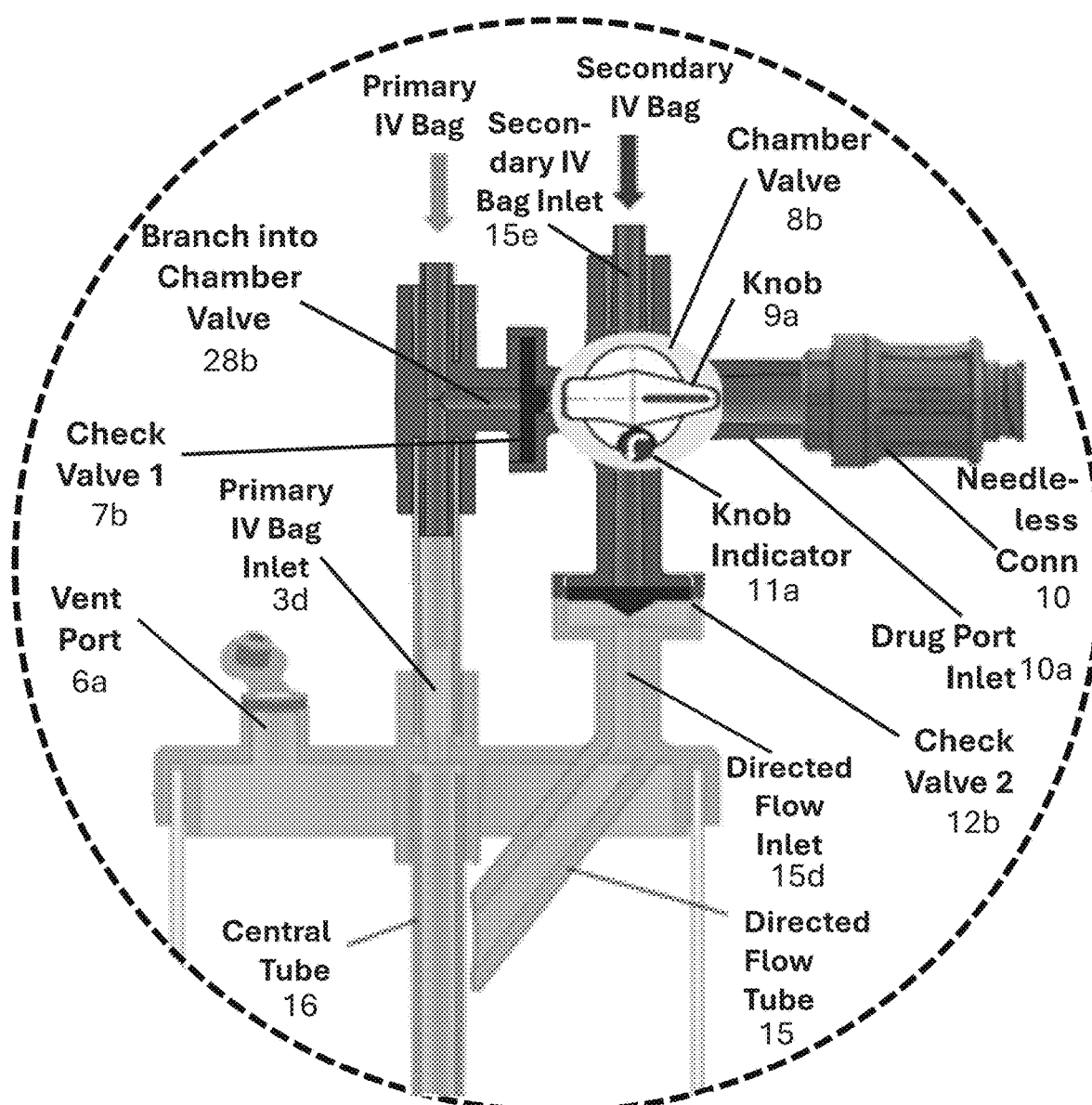
FIG. 8F is a blow-up showing greater detail from FIG. 8B.
Figure 9:
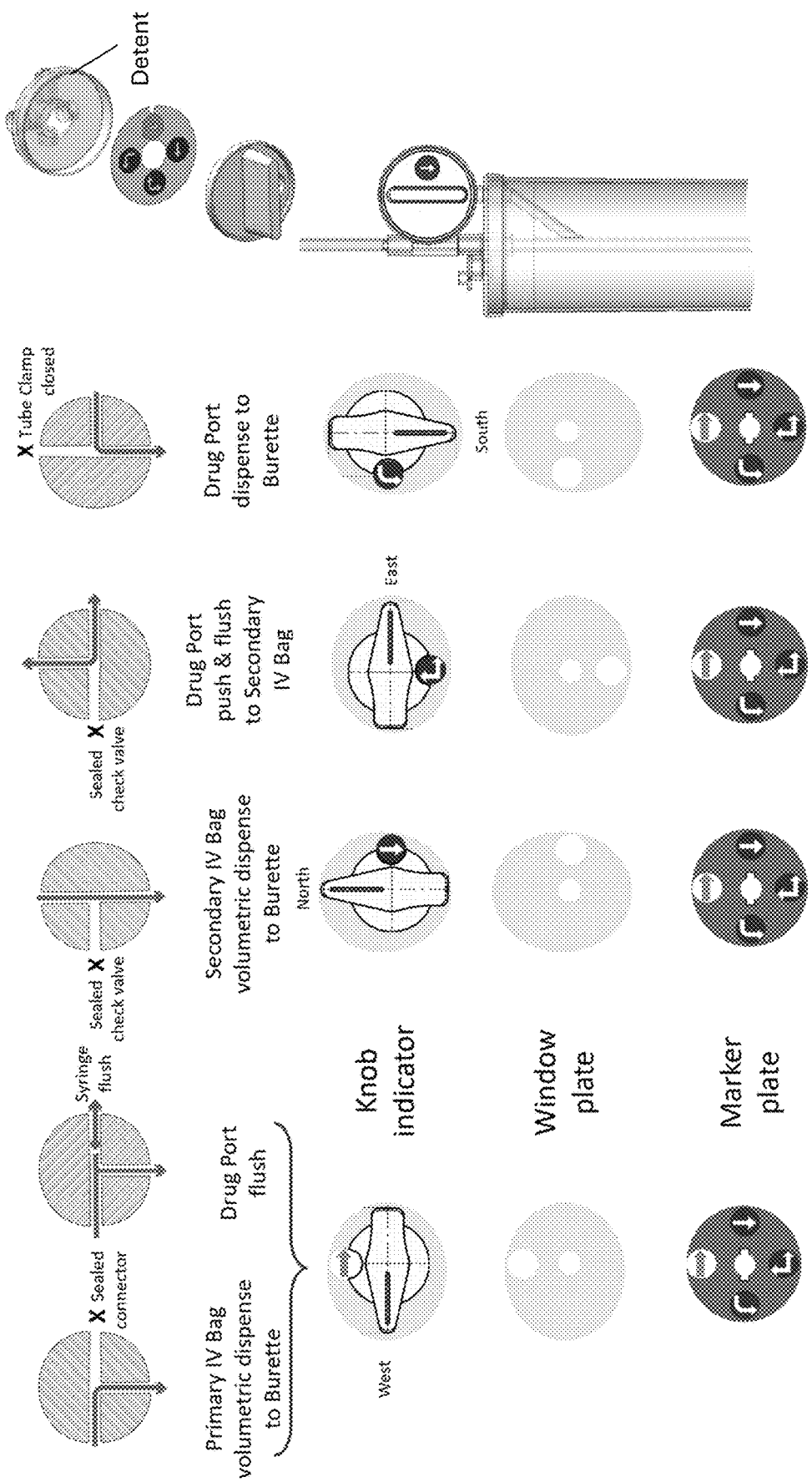
FIG. 9 illustrates Rotary T-valve flow patterns enabled by the Burette Top Cap monoblock design in FIGS. 8A-C. Indicator knob positions rotate with a Window plate that reveals four different indicator icons representing the valve state.
Figure 28A:
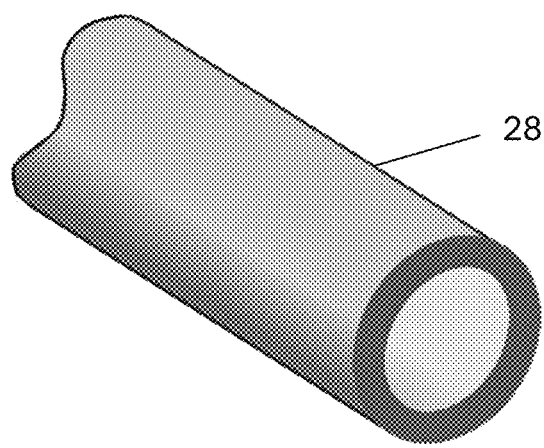
FIGS. 28A-C detail a single wall, double wall, and triple wall construction of flexible IV tubing
Figure 28B:
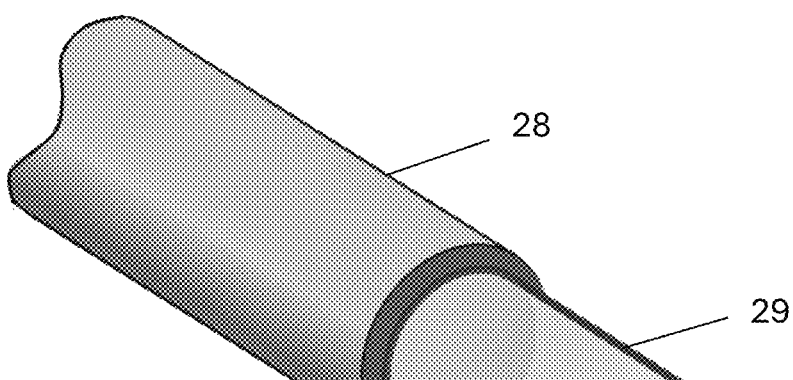

FIGS. 8E and 8F provide blow-ups showing even greater detail of areas shown in FIGS. 8A and 8B, respectively. In both FIGS. 8E and 8F, a hollow body chamber 14 has three entrance points at its top surface—a vent port (6a), a Primary Bag Inlet (3d) and a directed flow inlet 15d into the chamber from a chamber valve (either 8a in FIG. 6A or 8b in FIG. 8F). A Primary IV bag inlet control valve (4a shown in FIGS. 6A and 6B) is operatively associated with Primary Bag Inlet 3d to restrict flow from Primary IV bag Inlet 3d into chamber 14. A Primary IV bag branch (3c in FIG. 8E or 28b in FIG. 8F) into the chamber valve is controlled by a Primary IV bag branch control valve (Check Valve 1 (7a in FIG. 8E or 7b in FIG. 8F)) to allow liquid to flow from the Primary IV bag branch through the chamber valve into the chamber. A Secondary IV bag inlet 15e into the chamber valve is controlled by a Secondary IV bag inlet control valve (4b in FIGS. 6A and 6B) operatively associated with the Secondary IV bag inlet to allow liquid to flow from the Secondary IV bag inlet through the chamber valve into the chamber. A drug port inlet 10a also flows into the chamber valve. The chamber valve allows liquid to flow through drug port inlet 10a into chamber 14 in a first configuration and allows liquid to flow from drug port inlet 10a through the chamber valve into the Secondary IV bag inlet in a second configuration.

Figure 10:
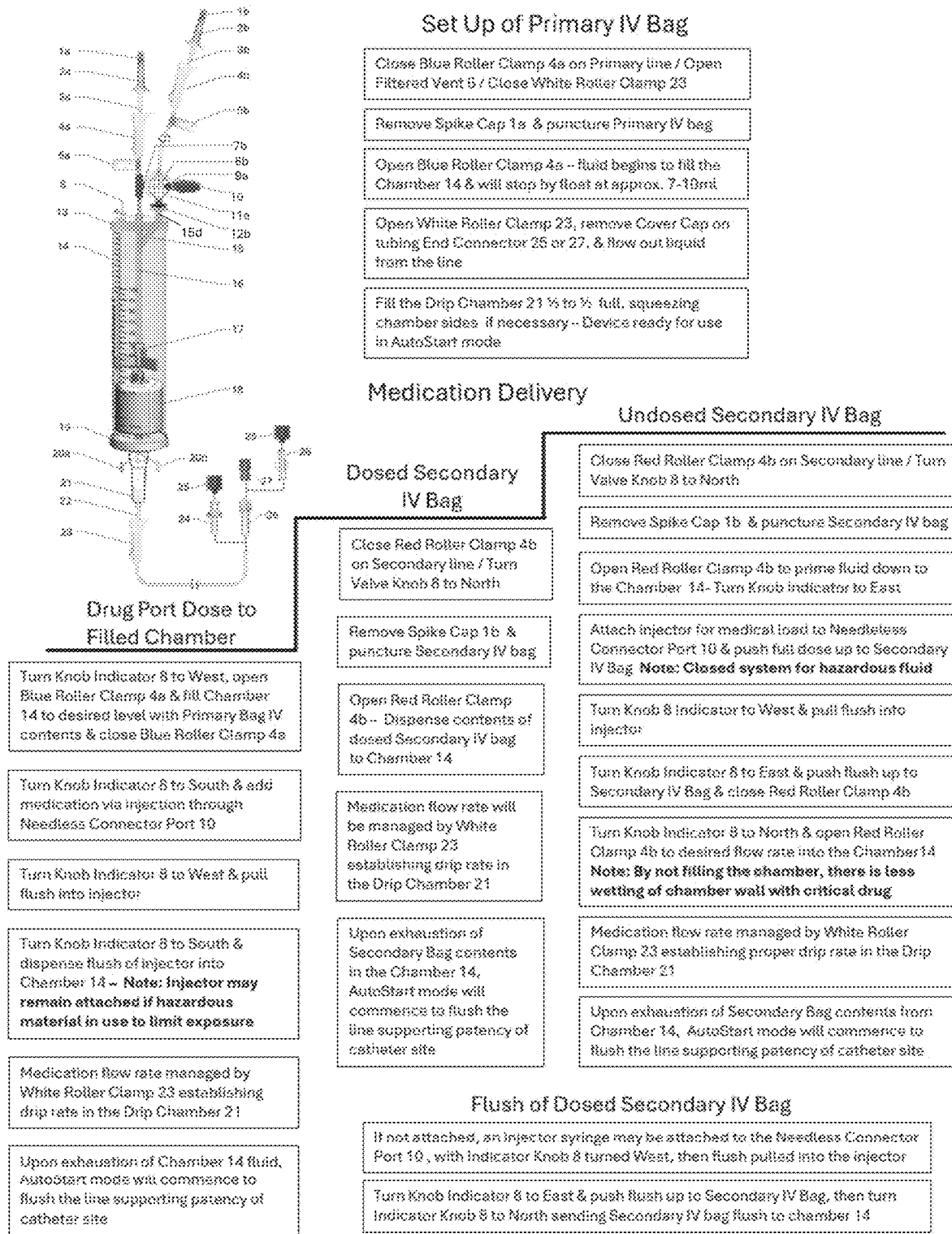
FIG. 10 illustrates the Safer Infusion System with integrated valve configuration presented in FIGS. 8A-C with a Primary IV bag followed by three medical dosing and flushing options.

The flow chart in FIG. 10 details the setup of the Primary IV Bag of the present invention. Follow-on patient dosing options are then listed for 1) A Drug Port dose to the filled Burette Chamber, 2) Dose dispensing from the Secondary IV bag, and 3) Working with an undosed Secondary IV bag that is dosed from the Drug Port such as would be with a hazardous drug. Typically, a syringe bearing a hazardous drug has special latching features to the Needleless Connector Drug Port like that of the B. Braun OnGuard™, Simplivia Chemfort™, Becton Dickinson PhaSeal™, ICU Medical ChemoLock™, and Vigon Qimono™ interfaces. In this way, the Safer Infusion System maintains an entirely closed system with the dosing syringe readily flushed guaranteeing a full delivery of its hazardous contents up to the Secondary IV bag. Lastly, in FIG. 10, the process to flush the dosed Secondary IV bag is described. This important step ensures that the patient receives their full prescribed dose. Historically, some pharmacies prepare their medications with a slightly greater drug concentration knowing that there is typically a residual left in the Secondary IV bag. This overdosing not only leads to a waste of potentially costly drug but also allows for variation in what is ultimately delivered. The best outcome is achieved through precision drug preparation, and controlled delivery, followed by an adequate flush of the Secondary IV bag for consistency of the infusion operation.

The increasing use of small-volume infusions emphasizes the potential clinical impact of drug loss during administration. Small-volume infusions, defined as those being less than or equal to 50 mL in total volume, carry a risk of significant drug loss in the secondary administration set retaining as much as 7 ml of drug volume or 14% of a 50-ml original dose.

When considering minimum inhibitory concentration (MIC) dependent medications, medications with narrow therapeutic index, and medications given in the curative setting, the potential for clinical impact is concerning, especially in the setting of small-volume infusions. The Oncology Nursing Society (ONS) recognizes the underdosing of chemotherapy as a type of medication error, and the Infusion Nurses Society (INS) states that the standardization of drug administration is a recommended strategy to minimize the risk of errors. Unfortunately, neither the ONS chemotherapy/biotherapy guidelines nor the INS's Infusion Therapy Standards of Practice address potential drug loss in IV administration sets or recommend a standard administration technique.

The Safer Infusion System of the present invention will positively impact the ability to create standardization for flush techniques as a Primary IV bag is typically always present providing flush solution. Standardization of optimum flush volumes is a must for good clinical practice guidelines.

Figure 11A:
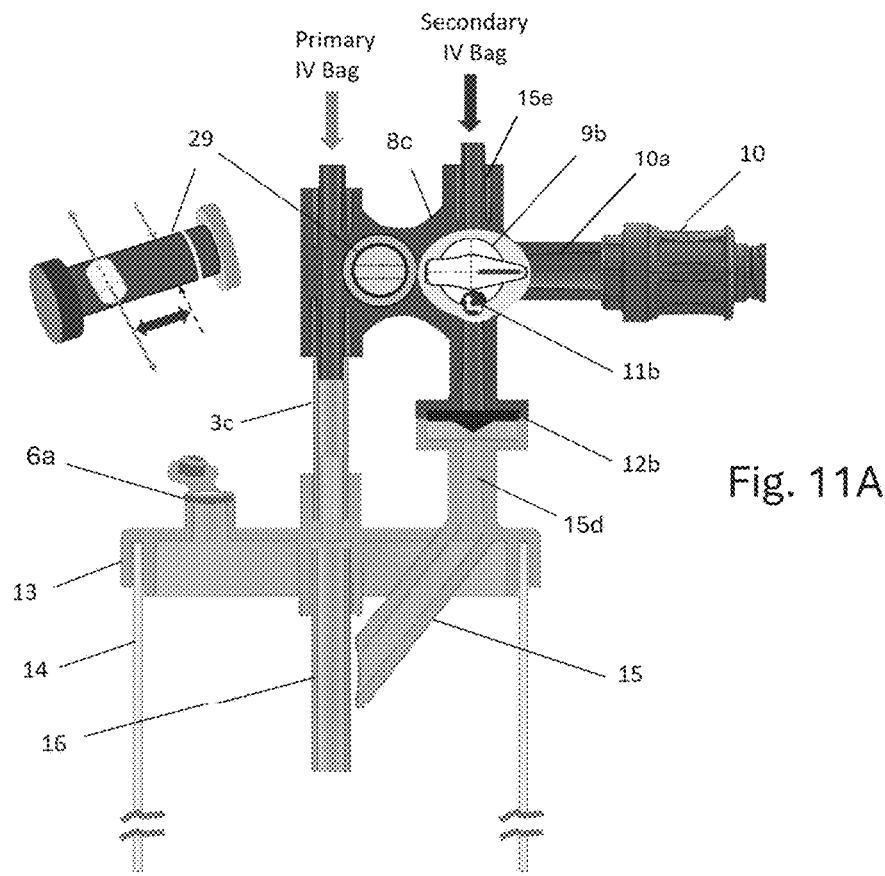
FIGS. 11A-B illustrate a Burette Top Cap monoblock design integrating an On/Off Toggle Valve with a 3-Way Rotary T-valve and Check Valve controlling fluids delivered into the Burette Chamber.
Figure 11B:
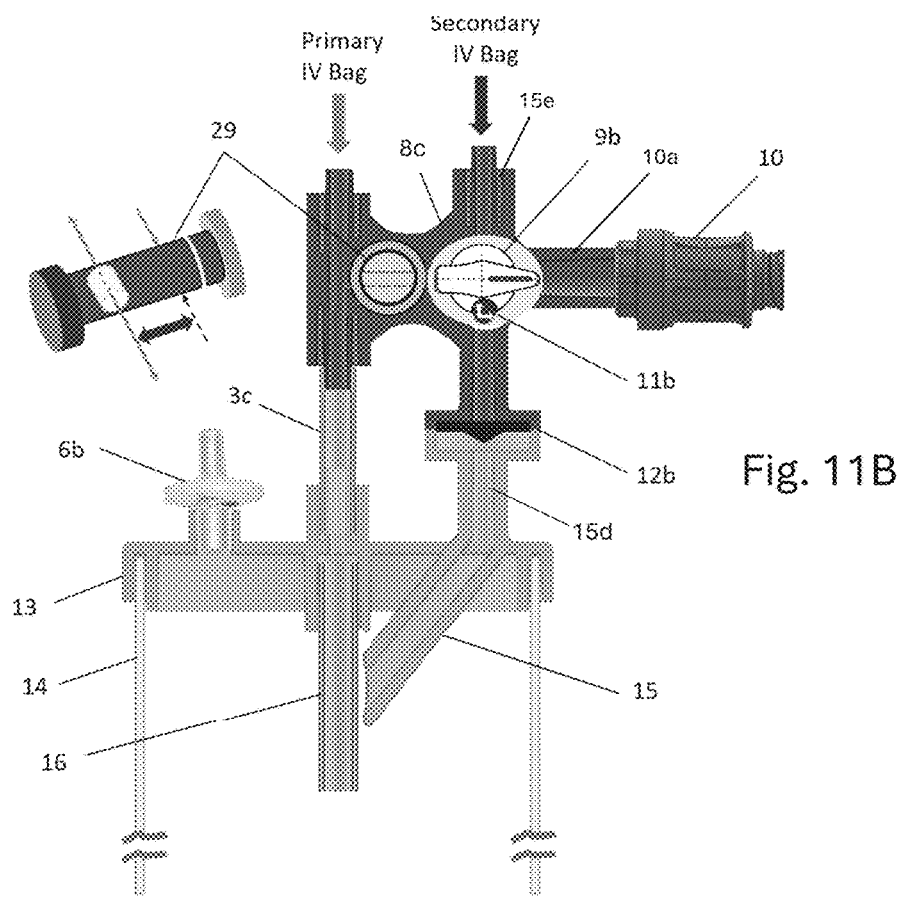
Figure 12:
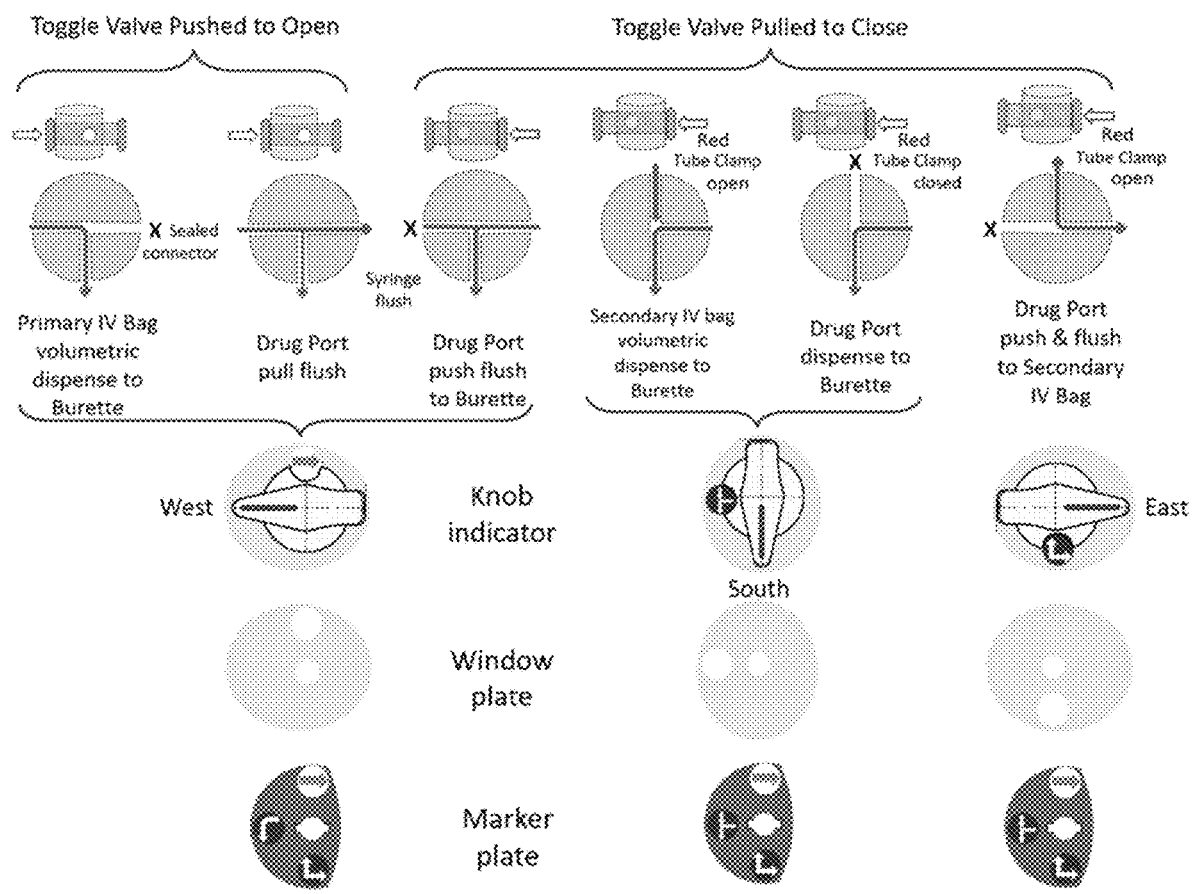
FIG. 12 describes the flow pattern operation of the Burette Top Cap design in FIGS. 11A-B. Configuration reduces the Indicator Knob positions to three and with the Toggle Valve only activated when filling the Burette Chamber or pulling a flush from the Primary IV bag.

FIGS. 11A and 11B detail the Toggle Valve (29) combination with the Rotary T-Valve (8a). The Monoblock Valve Assembly replicates the Tubing port for the Secondary IV bag and the Needleless Connector (10) inputs and Check Valve (12b) output to the Burette Chamber. Behind the T-Valve Knob (9b) is the Position Indicator (11b). Air Vents provide venting for the Burette Chamber (14). FIG. 11Bb shows the larger Air Vent Filter (6b) for use with hazardous fluids. The Monoblock Rotary T-Valve Assembly may take different configurations such as having the Needleless Connector Drug Port at an elevated angle for ease of syringe fluid administration. The control positions of the Toggle Valve and Rotary T-Valve Monoblock Assemblies of FIGS. 11A and 11B are illustrated in FIG. 12. The Toggle Valve (29) is only in the "Pushed to Open" position when fluid from the Primary IV bag is being dispensed either for volumetric fill of the Burette Chamber or to pull a flush to the Drug Port. Implementing the Toggle Valve (29) enables a simpler mold tool while eliminating a Check Valve. This design also reduces the required positions for the T-Valve Knob (9b) to three. In FIG. 12, we see a Window plate and a smaller Marker plate for the three marker icons. With the Toggle Valve closed, the T-Valve Knob pointing South, either dispensing from the Secondary IV bag or from the Drug Port is possible. With the T-Valve Knob rotated East, a syringe on the Drug Port can push its dose up to an undosed Secondary IV bag. A two-step operation is necessary to now flush the syringe on the Drug Port. One, the T-Valve Knob is rotated West, and the Toggle Valve is opened to pull a flush. Then the Toggle Valve is closed so the syringe can dispense its flush directly to the Burette Chamber. Or the T-Valve Knob is rotated back to the East so that the flush can be pushed up to the Secondary IV bag. A design element of the T-Valve body may incorporate a physical position indicator and visual position indicators. The physical indicator may be by way of a detent verifying that the valve body is correctly aligned for proper fluid flow, and upon reaching this detent, a physical confirmation of seating on the notch would translate to a small vibrational confirmation to the valve operator.

Figure 13:
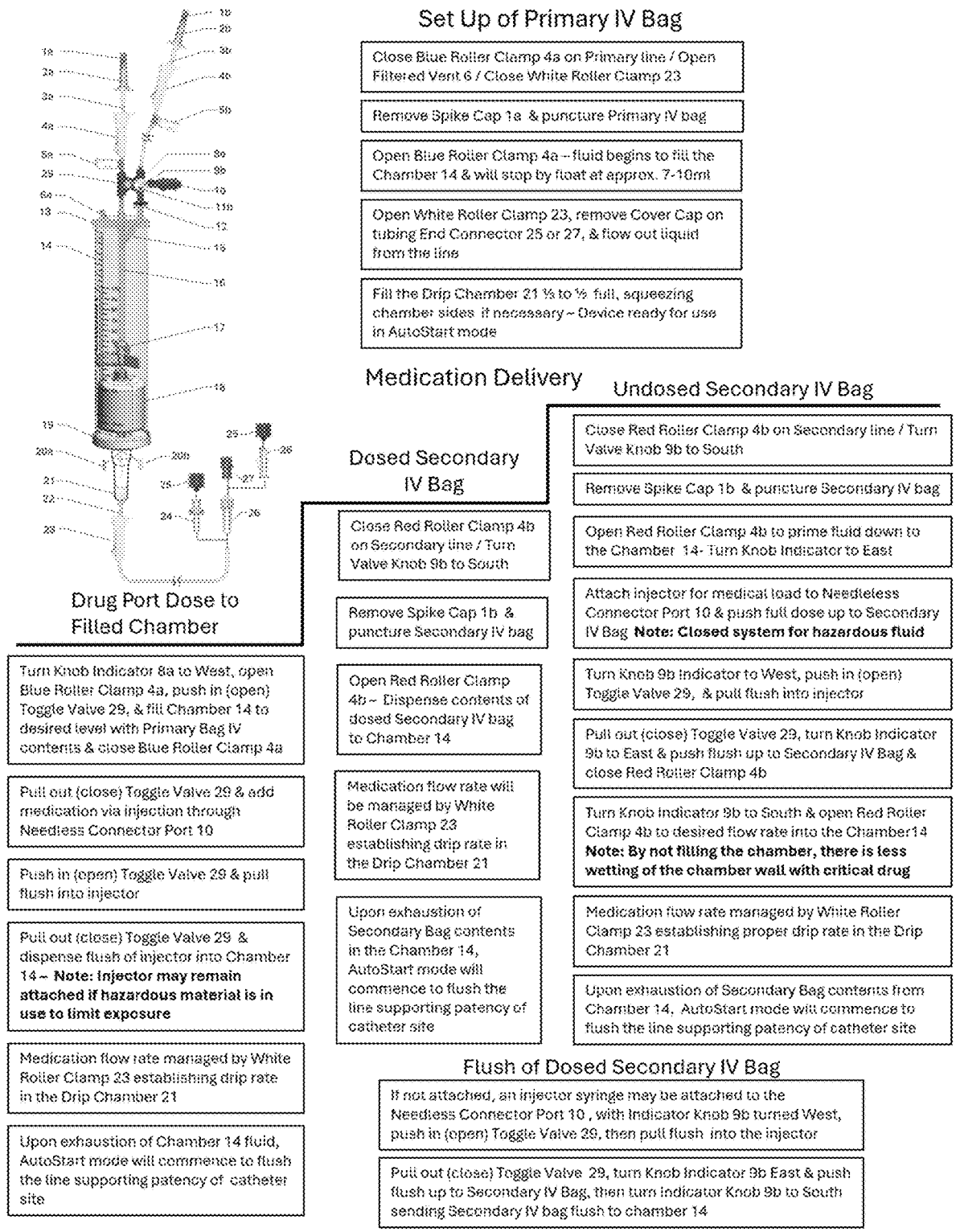
FIG. 13 presents the Safer Infusion System with integrated valve configuration presented in FIGS. 11A-B with a Primary IV bag setup followed by three medical dosing and flushing options.

The flow chart in FIG. 13 details the setup of the Primary IV Bag of the present invention. Follow-on medication delivery options are then listed for 1) A Drug Port dose to the filled Burette Chamber, 2) Dose dispensing from the Secondary IV bag, and 3) Working with an undosed Secondary IV bag that is dosed from the Drug Port such as would be with a hazardous drug. The last step in the process is flushing of the dosed Secondary IV bag. This important step ensures that the patient receives their full prescribed dose.

Figure 14A:
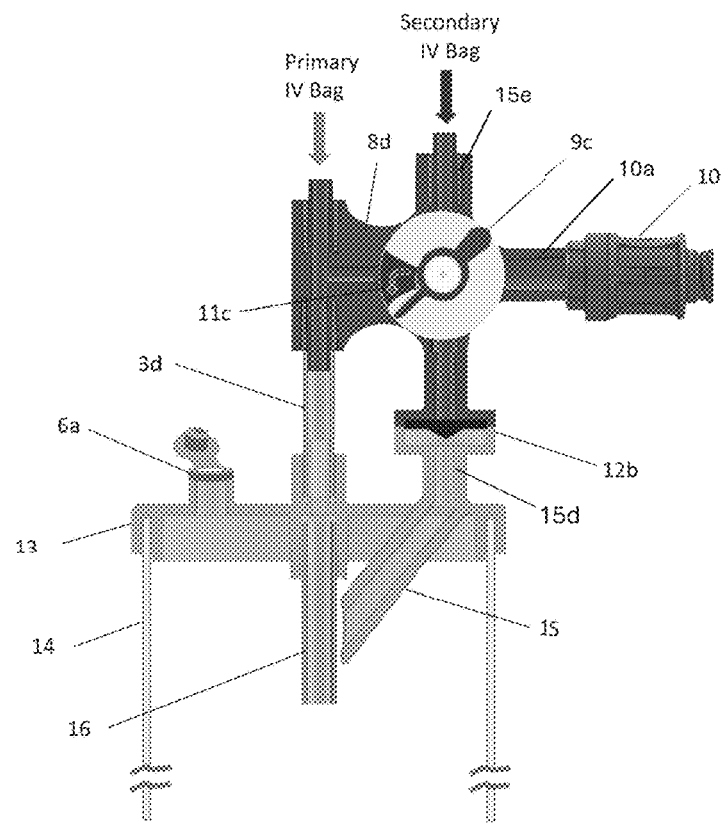
FIGS. 14A-B detail the Burette Top Cap monoblock design with one integrated "L-Port" valve enabling five-position functionality for managing fluid flows delivered into the Burette Chamber.
Figure 14B:
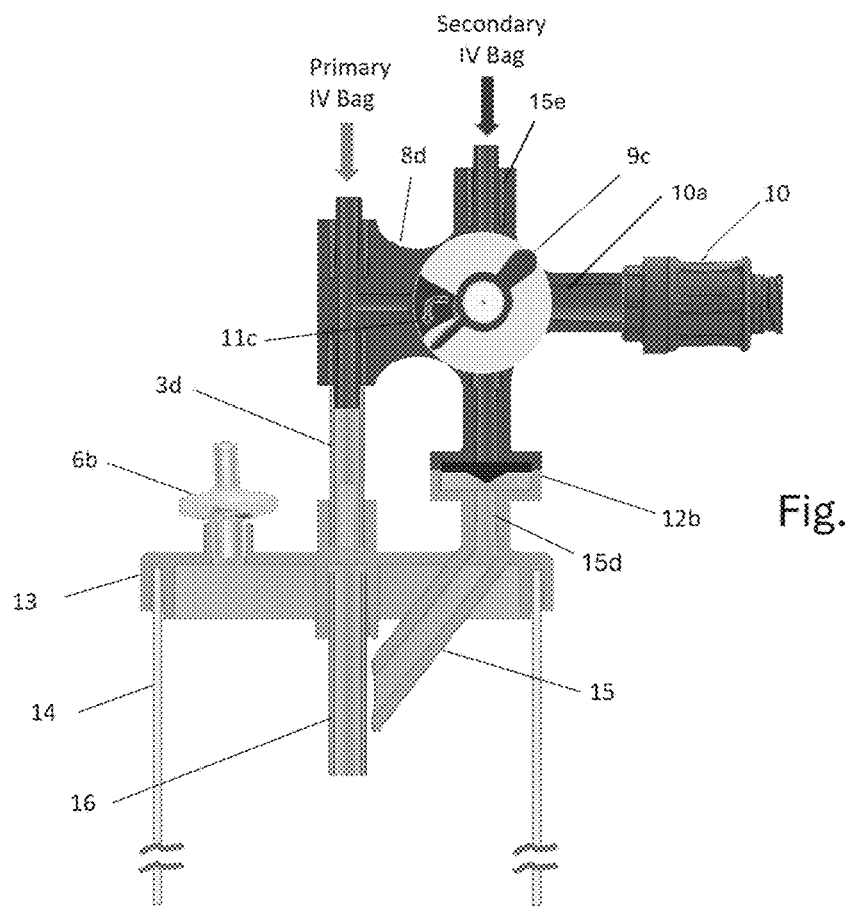
Figure 15:
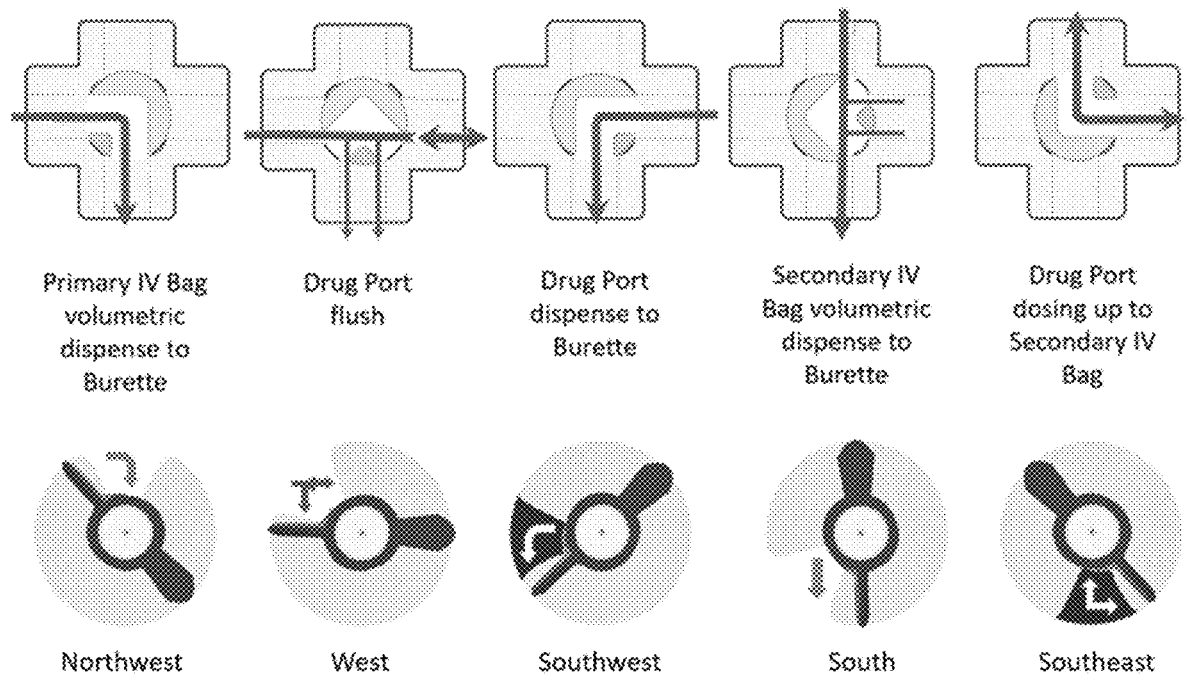
FIG. 15 matches fluid flow pattern options per the Burette Top Cap design in FIGS. 14A-B. Presented are the accompanying control knob position with the flow direction indicated by the exposed icon.

FIGS. 14A and 14B present a third design option with an L-Port Rotary Valve (8d) Monoblock Assembly. Larger diameter flow paths are necessary making the molding of this design more challenging; however, the overall assembly reduces to the single L-Port Rotary Valve (8d) and a Check Valve (12b). Another version eliminating the Check Valve (12b) is an option as the L-Port Rotary Valve can fully seal off the outlet to the Burette Chamber. Shown in FIG. 15 are five valve positions and their respective fluid flow patterns. With the Indicator Knob (9c) pointing Northwest, the Primary IV bag will fill the Burette Chamber to a specific volumetric point. Turing the Indicator Knob (9c) to the Southwest allows the Drug Port to dispense into the Burette Chamber. The Indicator Knob then turned to the West allows a flush pull into the dosing syringe, followed by a turn to the Southwest to push the flush into the Burette Chamber. Turning the Indicator Knob to the South will permit a flow from the Secondary IV bag into the Burette Chamber. The last position of the Indicator Knob to the Southeast enables a Drug Port dose up to the Secondary IV Bag. A design element of the L-Port Rotary Valve body may incorporate a physical position indicator in addition to this visual position indicator. The physical indicator may be by way of a detent verifying that the valve body is correctly aligned for proper fluid flow, and upon reaching this detent, a physical confirmation of seating on the notch would translate to a small vibrational confirmation to the valve operator.

Figure 16:
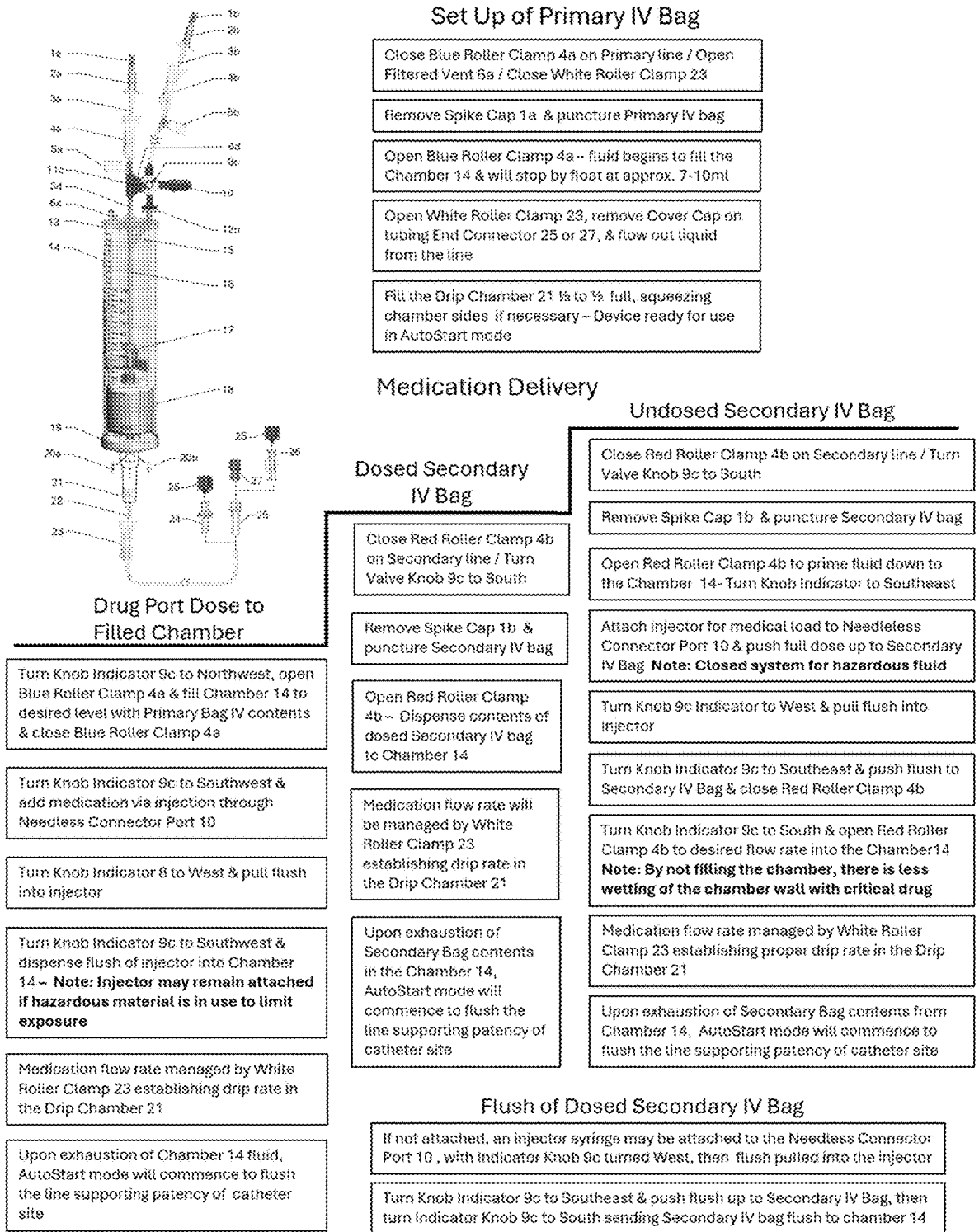
FIG. 16 presents the Safer Infusion System with integrated valve configuration presented in FIGS. 14A-B with Primary IV bag setup followed by three medical dosing and flushing options.
Figure 17:
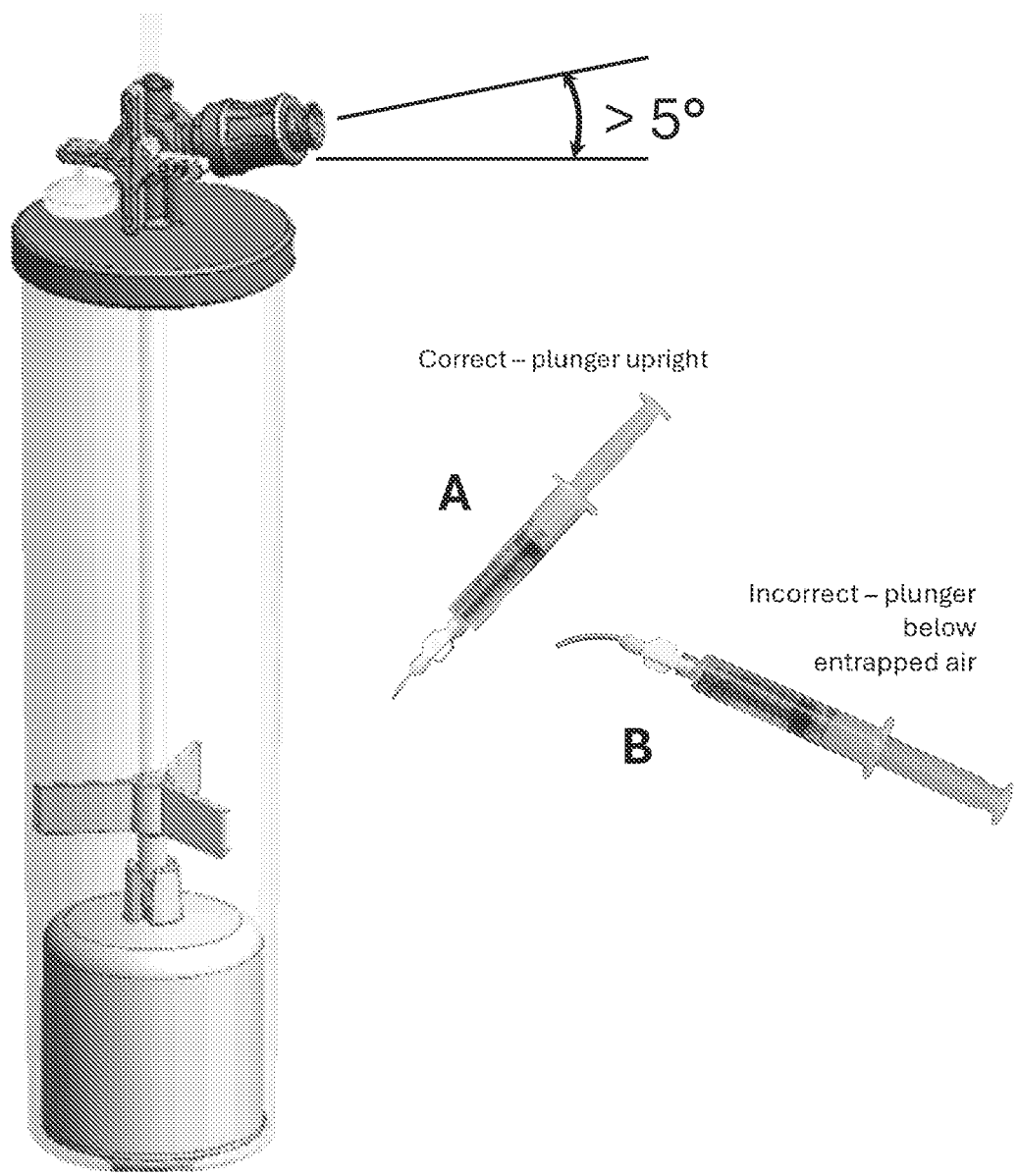
FIG. 17 illustrates the design element of creating a >5° angle on the Drug Port Needleless connector as part of the Burette Top Cap assembly to ensure that air in a connected syringe will not be able to flow from the syringe such that the precise medicinal volume is dispensed.

The flow chart in FIG. 16 details the setup of the Primary IV Bag. Follow-on medication delivery options are then listed for 1) A Drug Port dose to the filled Burette Chamber, 2) Dose dispensing from the Secondary IV bag, and 3) Working with an undosed Secondary IV bag that is dosed from the Drug Port such as would be with a hazardous drug. The last step in the process is flushing the dosed Secondary IV bag. This important step ensures that the patient receives their full prescribed dose. Depending on the molding constraints and assembly simplification, a design goal is to make the Drug Port Needleless Connector angle at least $5°$ above a horizontal plane as illustrated in FIG. 17. Although the Burette Chamber is vented, it is always good practice for any entrapped air in a syringe to be kept away from the dispensing nozzle for precision in the amount of liquid injected.

Optimized Mixing and Flushing Within the Burette Chamber of the Present Invention The present invention introduces two functional improvements to the float design. Both elements enhance the system's overall flushability with the least amount of flush volume while maintaining an adequate volume and weight necessary to provide a sealing force on the outlet tube when fluid is at its minimum establishing an air stop even at an acute burette chamber angle.

Figure 18:
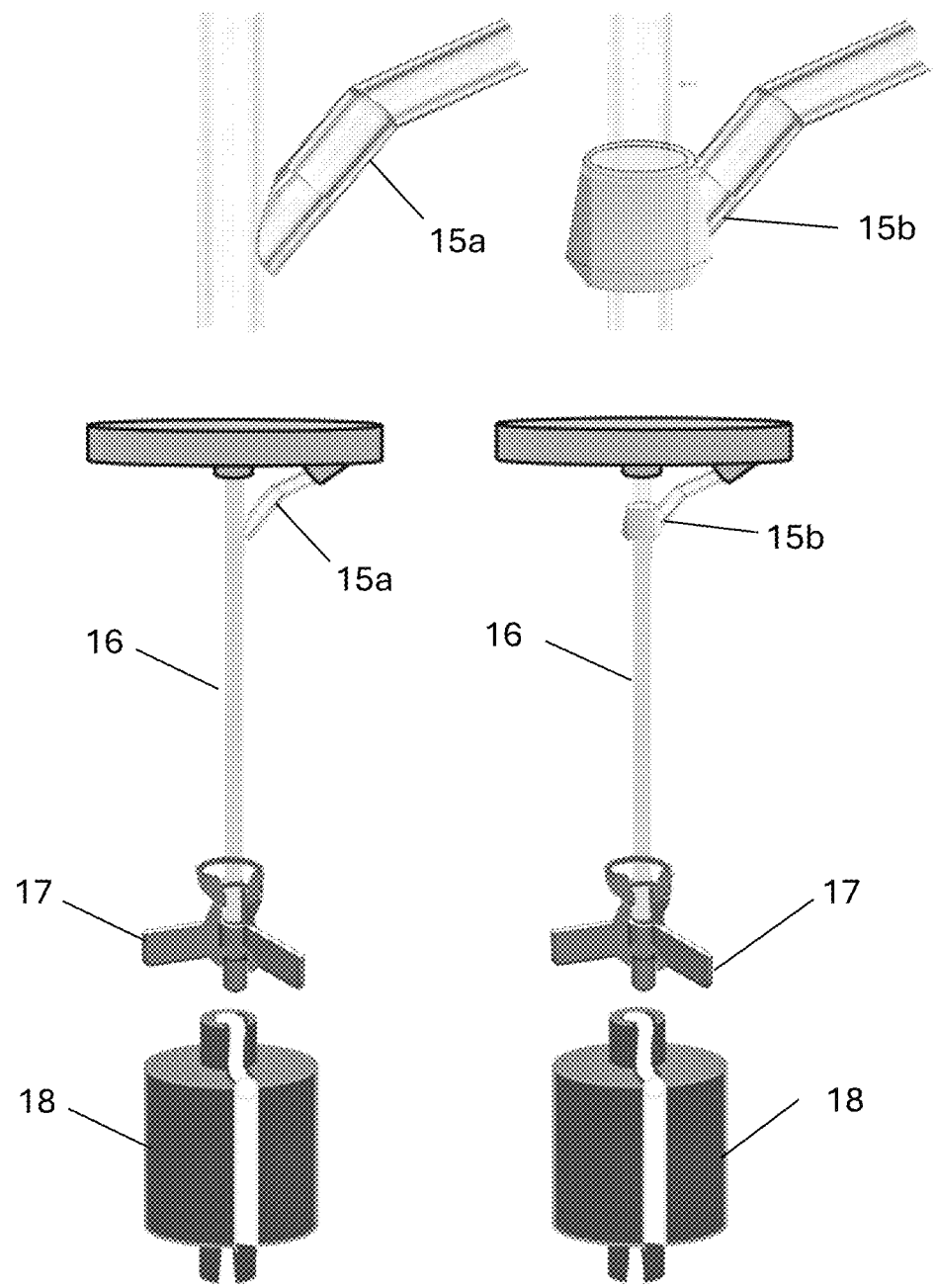
FIG. 18 shows two designs of the Drug Port Directed Flow Channel.

Burettes with a Drug Port in the burette top cap dispense their liquids directly into the chamber with no regard to how the liquid might shower down into the chamber. We now look to the inventive feature in FIG. 18 with a Directed Flow Channel (15a and 15b) configured below the Burette Top Cap. The introduced liquid is directed towards and, in the case of a cone (15b) surrounding the Central Tube in FIG. 18, flow is constrained to travel along the outside of the Central Tube. In this configuration, only the wetted outside of the Central Tube needs to receive a flush thereby reducing the active flush volume to achieve the goal of moving any residual drug to the burette base.

Figure 19:
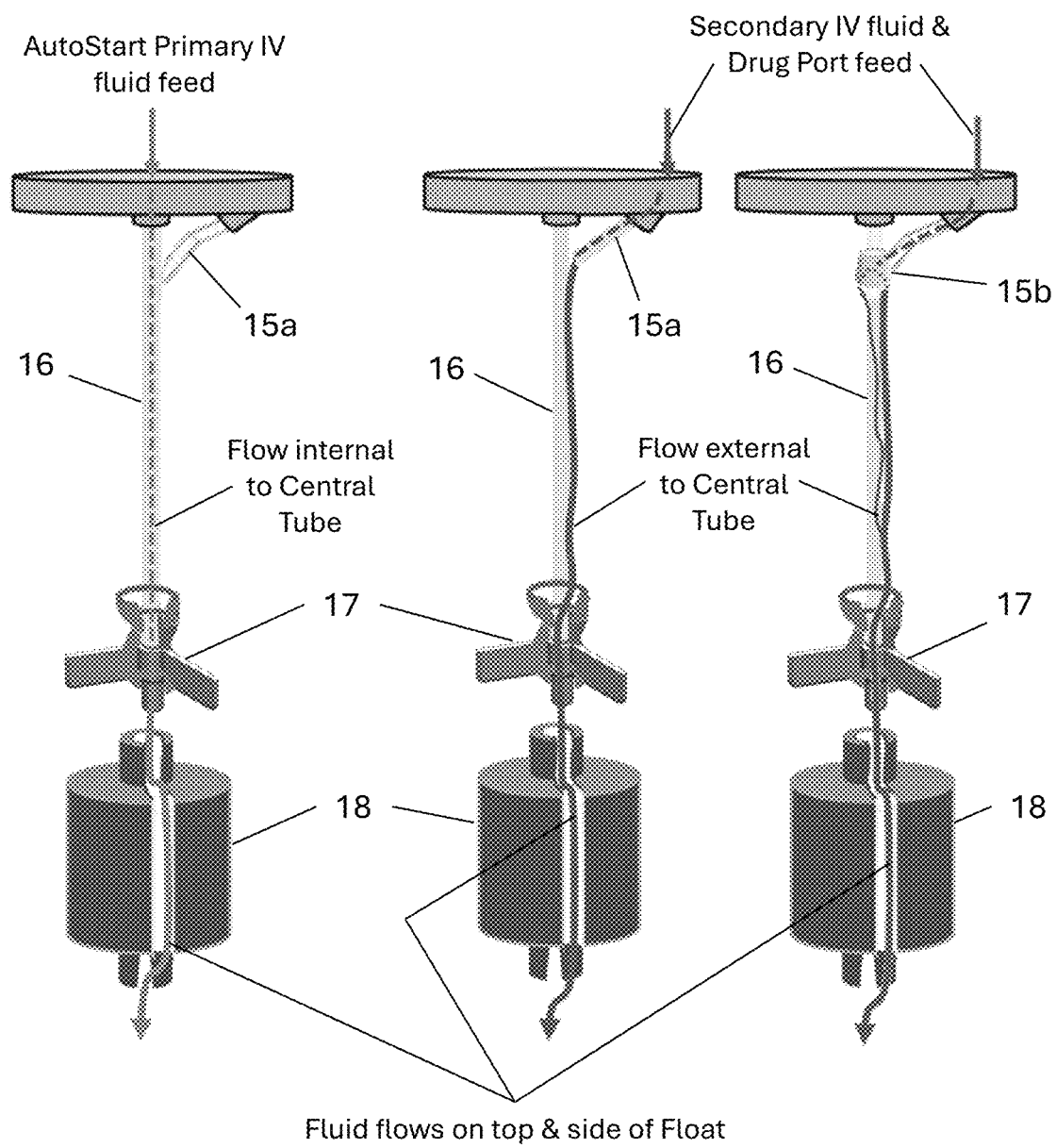
FIG. 19 shows side-by-side separate liquid flow patterns into the Burette Chamber.
Figure 20:
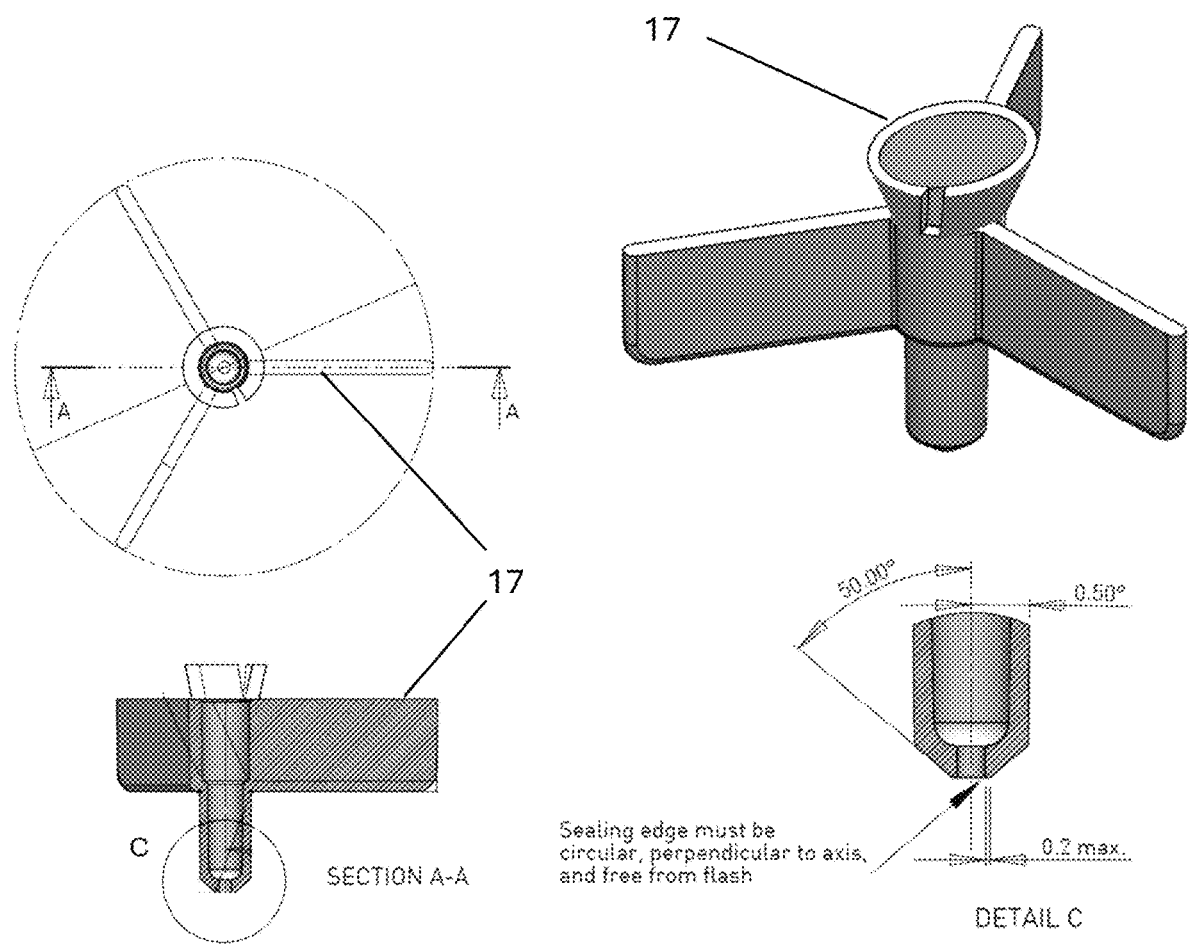
FIG. 20 illustrates a Liquid Confinement Cup addition to the top side of the Alignment Piece capturing and directing liquid flow external to the Central Tube in the Burette Chamber.

FIG. 19 illustrates how the AutoStart Primary IV fluid feed always flows internally with the Central Tube (16) (dotted line) dispensing out of the nozzle base of the Alignment Piece (17). The Secondary IV fluid and Drug Port feed liquid flow pattern flows internally to the Directed Flow Channel (15a and 15b) and then externally (solid line) down the outside of the Central Tube (16). The external flow is collected in a cup feature of the Alignment Piece (17) detailed in FIG. 19. This Confinement Cup highlighted in FIG. 20 has a single outlet directing liquid flow down one side only of the Alignment Piece for less surface wetting.

Figure 2:
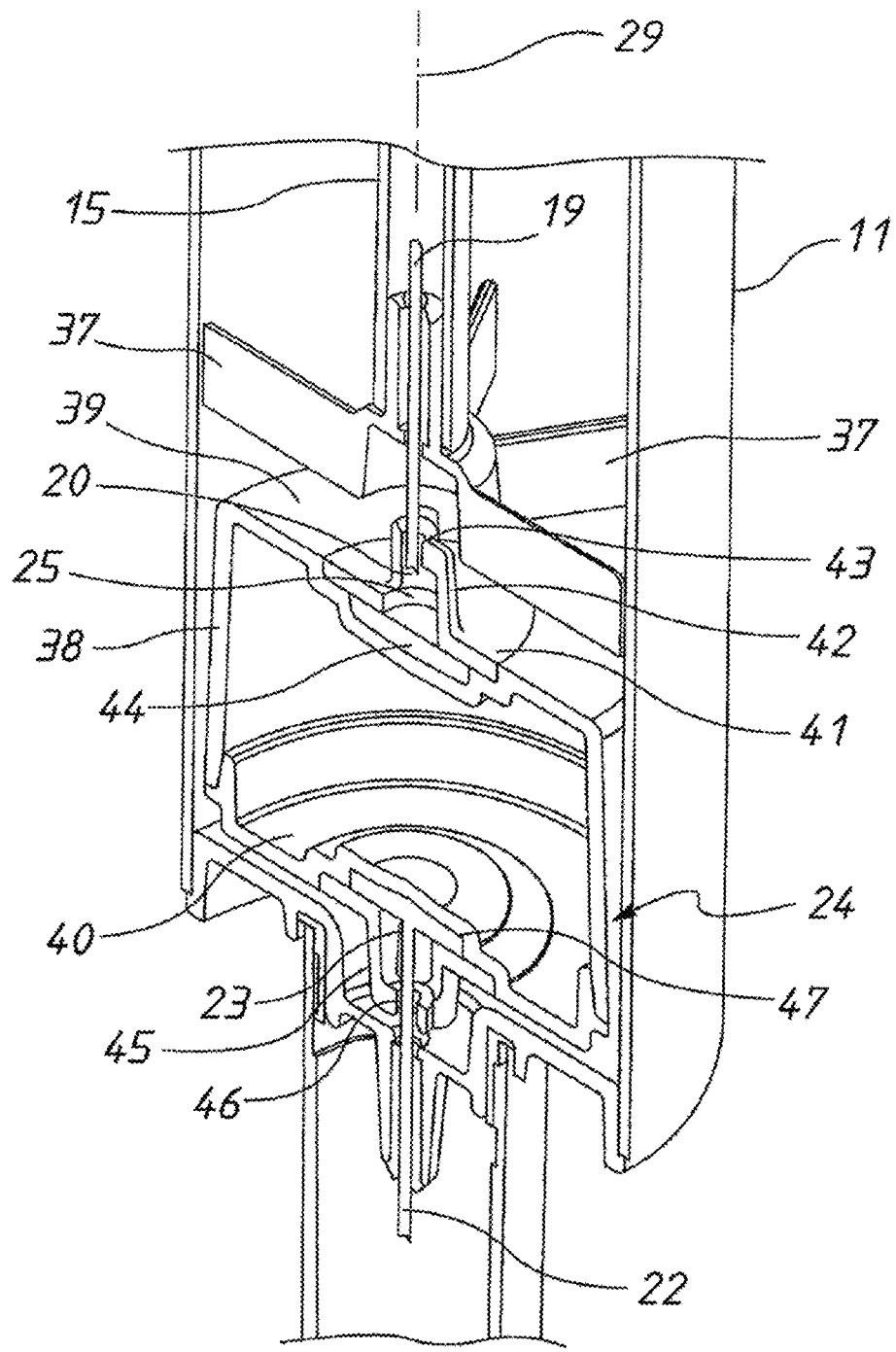
FIG. 2 is a reproduction of FIG. 3 in prior art U.S. Pat. No. 9,352,080 B2 which illustrates a schematic sectioned side elevation of the lower section of a burette employing a float system for modulating IV fluid flow while protecting against air entering the fluid line below the chamber.
Figure 21:
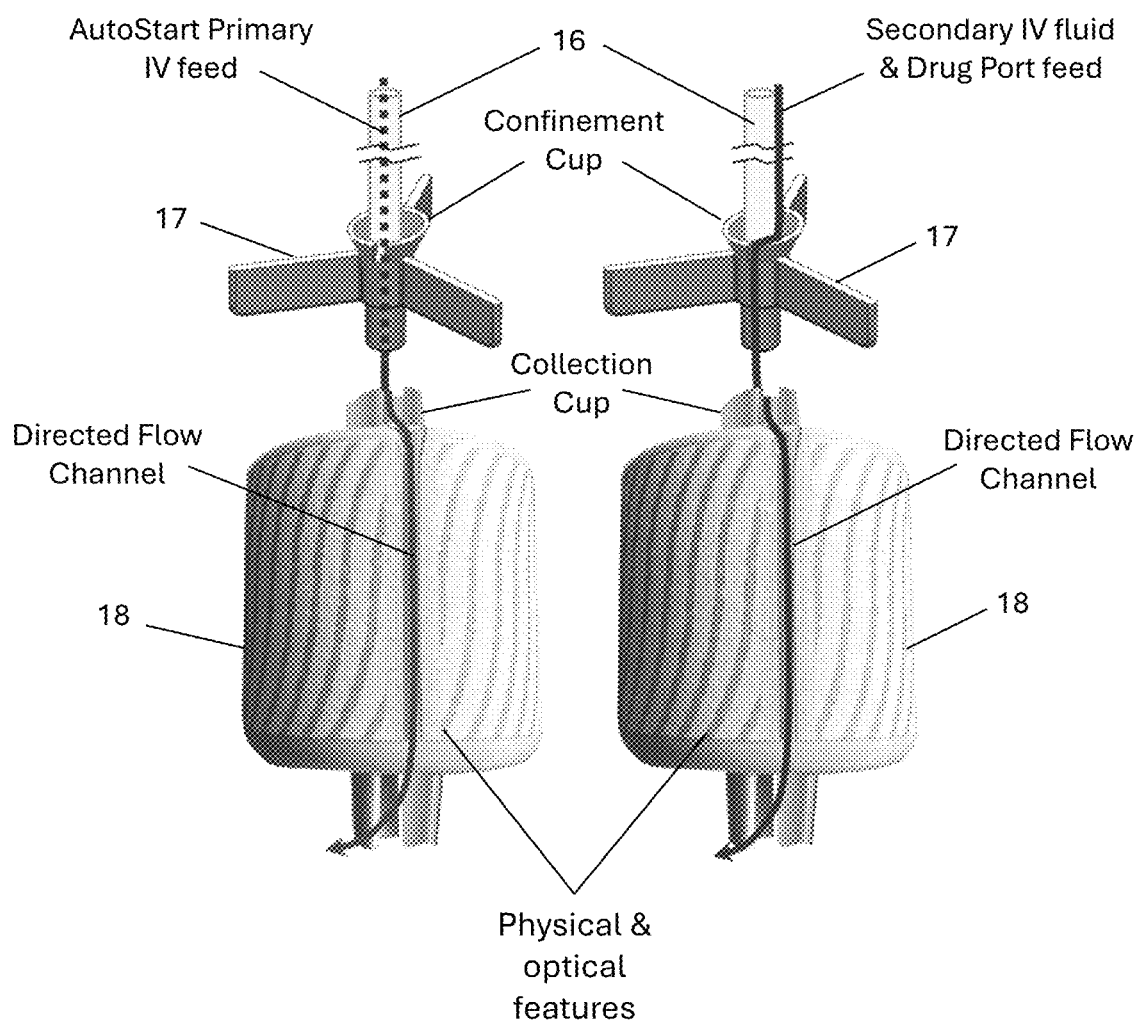
FIG. 21 illustrates two separate liquid flow patterns. AutoStart Primary IV fluid travels on the inside of the Central Tube. Secondary IV fluid and Drug Port injected fluid flows down the outside of the Central Tube.

The upper opening or "hollow projection" of item 42 in FIG. 2 is modified into a cup shape shown in FIG. 21 designated as the Collection Cup. The cup retains the resilient pad 44 in FIG. 2 but now incorporates a single sidewall opening that directs fluid to an open U-shaped single channel in the float top extending radially to the edge of the float to a matching U-shaped channel down the side of the float. These Directed Flow Channels configured as such present a smaller surface area subsequently requiring a flush to deliver any residual drug for a full prescribed dose and to prevent potential mixing of drugs by the introduction of a following liquid therapy. Additional features of the outer vertical sides of the Float (18) may be employed to create a rotational action of the float. Design elements such as a set of external ridges or other smooth surface interruptions will respond to liquid flowing past them creating a lateral turning force. So, as fluid drains from a filled burette, its downward motion will sponsor rotational, mixing dynamics useful should more than one liquid be introduced to the burette. Additionally, optical elements may be incorporated onto the Float (18) to enhance the visibility of the rotational action from a distance.

Figure 22:
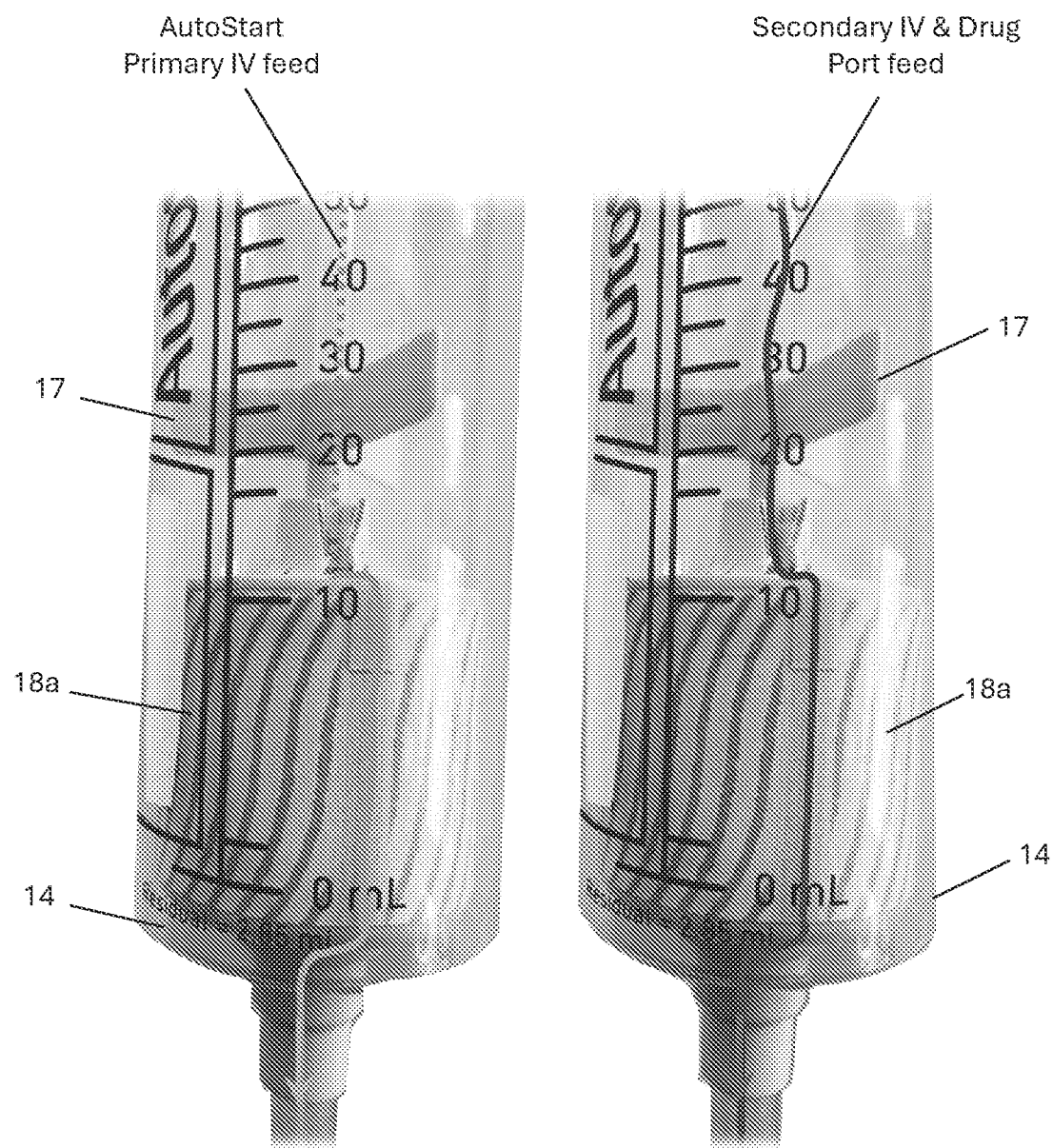
FIG. 22 shows side-by-side separate liquid flow patterns into the Burette Chamber base.

The minimized surfaces requiring a flush design element provide a much more effective actual flush operation after the exhaustion of a Secondary Bag IV or Drug Port dose delivery. FIG. 22 presents a fluid flow pattern for both the AutoStart Primary IV and the Secondary IV/Drug Port fluid flows within the Burette Chamber, ultimately collected in the Burette Chamber Bottom Cap (19) to flow out through the exit nozzle.

Figure 23:
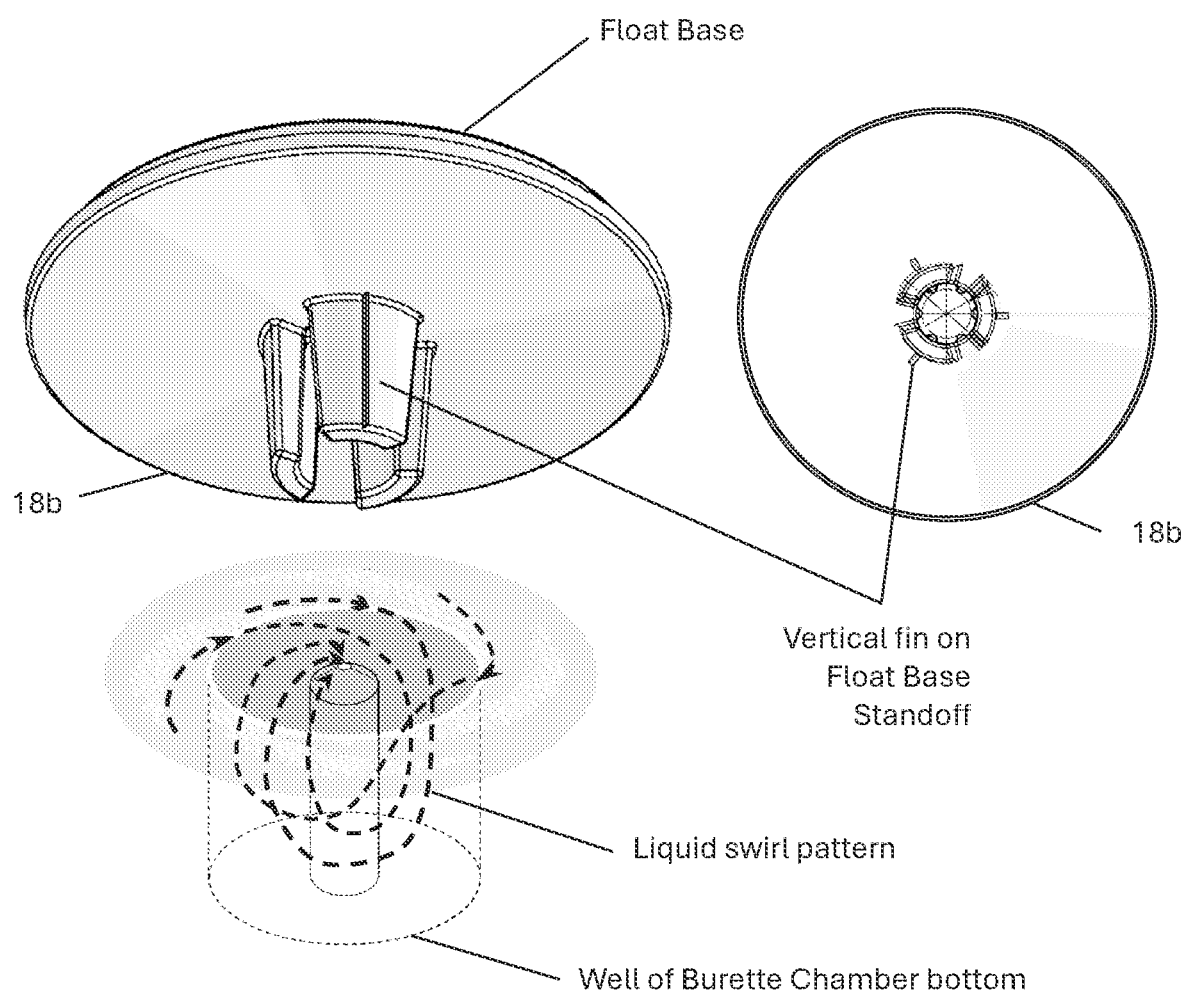
FIG. 23 details the Float Base Standoff and exemplary fluid swirling pattern in the well of the Burette Chamber bottom.
Figure 24:
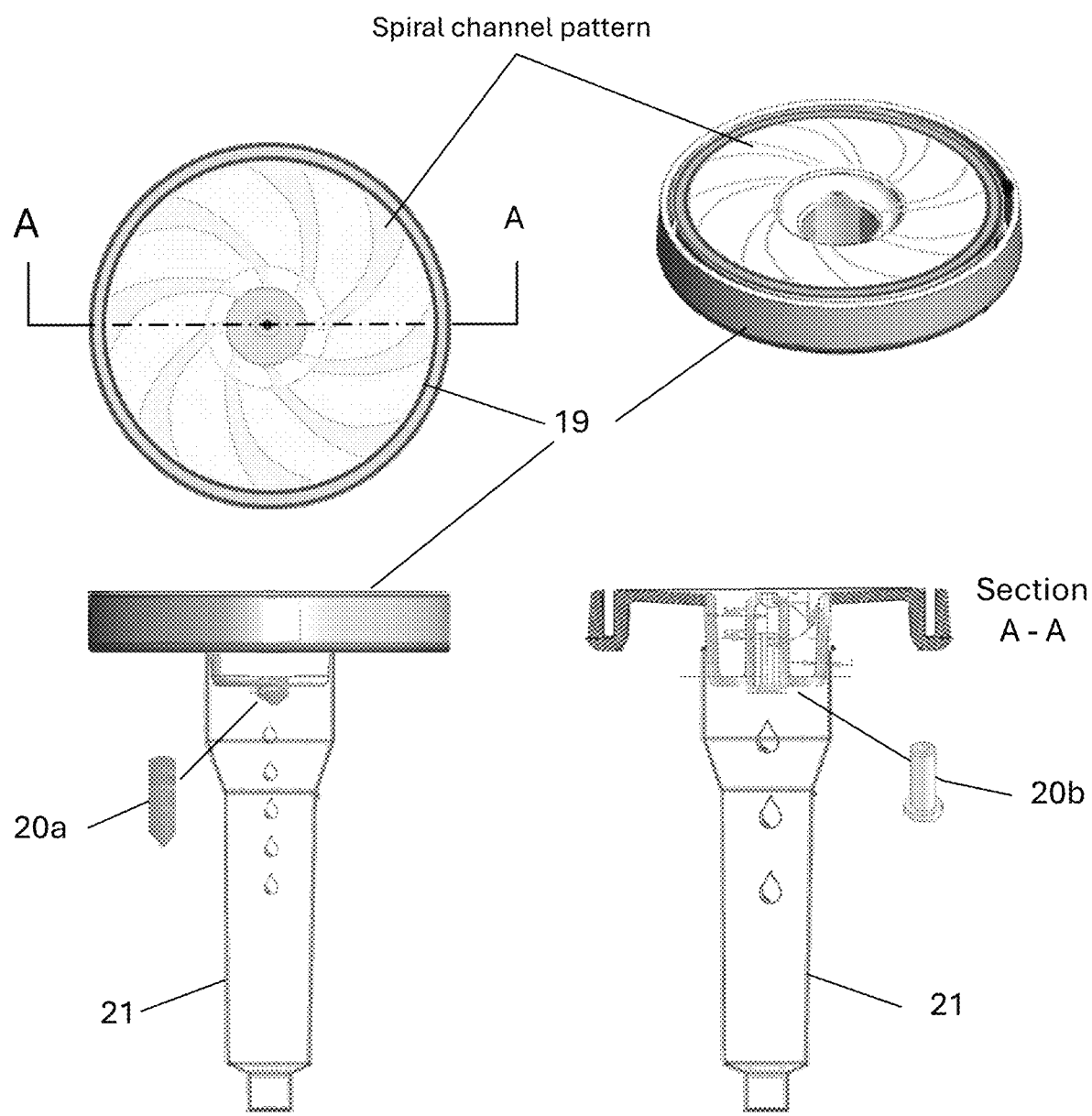
FIG. 24 illustrates a Burette Chamber bottom with a channel design sponsoring a fluid swirl pattern effect. Also shown are Micro Drip and Macro Drip inserts to the Burette Chamber Bottom Cap.

To further enhance liquid mixing for homogenous IV medicine delivery and flushing, an additional feature is incorporated into the Float Base shown in FIG. 23. Small fins are added to the Float Base Standoffs. These fins may engage with the fluid draining down into the Well of the Burette Chamber Bottom putting a lateral rotational pressure on the fins to spin the freely buoyant Float (18). Detailed in FIG. 24 is one possible Spiral Channel Pattern in the Burette Bottom Cap (19). Exiting liquid is directed into a swirling motion that may support a pressure interaction with the small fins applying sufficient force to rotate the Float (18).

Provisions may allow for either a Micro-Drip Nozzle (20a) or a Macro-Drip Nozzle (20B) to be installed into the Burette Chamber Bottom (19). Both nozzle types are designed to function with the Drip Chamber (21) attached to the Burette Chamber Bottom (19).

Relying on gravity, the drip chamber allows control of fluid flow where drops form and fall at a consistent rate, indicating the flow rate. Whether the preceding burette is full or nearly empty, the drip chamber mitigates volumetric pressure changes of the fluid draining from the burette by maintaining a relatively constant pressure, ensuring a consistent flow rate. This is achieved by the design of the drip chamber itself, which allows air to enter and equalize pressure as fluid exits.

Toggle Drip Nozzle of the Present Invention

Figure 25:
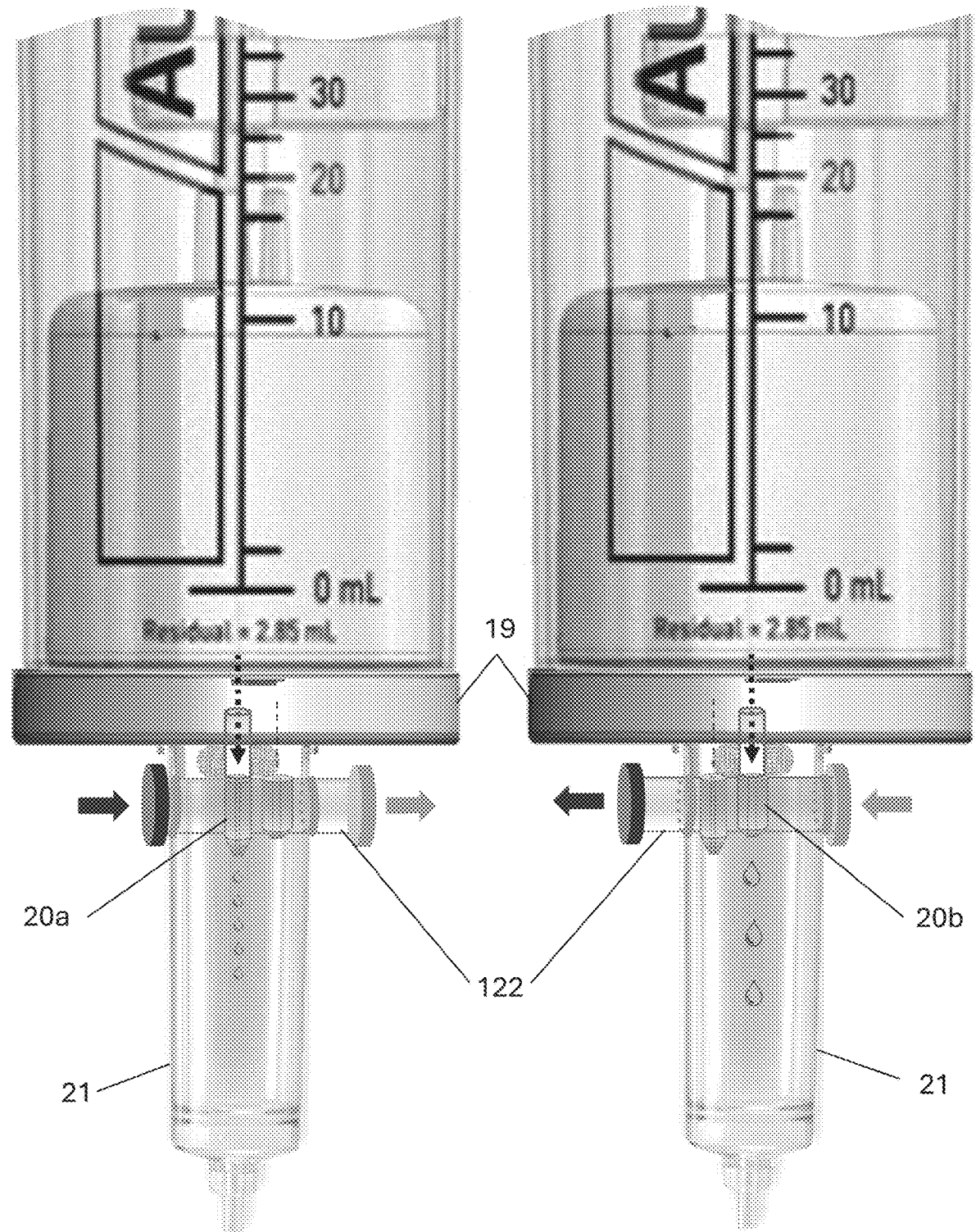
FIG. 25 presents a Toggle Valve design for choosing between a macro-drip and a micro-drip element fully contained within the drip chamber.

In keeping with the overall goal of a universal burette system, a Nozzle Toggle Valve (122) may be incorporated with the Drip Chamber (21) as illustrated in FIG. 25. This Nozzle Toggle Valve slides laterally to position either a micro-drip or a macro-drip nozzle into the flow position below the fluid outlet from the Burette Chamber Bottom (19). With this design feature, caregivers embrace the simplicity of choice for matching the prescribed drug infusion rate with the appropriate nozzle. This ready option especially serves IV infusions initiated in the field, in emergency response vehicles where inventory space is severely limited, and for home care.

Hazardous Material Handling with the Present Invention

The standard vent port located on the Burette Top Cap (13) equalizes pressure allowing IV fluids to flow freely from an infusion bag, bottle, or Drug Port injection. For non-hazardous drugs being infused, the air venting requirement is met using a hydrophobic filter element (6a) such as a micro-glass fiber, with a typical pore size of 0.45 µm, and a cellulose-acetate support molded into or bonded to a PVC frame in turn bonded to the Burette Top Cap air vent port. This filter media protects against foreign material entering the burette chamber and prevents burette liquid from escaping should the burette be inverted for any reason.

Hazardous IV infusion drugs, such as chemotherapy agents and certain biologics, have specific characteristics that necessitate careful handling, administration, and disposal per OSHA and NIOSH standards. These drugs pose a risk to healthcare workers, patients, and the environment if not properly managed. Concerns include reproductive toxicity, carcinogenicity, mutagenicity, as well as irritancy and corrosivity to skin and mucous membranes. For these reasons, stringent safety protocols for wearing personal protective equipment (PPE) and incorporating Closed-System Transfer Devices (CSTDs) are normally specified. Rigid plastics and elastomers chosen for these systems are sufficiently impervious to the liquids and vapors.

CSTDs are specialty locking connectors and are normally specified because Luer-lock fittings do not make a true "locking" connection. Additionally, the skirt does not provide necessary leak protection. For example, a syringe connected to the Drug Port might loosen. For this reason, delivery of hazardous infusion drugs to the Safer Infusion System can be supported by specifically designed locking CSTD hardware from B. Braun's OnGuard product line, Simplivia's Chemfort product line, Becton Dickinson's PhaSeal product line, ICU Medical's ChemoLock product line, and Vigon's Qimono product line.

Managing Vapors in a Closed System of the Present Invention

Managing the venting aspect with hazardous liquids requires further material upgrades to minimize vapor release for enhanced workplace safety. The upgraded Hazardous Fluid Air Filter Modules are described in FIG. 26. One choice of adsorptive material is Chemviron FLEXZORB ACC 100% activated woven carbon cloth (25) with a large electrostatic surface area performing efficiently to adsorbing vapors. Combined with his carbon layer is a single or top and bottom layer of BFF Nonwovens Ltd.'s SVQ30 Nonwoven Synthetic Fibers (100% Rayon or 100% Viscose) chemically bonded carrier (24). This hazardous vapor filter is stacked with a GVS Filter Technology membrane (26) as one option. This membrane is a hydrophobic polytetrafluoroethylene (PTFE) 0.2 μm pore size filter. These filter membranes are encapsulated by a top and bottom structural shell of Polyvinylidene Fluoride (PVDF), Polypropylene (PP), or Polyethylene (PE).

Figure 26:
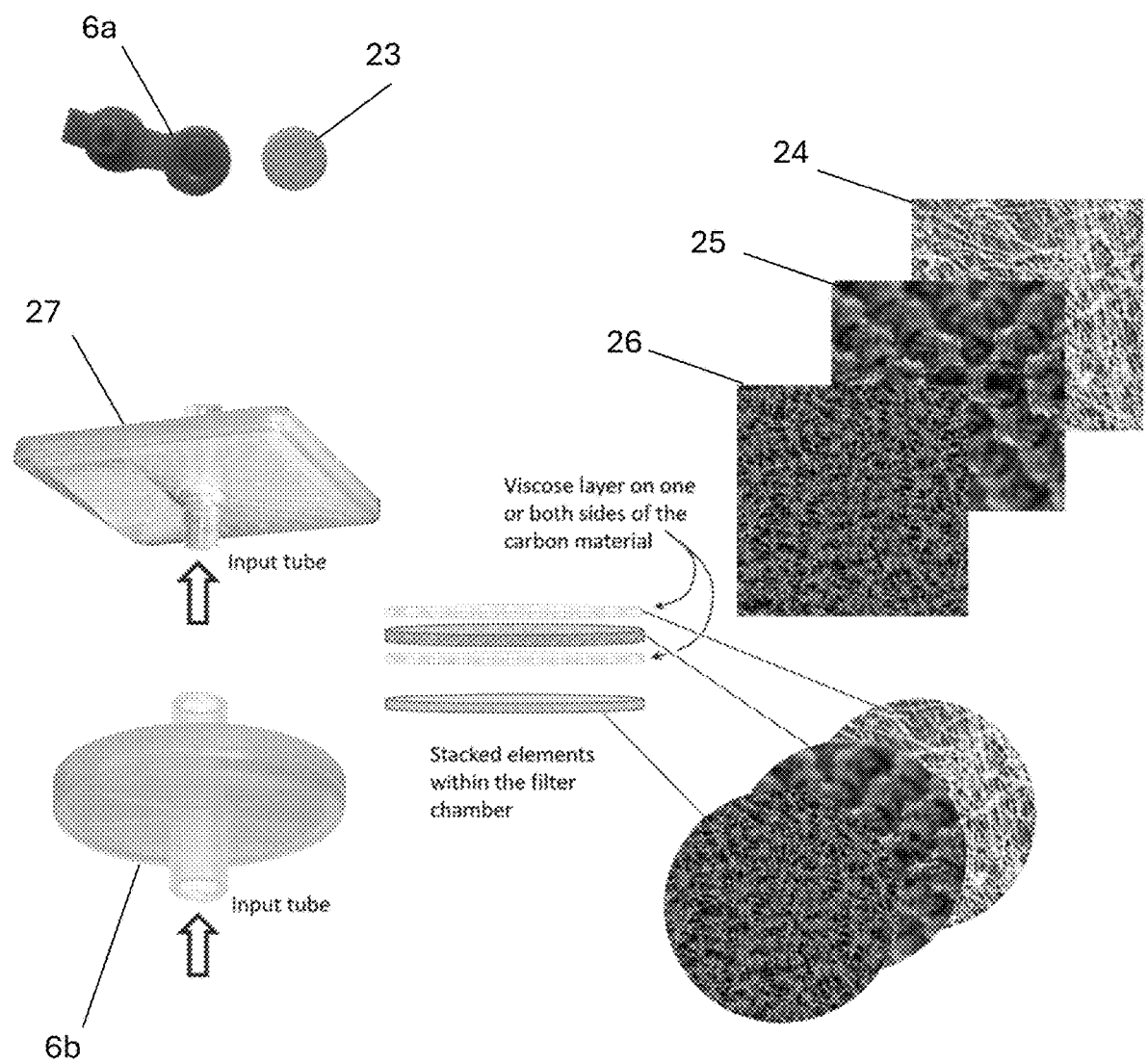
FIG. 26 describes the filter element materials incorporated into a hazardous Vapor Filter Module configured in a round or rectangular format.
Figure 27:
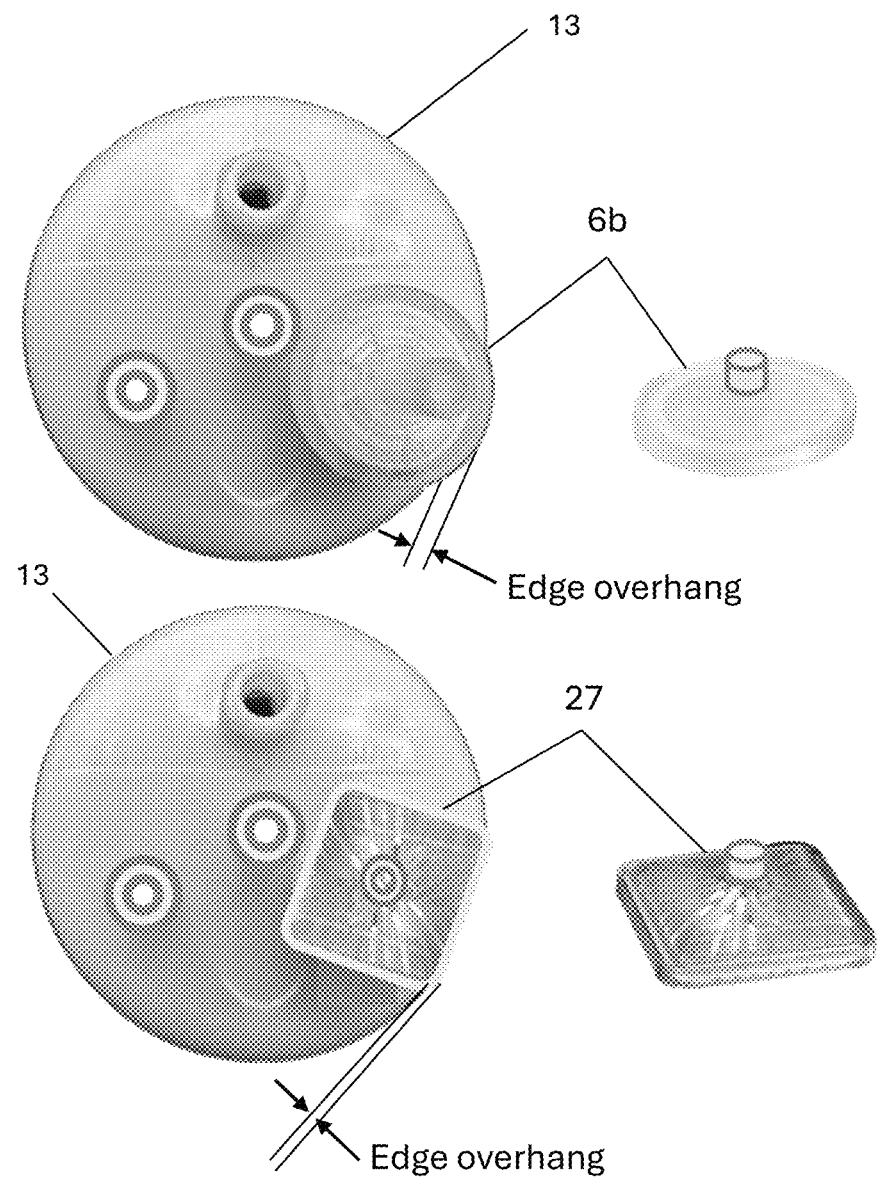
FIG. 27 shows a Burette Top Cap with round and rectangular format Vapor Filter Modules installed.

Further shown in FIG. 26 are two configurations of a two-piece filter housing with a round format (6b) and a rectangular format (27) into which the filter stack is sealed. The underside port of the filter housing bonds into the air vent port in the Burette Top Monoblock. The upper side of the filter housing is open to the atmosphere with a smaller diameter opening than the entry point to improve the residence time of the hazardous vapors interacting with the carbon adsorption bed. The round filter structure (6b) incorporates an array of arcuate ribs reinforcing the filter medium while distributing gas flow more evenly across the filter surface preventing channeling where vapor flow seeks the path of least resistance. The rectangular filter structure (27) may incorporate an array of radial ribs for the same media reinforcement and venting distribution purposes. The rectangular shape optimizes the use of the sheet material from which the various filter layers are die-cut. The rectangular shape may be optimized such that the filter housing best fits within the outer boundary column of the Safer Infusion System burette body to prevent any damage to the filter module during packaging and shipping. A comparison of edge overhangs for the round filter housing versus the rectangular housing is designated in FIG. 27.

Figure 28C:
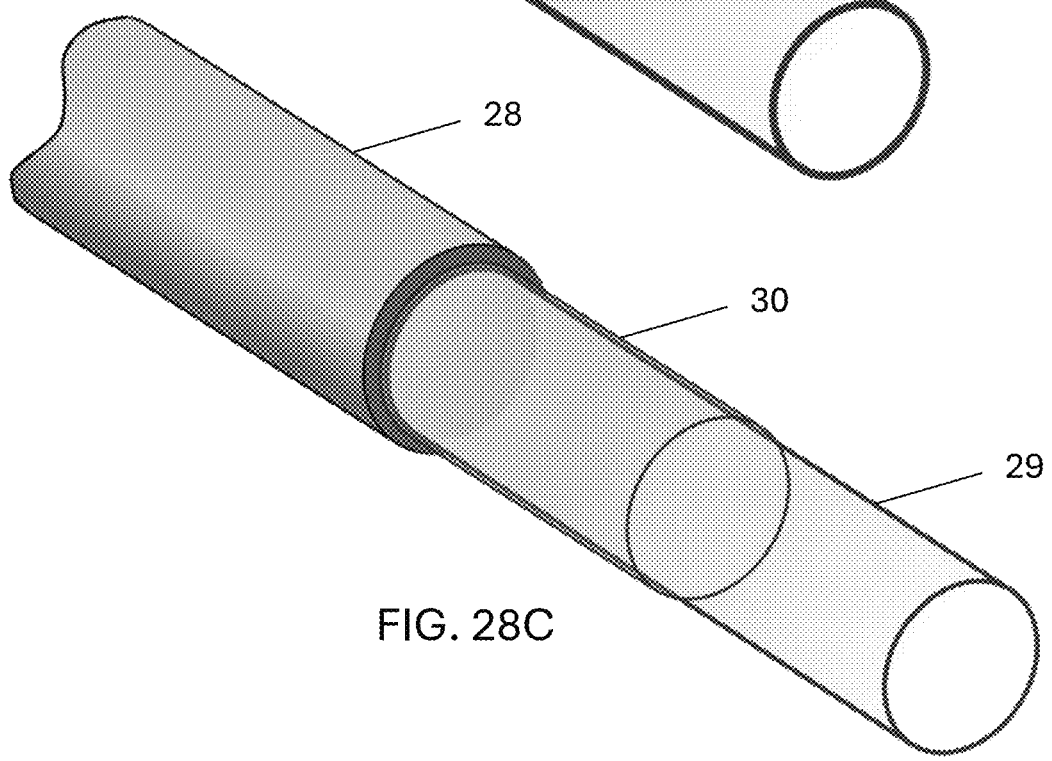

Flexible Tubing & Plastic Material Upgrades for Hazardous Material Handling in the Present Invention Several material options to upgrade from the standard DEHP-free PVC tubing are employed for non-hazardous infusion medications. A single wall design (28) of FIG. 28A might be extruded from a silicone rubber, a thermoplastic elastomer (TPE), polyethylene (PE), or a polyurethane (PU) which exhibit robust tolerance of caustic chemotherapy compounds as well as protecting against releasing of any material when exposed to certain solvent like compounds. Another option is a coextruded tubing illustrated in FIG. 28B where the inner wall (29) may be a polyurethane with a PVC outer jacket (28). A third construction detailed in FIG. 28C is constructed from a low-density polyethylene (LDPE) inner layer (29), an ethylene-vinyl-acetate-copolymer (EVA) bonding agent (30), and a PVC outer layer. The use of PVC as the outermost layer with constructions in FIGS. 28Bb and 28C support standard bonding and sterilization processes while providing lower cost and consistency with Roller Clamp interaction.

SIS molded or extruded plastics commonly used for handling chemotherapy drugs include Cyclic Olefin Copolymer (COC) and Cyclic Olefin Polymer (COP), Polypropylene (PP), Polyethylene (PE), Polyurethane (PU), Thermoplastic Elastomer (TPE), and for very special conditions Fluoropolymers (e.g., Polytetrafluoroethylene (PTFE), Fluorinated Ethylene Propylene (FEP), and Perfluoro alkoxy (PFA)). These materials are upgrades from typical plastics employed for burette manufacturing that include Polymethyl Methacrylate (PMMA) and Polycarbonate (PC), Acrylonitrile Butadiene Styrene (ABS), and Polyvinyl Chloride (PVC). Chosen materials must provide chemical compatibility, transparency where desired, certain mechanical properties, and ease of manufacturing.

Managing Light Sensitive Infusion Compounds in the Present Invention

Antineoplastic refers to agents or substances that inhibit or prevent the growth and spread of tumors or malignant cells. To perform their roles, these antineoplastic compounds can have permeating solvent-like properties that can cause swelling and deformations, cause leaching of plasticizers and other additives, and can cause mechanical issues like brittleness and cracking of certain polymers.

FIG. 29 lists the known antineoplastic compounds under three headings of Vessicants, Irritants, and Nonvessicants. Highlighted are ten compound families considered ultraviolet (UV) and/or visible light sensitive: Docetaxel, Doxorubicin, Etoposide, Gemcitabine, Irinotecan, Methotrexate, Paclitaxel Teniposide, Topotecan, Vinorelbine. To best manage the IV fusion process for these light-sensitive compounds, the Safer Infusion System employs modified materials that perform their regular function while reducing UV and visible light reaching the sensitive liquids. In FIG. 30Aa, a colored plastic envelope (31) can be supplied in a Light Sensitive Oncology Kit. This envelope slips over a standard IV bag for light protection. Healthcare facilities and drug compounders may also supply pigmented Secondary IV bags for use with the Light Sensitive Oncology Kit. In FIGS. 30B-C, the tubing specified has sufficient pigment added to the outer jacket of a coextruded flexible tubing (32a and 32b) to block light while the inner layer(s) maintain their full chemical protective properties. Burette Chambers in FIG. 30E may be extruded or molded from plastic compounds dosed with sufficient pigment for light blocking. The same pigmented molding compound can be used for the Drip Chamber of FIG. 30F. Other components in the Safer Infusion System may be produced from opaque plastics that do not require further addition of pigments to block UV and visible light.

Pigments specified for the Hazardous Material Handling versions of the Safer Infusion System comply with the FDA's published list of pigments classified as safe for use in medical device manufacturing. These pigments are listed under the Code of Federal Regulations, Title 21, Parts 73 and 74, and are the only colors listed by the FDA for medical devices, with Subpart D applying specifically to colors for Medical Devices. The systems presented address a need for standardization of handling hazardous IV infusions that are typically costly medications. When considering minimum inhibitory concentration (MIC) dependent medications, medications with narrow therapeutic index, and medications given in the curative setting, the potential for clinical impact is concerning, especially in the setting of small-volume infusions. IV infusion administration of small volumes risks significant drug loss in the secondary administration set. After an IV infusion, the secondary administration set may retain as much as 7 mL of drug volume or 14% of a 50-mL.

The Oncology Nursing Society (ONS) recognizes the underdosing of chemotherapy as a type of medication error, and the Infusion Nurses Society (INS) states that the standardization of drug administration is a recommended strategy to minimize the risk of errors. Unfortunately, neither the ONS chemotherapy/biotherapy guidelines nor INS' Infusion Therapy Standards of Practice address potential drug loss in IV Secondary or PiggyBack (IVPB) administration sets or recommend a standard administration technique. The Closed SIS invention proposed here in supporting multiple flushing options fulfills the medical device roles that both the ONS and INS seek.

Labeling System for Active Documentation and Process Ownership in the Present Invention The final area of standardization of the Safer Infusion System services is the inclusion of documentary labeling sets as part of the sterile delivery kit. Larger caregiver institutions may make labeling materials readily available, however this is much less likely with smaller caregiver entities, and nonexistent with home care environments. Per Nunes G K, Campos J F, Silva R C. Intravenous therapy device labeling in Intensive Care Units: an integrative review. Rev Bras Enferm. 2022; 75(6):e20220049. https://doi.org/10.1590/0034-7167-2022-0049 "data were collected in 11 articles and subsequently classified, summarized and aggregated." The results stated "Pre-designed labels, with pre-defined colors and information, help to prevent medication identification errors. There is still a lack of standardization in the practice of labeling syringes, intravenous lines, infusion pumps and saline solution bags. There are errors related to the lack of labeling devices or to their performance with incomplete information." The SIS system herein alleviates not only the lack of label availability but also concerns for maintaining a sterile infusion environment by including all materials in one deliverable.

Caregivers must always be aware that one of the main exposure sites is surface contamination in preparation and administration areas per the "Reduction of Contamination with Antibiotics on Surfaces in Environmental Air in Three European Hospitals Following Implementation of a Closed-System Drug Transfer Device" doi: 10.1093/annweh/wxz010. Putting any medical device into service for administering IV fluids from a comprehensive and sterilized kit opened at the patient's location can best minimize any contamination.

To support the adoption of consistent SIS Burette documentation, the following labeling options, identifiable by color and shape, serve the goals of simple completion and subsequent installation onto the SIS hardware. Label materials should be resistant to fluids while receptive to permanent marker writing.

Figure 31:
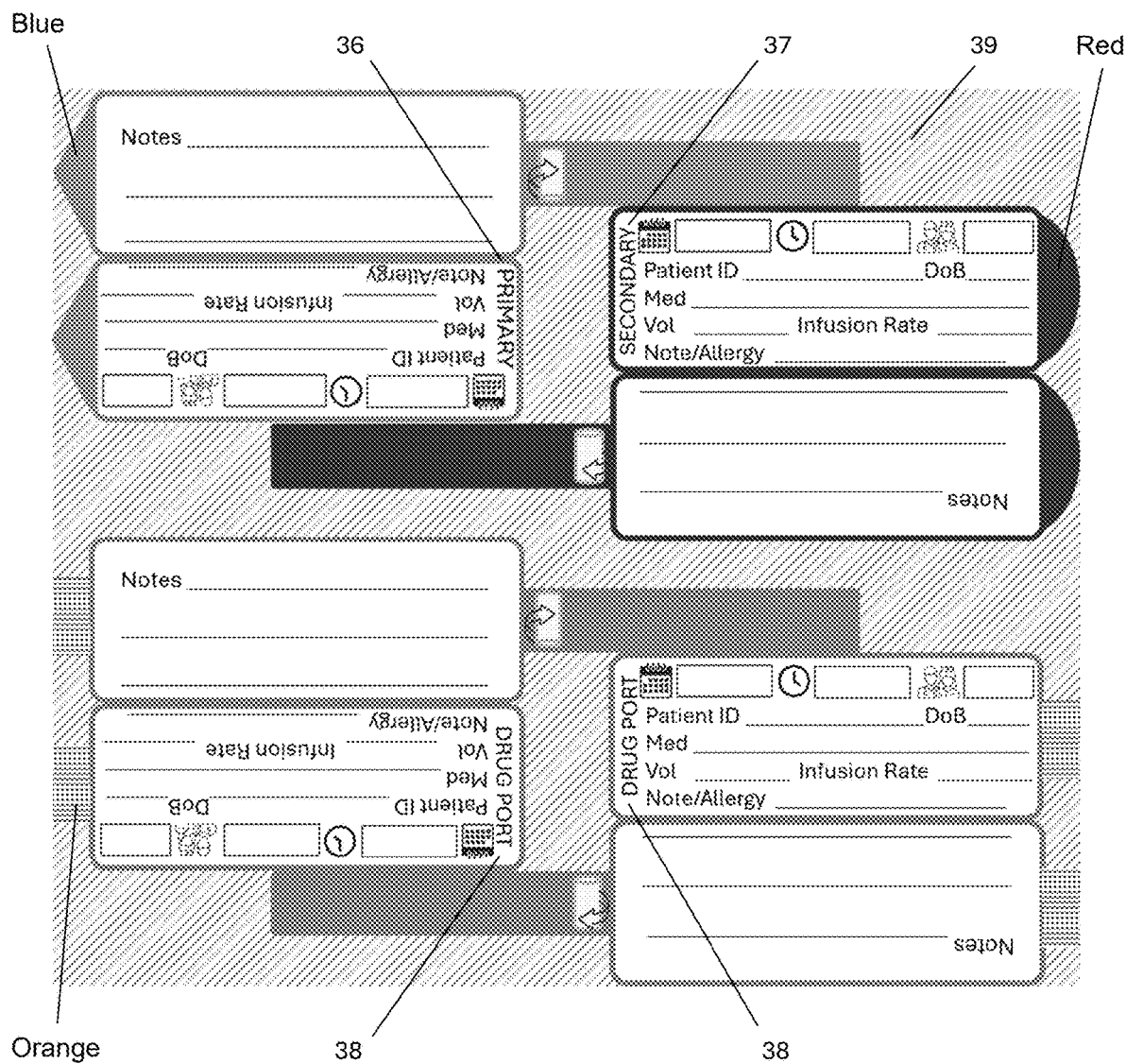
FIG. 31 illustrates a color-coding system as well as a shaped label system for the Safer Infusion System.

FIG. 31 presents one label design that can be efficiently completed by the caregiver noting the date, time, initials, patient ID, date of birth, medicine designation, volume to be dispensed, the infusion rate, and a space to note additional info such as any allergy as well as backside of the label notations. Adhesive Primary IV bag label (36) with a blue color and pointed edge, Secondary IV bag label (37) with a red color and curved edge, and two Drug Port labels (38) with an orange color and rectangular tab are nested on a carrier film (39).

Installed label options for the Primary IV bag are displayed in FIGS. 32A-F. FIG. 32A shows an adhesive label (33) pressed onto a carrier plate (34) that clips onto the IV tubing. Note that an example color blue and a point shape on the label edge design is carried through this series. FIG. 32B shows an adhesive label (33) attached to a plate with an integral zip tie element (35) for attaching around IV tubing. FIGS. 32C-F illustrate the folding process for an adhesive label design of FIG. 31 with a wraparound leg for attaching to IV tubing. The wraparound portion of the label is thinner than the label height such that multiple labels can be fit within a smaller length of IV tubing.

FIGS. 33A-F represent label options for the Secondary IV bag with an example red color and curved label edge shape.

FIGS. 34A-F represent label options for the Drug Port with an example orange color and rectangular tabbed edge shape.

Figure 35:
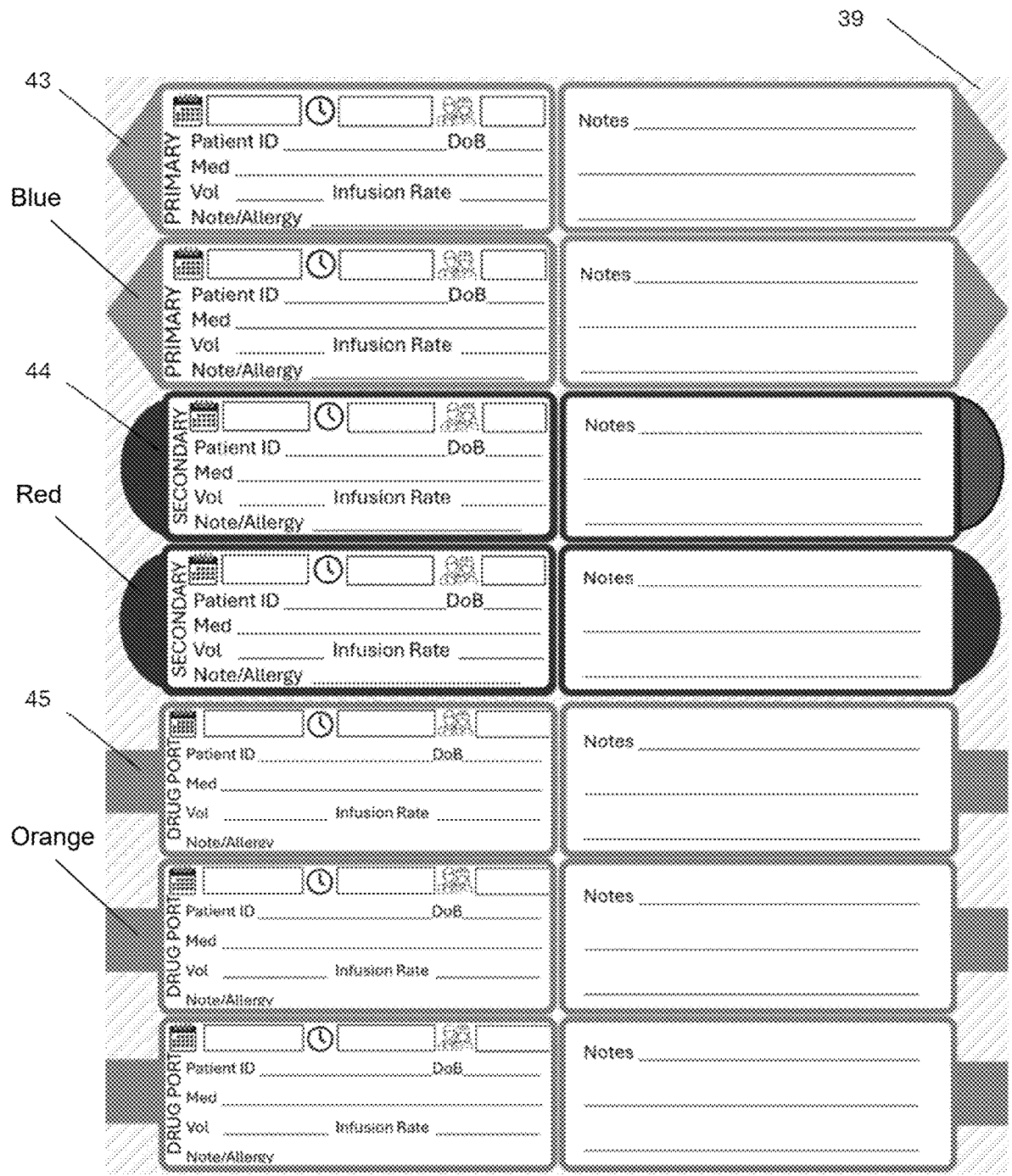
FIG. 35 illustrates a nested label set with the Primary IV bag in blue with a pointed edge, the Secondary IV bag in red with a curved edge, and the Drug Port label in orange with a rectangular tab edge.

Recognizing that attaching to the Drug Port on the SIS Burette Top Cap is not as amenable to labeling as tubing for the Primary and Secondary IV bags, an alternate label design is presented in FIG. 35. The Primary IV bag label is in blue with a pointed edged (43), the Secondary IV bag label is in red with a curved edge (44) and the Drug Port label (45) is in orange with a rectangular tab edge all nested on a release liner (39).

The process for mounting the label (45) by folding and sticking to the Burette Chamber (14) sidewall is illustrated in FIGS. 36A-C. After documentation, the adhesive side of the main label body is folded onto itself while folding the two end tabs such that they remain unbonded. Formed like wings, the adhesive side of these tabs supports attachment to the Burette Chamber (14). FIG. 36D presents multiple process documentation labels (43, 44, 45) placed on the Burette Chamber (14) such that the liquid volume marking remains visible to the caregiver. Note that the shapes, colors, and location on the Burette Chamber carry the history of the infusion events with a particular SIS system.

Figure 37A:
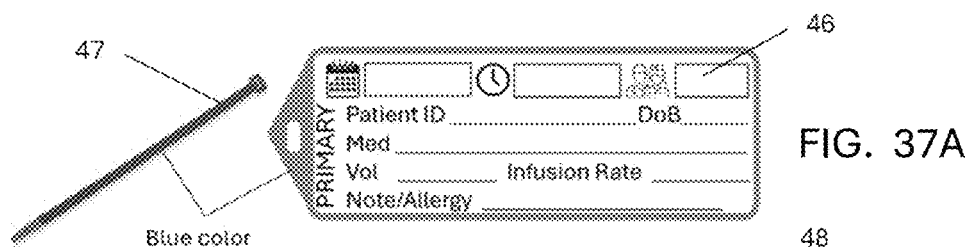
FIGS. 37A-E illustrate tag-type label sets, each with a color and a shape identifier, which attach to the SIS with zip ties that may have a matching color, all supplied in a sterile pouch with the SIS burette kit.
Figure 37B:
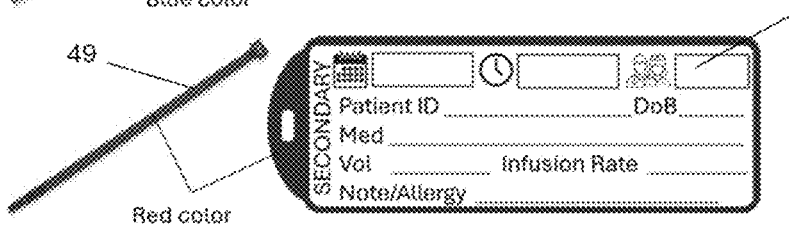
Figure 37C:
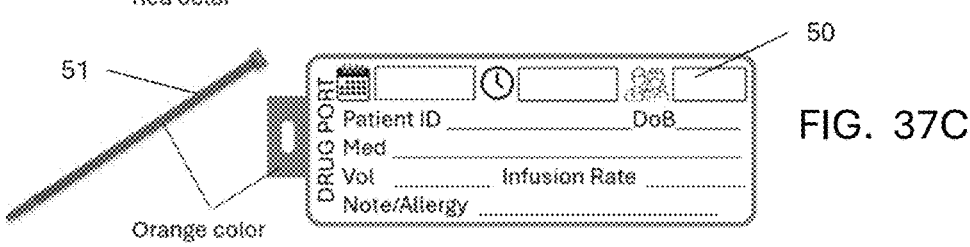
Figure 37E:
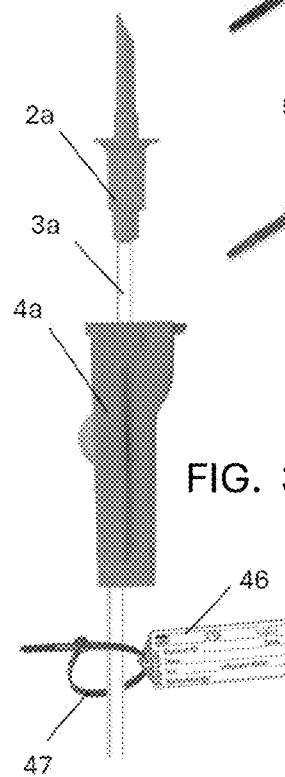
Figure 37D:
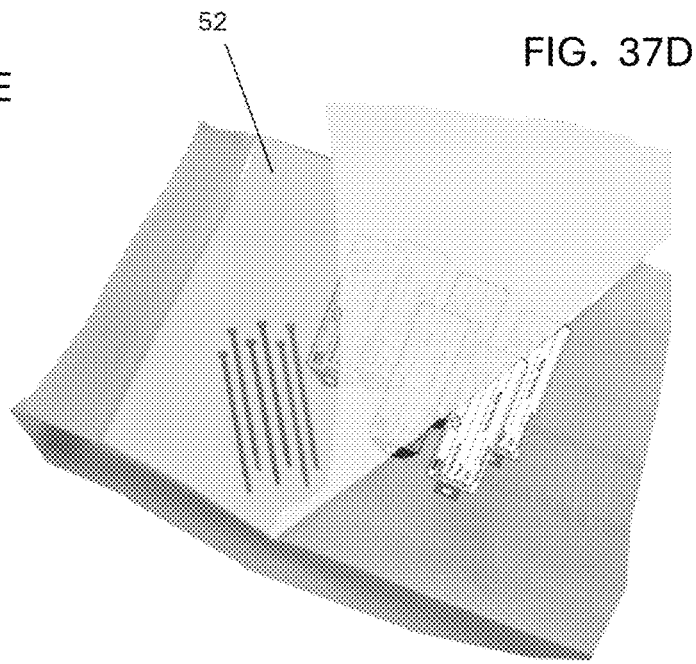
Figure 38A:
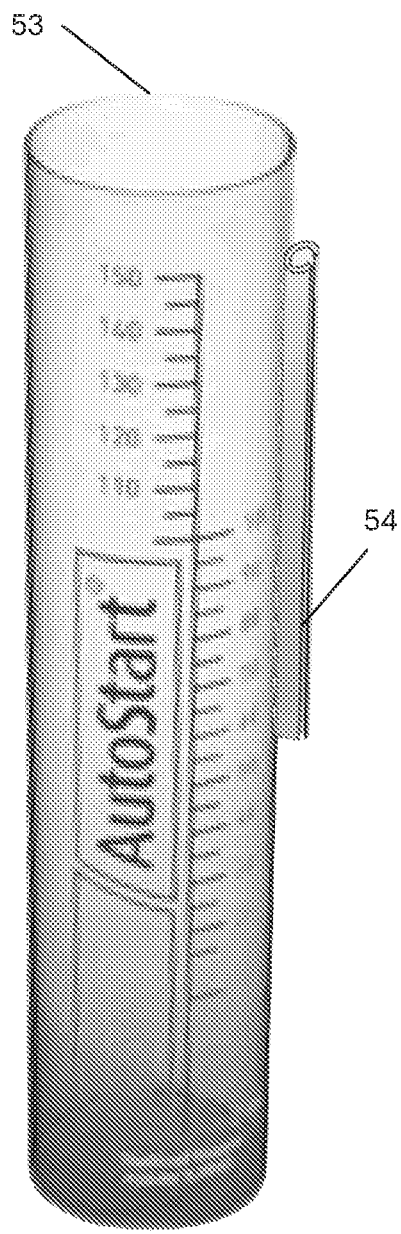
FIGS. 38A-B illustrate an extruded and molded Burette Chamber featuring a side channel with a longitudinal slot.
Figure 38B:
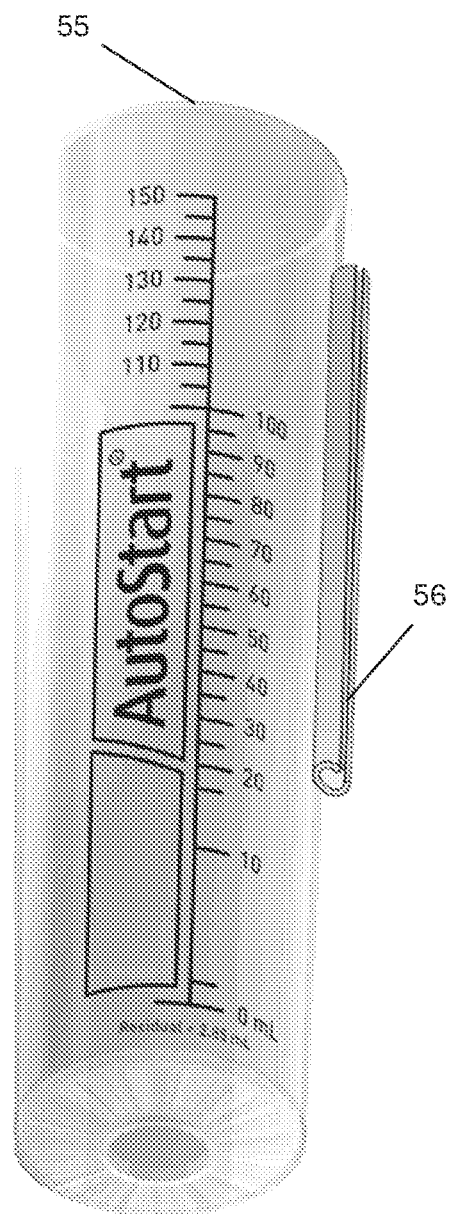

Customized quantities of each label type in a sterile SIS kit can be accommodated with individual tag labels presented in FIGS. 37A-C. Each label may have a color identifier and a shape identifier. Primary IV bag label (46) in blue with a pointed side with a hole for threading a matching-colored zip tie (47) is shown in FIG. 37A. Secondary IV bag label (48) in red with a rounded side and a hole for threading a matching-colored zip tie (49) is shown in FIG. 37B. And Drug Port label (50) in orange with a rectangular edge tab with a hole for threading matching colored zip tie (51) in FIG. 37C rounds out a set. One combination set of these labels sealed in sterile packages (52) is shown in FIG. 37D. FIG. 37E indicates a tie wrap mounted Primary IV bag label (46) on tubing (3a). A benefit of the zip tie attached around tubing is that the label can slide up and down on the IV tubing to add additional labels for following infusion events. Caution is necessary to not over-tighten the zip tie where fluid flow might be constricted.

Given that the Safer Infusion System may carry several labels, another label mounting design is presented in FIGS.

38A-B. With Burette Chamber 53 being extruded, a side channel (54) with a longitudinal slot can be added to the extrusion die and later trimmed to clear the Top Cap and Bottom Cap attachments. With the molded Burette Chamber (55), a similar side channel (56) with a longitudinal channel can be implemented in the mold tooling. The addition of this side channel supports another method of mechanically mounting labels onto the SIS.

Figure 39:
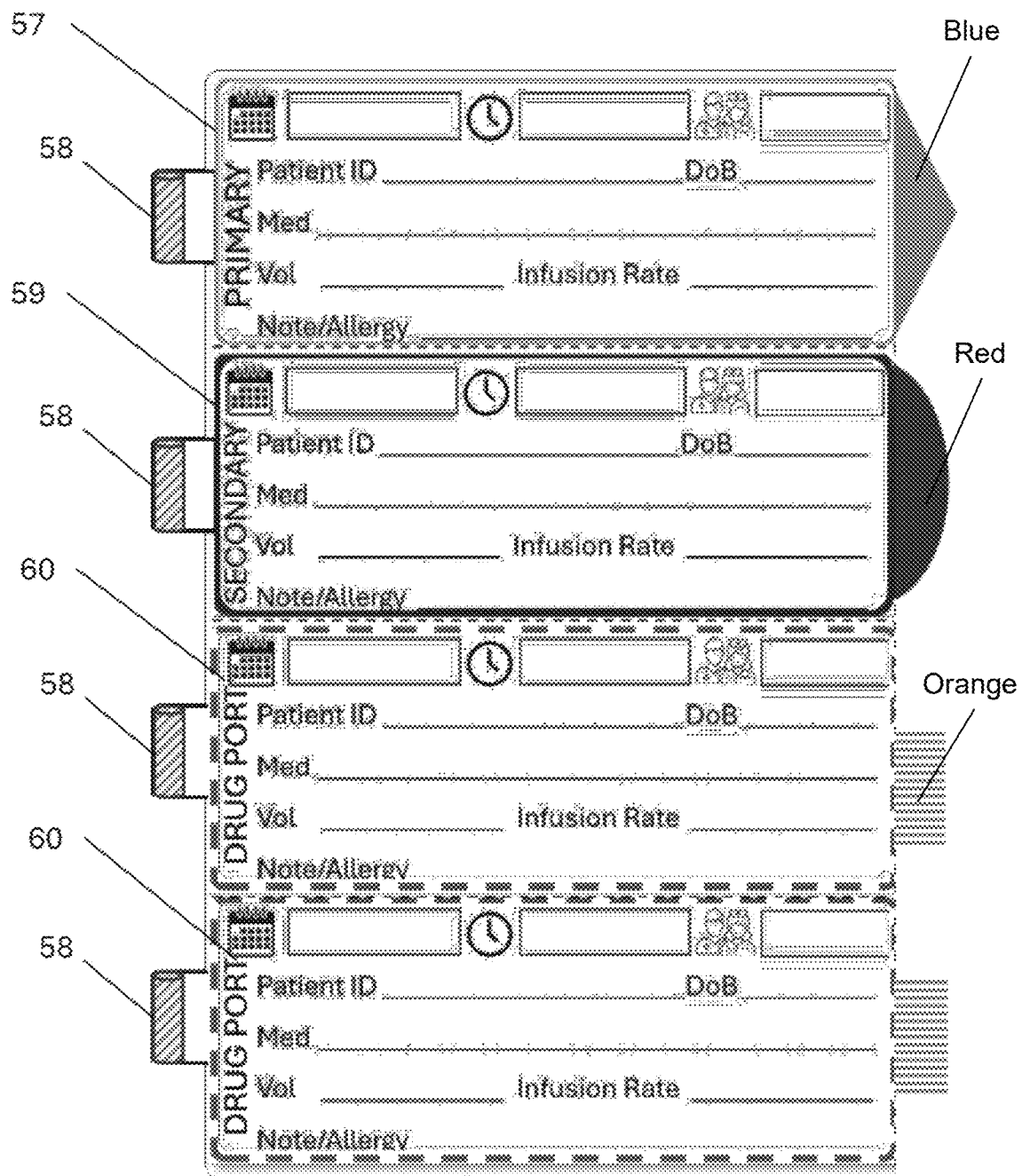
FIG. 39 illustrates a card stock-like label set with a bead element at one end that slides into the longitudinal slots on versions of the SIS Burette Chamber such that stacked labels may present priority of medical IV fluid administration.
Figure 40A:
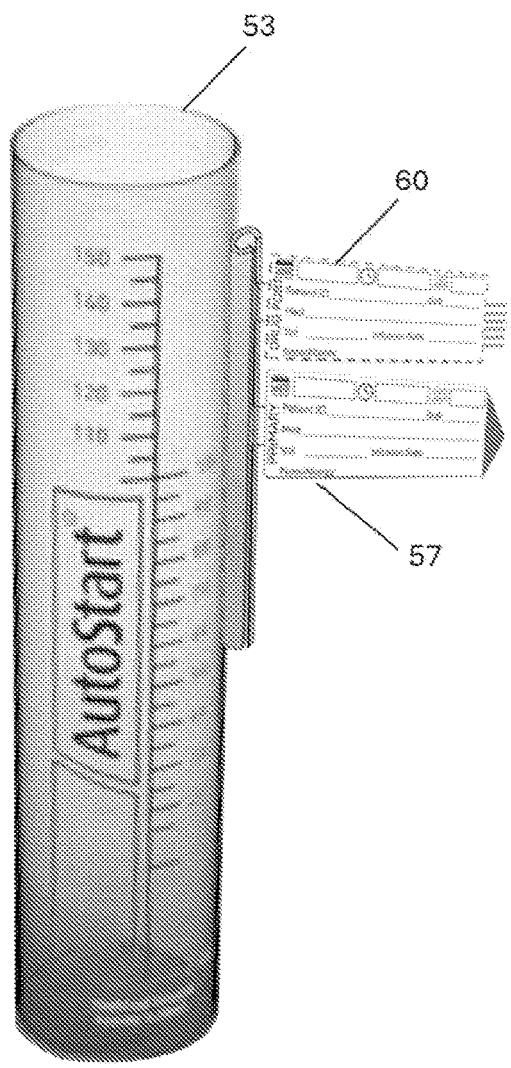
FIGS. 40A-B highlight visual benefits of label stacking on the side of SIS Burette Chambers.
Figure 40B:
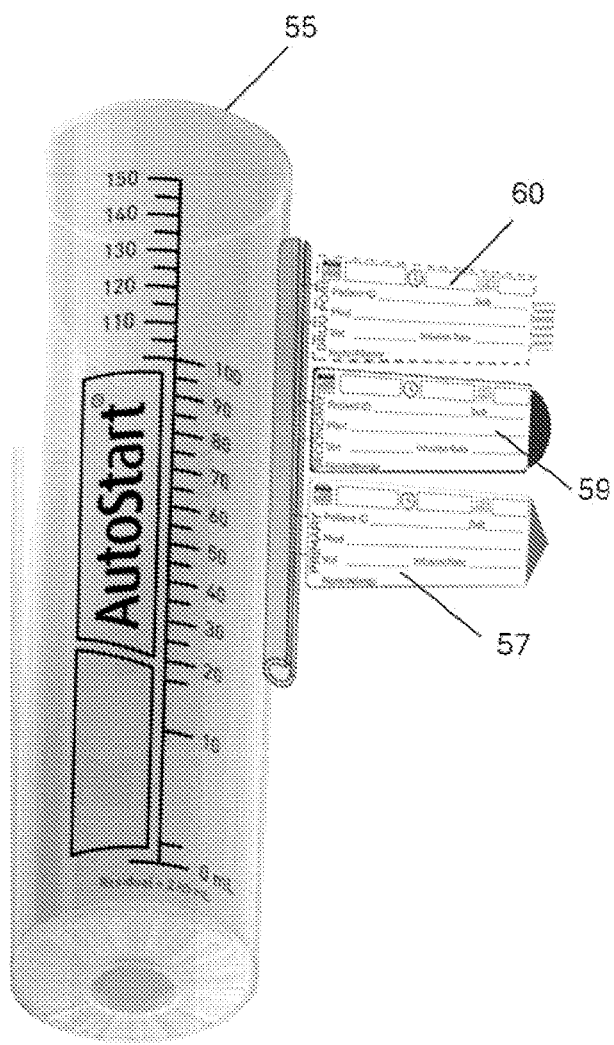

The label set design of FIG. 39 continues the theme of a color and a shaped tab edge for easy identification of IV fluids administered through the SIS Burette with Primary IV bag (57), Secondary IV bag (59), and Drug Port (60) labels supplied on a perforated sheet or by some carrier method. With this design, a thicker, card stock-like label might be preferable by caregivers. The bead element (58) on each label may be constructed in several ways such that this bead element slides easily into the longitudinal slots presented with Burette Chambers (54 and 56). The longitudinal slot cross-section might be oval, rectangular, or very low profile such that the sliding bead element (58) is very thin. When separated, the bead element (58) can slide down the side channel on the Burette Chamber with some friction for suitable retention. FIGS. 40A-B highlight the visibility of these side-mounted labels (57, 59, and 60). This channelized label stacking afforded by Burette Chambers (53 and 55) provides a clear visual of the types and the priority of medications infused through one SIS system.

Figure 41A:
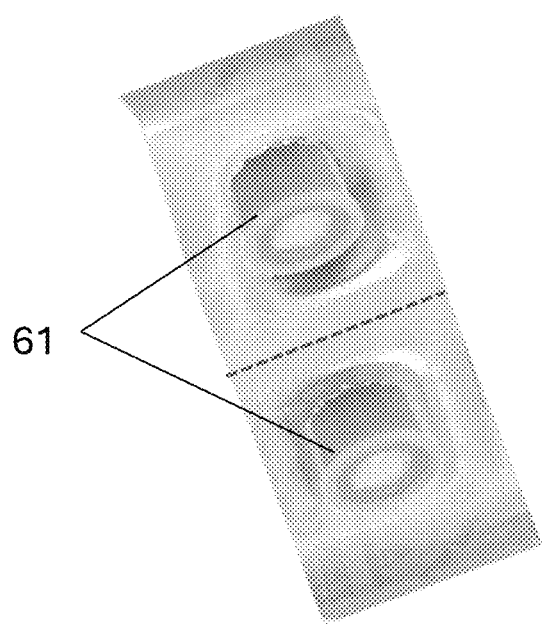
FIGS. 41A-B illustrate sterile capping materials as part of the deliverable SIS kit.
Figure 41B:
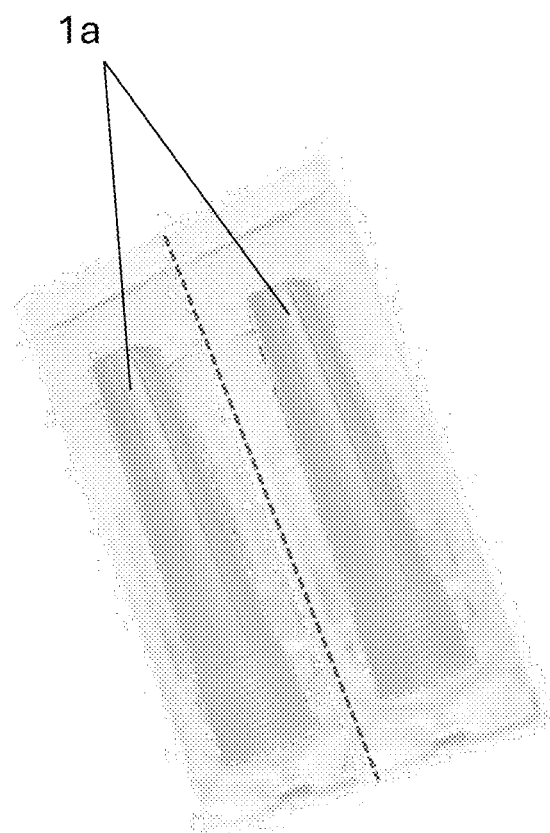

To maintain sterility upon removal of a syringe from the Drug Port Needleless connector (10) or when an IV bag is removed from a spike (2a or 2b), these fluid openings should be recapped with a sterile covering after each use. In one SIS version, the Drug Port Needleless connector initially is not supplied with a connector cap as it is sterile from the package. Good caregiver protocol is to always swab the connector surface for 15 seconds with a disinfectant before attaching further devices. Based on institution requirements and caregiver instructions, SIS kit versions may contain separately sealed and sterile packaged components for resealing fluid ports for enhanced sterile environment maintenance. FIG. 41A presents a sterile package with two needleless connector caps for resealing once the Drug Port has been exercised. FIG. 41B presents two spike port covers (1a), also sterile packaged, that can be utilized to protect the Primary IV bag spike (2a) and the Secondary IV bag spike (2b) during an IV bag change or removal from the SIS.

Figures 42A, 42B:
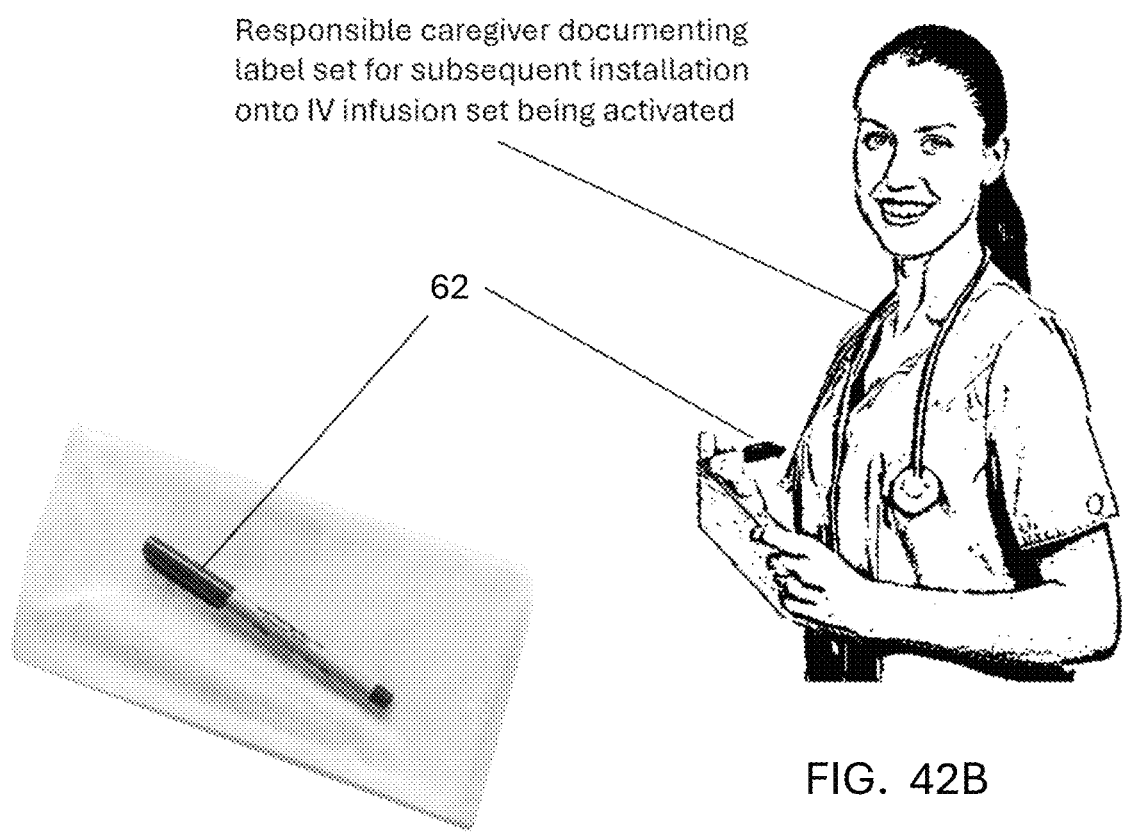
FIGS. 42A-B illustrate an indelible ink marker supplied with the Safer Infusion System as a sterile component for labeling and a responsible caregiver utilizing the sterile marker to document IV infusion events.

FIG. 42A shows a sterile packaged indelible ink marker (62) supplied with the SIS sterile kit to ensure timely documentation by the responsible caregiver FIG. 42B. Incorporation of the label sets and a sterile marker supports maintenance of a sterile environment around the patient receiving infusion therapy.

With all necessary labels and a writing instrument delivered in a sterile method as a component of the Safer Infusion System hardware packaging, the likelihood of successful medication documentation and process ownership for enhanced accuracy is increased manyfold. This simple yet important documentation is specified in many procedural documents, yet without all materials readily available, this documentation has often been ignored in observed practice.

With the Safer Infusion System supporting a 24-hour duration, the likelihood of a caregiver shift change is high further emphasizing proper onsite, attached label documentation for full awareness of past and ongoing IV infusion events.

A final consideration for the Safer Infusion System's broad infusion delivery capabilities is serving as part of disaster preparedness kits. The SIS easily sets up, relies only on gravity, and addresses a wide range of IV infusion needs likely with emergency care.

Without in any way intending to limit the scope of the present invention, the present invention includes at least the following embodiments and variations in such embodiments.

1. Rotary T-Valve and two Check Valves accommodate full AutoStart functioning with a secondary bag
   a. Check valve on the rotary T-Valve interface to the burette prevents backflow should the burette be upended during emergency care transportation or some other rigorous event
   b. Rotary T-Valve and one Check Valve on the Primary IV feed line with no Check Valve below the rotary T-Valve interface to the Burette Chamber
   c. Visual valve indicator system incorporating
      i. A physical an indent on the knob, a reveal plate, and an indicator plate integrated into the burette top assembly
2. Toggle valve, Rotary T-Valve, and one Check Valve to accommodate full AutoStart functioning with a secondary bag
   a. Integrated version of the burette top with a push/pull valve, a check valve, and an L-Port Rotary Valve supports five separate flow conditions
   b. Check valve on the drug port to the burette prevents any backflow should the burette be upended during emergency care transportation or some other rigorous event
   c. Toggle valve and Rotary T-Valve, no check valve to Burette Chamber
   d. Visual valve indicator system with an indent on the knob, a reveal plate, and an indicator plate integrated into the burette top assembly
3. L-Port Rotary Valve with one Check Valve to Burette Chamber
   a. Integrated version of the burette top with a push/pull valve, a check valve, and an L-Port Rotary Valve supports five separate flow conditions
   b. Check valve on the drug port to the burette prevents any backflow should the burette be upended during emergency care transportation or some other rigorous event
   c. L-Port Rotary Valve, no check valve to Burette Chamber
   d. Visual valve indicator system with an indent on the knob, a reveal plate, and an indicator plate integrated into the burette top assembly
4. Secondary bag can be hung at any height above the burette eliminating potential caregiver error
5. Closed system for dosing the secondary bag with a standard construction providing a dedicated spike and clamp to the primary IV bad and a dedicated spike and clamp for the secondary IV bag
6. Valve based Burette Top Cap Monoblock enables syringe flush either up to the secondary bag or directly to the burette to delivery Enhanced AutoFlush
   a. Closed system for flushing the secondary bag to minimize residual drug not being effectively delivered to the patient
7. Directed Flow Channel down the exterior of the Central Tube minimizes contact with the inner burette walls assuring that the bulk of the infused liquid is delivered to the base of the burette enabling a more complete flush of the infused liquid by only having to "rinse" the Central Tube and flow channel on the float on down to the mixing well of the burette
   a. Confinement cup added to the top of the Alignment Piece
   b. Collection cup & Flow Channel features on Float for enhanced flushing
8. Using a spiral pattern in the well of the burette bottom cap creates a swirling motion of the fluid draining into the drip chamber for enhanced mixing of the burette fluid contents
   a. Adding fin features to the foot of the burette float creates pressure on fins to force the float to rotate creating additional mixing action both in the swell as well as in upper areas of the burette
9. Adding a physical set of features, raised or lowered, to the side of the float provides a visual confirmation that IV fluid is actively being administrated
   a. Making the features colored
   b. Making the features otherwise easily noticeable
10. Toggle Valve on drip chamber that slides a macro-drip nozzle or a mini-drip nozzle enabling simple choice for managing a particular prescriptive drip rate with the single SIS assembly
11. SIS delivers a standardized height system to ensure all features are available within the "safe operating window" while ensuring that the ideal static height of 18" to 24" between the fluid in the drip chamber and the patient's IV site can be established
12. The SIS standard structure ensures a consistent environment for manual adjustments to the fluid control mechanisms typically used with IV fluid tubing such as roller clamps
13. Incorporation in the SIS deliverable sterile package are labeling system options coded for color and shape
   a. Labels are resistant to fluids while receptive to permanent marker writing
   b. Labels once written upon my be attached by way of snap-fit to tubing, zip tie, or adhesive bonding by wrap-around or direct attach methods that always present the label for ease of monitoring
14. Incorporation in the SIS deliverable sterile package is an indelible marker for inscribing relevant data on SIS labels
15. Incorporation in the SIS deliverable sterile package are spare capping materials that make include
   a. Luer type caps to protect the Drug Port upon removal of any input
   b. Spike caps protect the Primary and Secondary IV spike bodies upon removal of any input
16. SIS system deliverable as fully hazardous drug compatible setup
17. SIS system deliverable in a version that incorporates all material configurations to protect certain hazardous drugs from light exposure
   a. Colored sleeve to surround the IV bag holding the light sensitive drug
   b. Colored tubing of various constructions to protect the flowing liquid
   c. Colored SIS Burette Chamber to protect the flowing liquid
   d. Colored Drip Chamber to protect the flowing liquid
   e. Hazardous labels for attachment to SIS hardware to direct the appropriate disposal of materials following the IV infusion procedure
18. Use of a full set of pigmented materials protect light sensitive hazardous IV infusion compounds Although the foregoing detailed description is illustrative of preferred embodiments of the present invention, it is to be understood that additional embodiments thereof will be obvious to those skilled in the art. Further modifications are also possible in alternative embodiments without departing from the inventive concept.

Accordingly, it will be readily apparent to those skilled in the art that still further changes and modifications in the actual concepts described herein can readily be made without departing from the spirit and scope of the disclosed inventions.

What is claimed is:

1. A gravity-fed burette system, comprising:
   a hollow body providing a generally upright longitudinal axis which encloses a chamber to receive a liquid, wherein the chamber has a chamber outlet for delivering liquid from the chamber, a vent port from the chamber, a Primary IV bag inlet into the chamber, and a directed flow inlet into the chamber from a chamber valve;
   a Primary IV bag inlet control valve operatively associated with the Primary IV bag inlet to restrict flow from the Primary IV bag inlet into the chamber;
   a Primary IV bag branch into the chamber valve;
   a Primary IV bag branch control valve operatively associated with the Primary IV bag branch to allow liquid to flow from the Primary IV bag branch through the chamber valve into the chamber;
   a Secondary IV bag inlet into the chamber valve;
   a Secondary IV bag inlet control valve operatively associated with the Secondary IV bag inlet to allow liquid to flow from the Secondary IV bag inlet through the chamber valve into the chamber; and
   a drug port inlet into the chamber valve;
   wherein the chamber valve allows liquid to flow through the drug port inlet into the chamber in a first configuration and allows liquid to flow from the drug port inlet through the chamber valve into the Secondary IV bag inlet in a second configuration.

2. The gravity-fed burette system of claim 1, wherein the Primary IV bag inlet control valve and the Primary IV bag branch control valve are comprised of a single L-Port Rotary valve.

3. The gravity-fed burette system of claim 1, wherein the Primary IV bag inlet control valve is comprised of a clamp acting on a tubing of the Primary IV bag inlet.

4. The gravity-fed burette system of claim 1, wherein the Secondary IV bag inlet control valve is comprised of a clamp acting on a tubing of the Secondary IV bag inlet.

5. The gravity-fed burette system of claim 1, further comprising:
   a central tube operatively associated with the Primary IV bag inlet;
   a float element sealing valve operatively associated with the central tube to control flow out of the central tube;
   wherein the float element sealing valve is comprised of a float which sits on top of a liquid well located at a bottom of the chamber; and
   wherein the float element sealing valve prevents infusion of air bubbles out of the chamber outlet and functions as a dynamic flow valve for a steady keep vein open IV flush.

6. The gravity-fed burette system of claim 5, further comprising a directed flow channel operatively associated with the directed flow inlet to direct liquid introduced into the chamber through the chamber valve down along an external surface of the central tube.

7. The gravity-fed burette system of claim 6, further comprising means for causing the float to rotate within the chamber from flow of liquid in the directed flow channel.

8. The gravity-fed burette system of claim 6, further comprising means for creating a swirling motion of liquid in the liquid well.

9. The gravity-fed burette system of claim 5, further comprising a directed flow tube operatively associated with the directed flow inlet to direct liquid introduced into the chamber through the chamber valve down along an external surface of the central tube.

10. The gravity-fed burette system of claim 1, further comprising a hazardous vapor filter incorporating a micro-filtration membrane and a chemically absorptive layer responsive to vapors operatively associated with the vent port.

11. The gravity-fed burette system of claim 1, further comprising a deliverable sterile package comprising at least one first label, at least one second label, and at least one third label, wherein each of said at least one first label, at least one second label and at least one their label is visually distinctive from one another.

12. The gravity-fed burette system of claim 1, wherein said deliverable sterile package is further comprised of a sterile writing instrument.

13. The gravity-fed burette system of claim 1, further comprising:
   a drip chamber extending below the hollow body operatively associated with the chamber outlet; and
   an oncology kit comprised of:
      means for reducing UV and visible light from reaching liquid in a Secondary IV bag, a Secondary IV bag tubing, the hollow body and the drip chamber; and
      at least one hazardous material label.

14. The gravity-fed burette system of claim 1, further comprising:
   a drip chamber extending below the hollow body operatively associated with the chamber outlet; and
   a Nozzle Toggle Valve which slides laterally to position either a micro-drip nozzle or a macro-drip nozzle into a flow position below the fluid outlet into the drip chamber.

15. The gravity-fed burette system of claim 1, further comprising:
   a Primary IV bag having a Primary Spike Port; and
   a Secondary IV bag having a Secondary Spike Port;
   wherein the Primary Spike Port and the Primary IV bag inlet control valve have a first color, the Secondary Spike Port and the Secondary IV bag inlet control valve have a second color, and the first color is visually distinguishable from the second color.

16. A gravity-fed burette system, comprising:
   a primary IV bag;
   a secondary IV bag:
   a hollow body configured with a longitudinal slot providing a generally upright longitudinal axis which encloses a chamber to receive a liquid, wherein the chamber has a chamber outlet for delivering liquid from the chamber, a vent port from the chamber, a Primary IV bag inlet into the chamber, and a directed flow inlet into the chamber from a chamber valve;
   a Primary IV bag inlet control valve operatively associated with the Primary IV bag inlet and the primary IV bag to restrict flow from the Primary IV bag inlet into the chamber;
   a Primary IV bag branch into the chamber valve;
   a Primary IV bag branch control valve operatively associated with the Primary IV bag branch to allow liquid to flow from the Primary IV bag branch through the chamber valve into the chamber;
   a Secondary IV bag inlet into the chamber valve;
   a Secondary IV bag inlet control valve operatively associated with the Secondary IV bag inlet and the secondary IV bag to allow liquid to flow from the Secondary IV bag inlet through the chamber valve into the chamber; and
   a drug port inlet into the chamber valve;
   one or more first documentation labels bearing a first visual designation associated with the primary IV bag;
   one or more second documentation labels bearing a second visual designation associated with the secondary IV bag; and
   one or more third documentation labels bearing a third visual designation associated with the drug port inlet;
   wherein the chamber valve allows liquid to flow through the drug port inlet into the chamber in a first configuration and allows liquid to flow from the drug port inlet through the chamber valve into the Secondary IV bag inlet in a second configuration;
   wherein each of the one or more first documentation labels, each of the one or more second documentation labels and each of the one or more third documentation labels are visually distinctive from one another; and
   wherein said one or more first, second and third labels are configured to be received by the longitudinal slot so as to provide a visual identification of the types and the priority of liquids infused through the gravity-fed burette system.

17. The gravity-fed burette system of claim 16, wherein the first visual designation is comprised of both a first color and a first shape; the second visual designation is comprised of both a second color and a second shape; and the third visual designation is comprised of both a third color and a third shape.

* * * * *